US006710170B2

(12) United States Patent
Xu et al.
(10) Patent No.: US 6,710,170 B2
(45) Date of Patent: Mar. 23, 2004

(54) COMPOSITIONS AND METHODS FOR THE THERAPY AND DIAGNOSIS OF OVARIAN CANCER

(75) Inventors: Jiangchun Xu, Bellevue, WA (US); John A. Stolk, Bothell, WA (US); Paul A. Algate, Issaquah, WA (US); Steven P. Fling, Bainbridge Island, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/825,294

(22) Filed: Apr. 3, 2001

(65) Prior Publication Data

US 2002/0004491 A1 Jan. 10, 2002

Related U.S. Application Data

(63) Continuation-in-part of application No. 09/713,550, filed on Nov. 14, 2000, which is a continuation-in-part of application No. 09/656,668, filed on Sep. 7, 2000, which is a continuation-in-part of application No. 09/640,173, filed on Aug. 15, 2000, which is a continuation-in-part of application No. 09/561,778, filed on May 1, 2000, which is a continuation-in-part of application No. 09/394,374, filed on Sep. 10, 1999, now abandoned.

(51) Int. Cl.[7] .......................... C07H 21/00; C12N 15/00; C12N 5/00

(52) U.S. Cl. .................... 536/23.1; 536/24.3; 536/25.3; 435/320.1; 435/325

(58) Field of Search ........................... 514/44; 536/23.1, 536/25.3, 24.3; 435/320.1, 325

(56) References Cited

FOREIGN PATENT DOCUMENTS

| | | |
|---|---|---|
| DE | 20103510 U1 | 8/1998 |
| EP | 1067182 A2 | 1/2001 |
| WO | WO 98/37418 | 8/1998 |
| WO | WO 00/61629 | 10/2000 |
| WO | WO 00/77026 | 12/2000 |
| WO | WO 01/36685 | 5/2001 |
| WO | WO 01/47944 | 7/2001 |
| WO | WO 01/81634 | 11/2001 |

OTHER PUBLICATIONS

Genomics (1997) vol. 46, No. 3:426–434.*
Database EMBL Accession No. AA536804, Jul. 31, 1997.
Database EMBL Accession No. AC016957, Dec. 14, 1999.
Database EMBL, Accession No. AF060226, May 6, 1998.
Database EMBL, Accession No. AX001326, Mar. 10, 2000.
Database EMBL, Accession No. X02662, May 7, 1999.
GenBank Accession No. AA173383, Sep. 30, 1997.
GenBank Accession No. AA173739, Sep. 30, 1997.
Gibson et al., "Novel method for real time quantitative RT–PCR," *Genome Research* 6:995–1001, Oct. 1996.
Heid et al., "Real time quantitative PCR," *Genome Research* 6:986–994, Oct. 1996.
Meden and Kuhn, "Overexpression of the oncogene c–crbB–2 (HER2/neu) in Ovarian cancer: a new prognostic factor," *European Journal of Obsterics & Gynecology and Reproductive Biology 71*:173–179, 1997.
Schena et al., "Quantitative monitoring of gene expression patterns with a complementary DNA microarray," *Science 270*:467–470, Oct. 20, 1995.
GenBank Database, Acccession No. $NM_{13}$ 001508, Dec. 15, 1997.
GenBank Database, Accession No. $NP_{13}$ 001499, Dec. 15, 1997.
Genseq (Derwent) Database, Accession No. AAK54063, Nov. 16, 2001.
Genseq (Derwent) Database, Accession No. AAL27277, Jan. 24, 2002.
Genseq (Derwent) Database, Accession No. AAL33984, Jan. 24, 2002.
Genseq (Derwent) Database, Accession No. AAL33985, Jan. 24, 2002.
Genseq (Derwent) Database, Accession No. AAL33986, Jan. 24, 2002.
Database NCBI; Accession No. AX136281; May 30, 2001.
Database NCBI; Accession No. BAA95101; Jun. 30, 2000.
Database NCBI; Accession No. AB041649; Jun. 30, 2000.

* cited by examiner

*Primary Examiner*—Marjorie Moran
*Assistant Examiner*—Lori A. Clow
(74) *Attorney, Agent, or Firm*—Eric M. Barzee; Cynthia L. Shumate

(57) ABSTRACT

Compositions and methods for the therapy and diagnosis of cancer, particularly ovarian cancer, are disclosed. Illustrative compositions comprise one or more ovarian tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly ovarian cancer.

5 Claims, No Drawings

SEQUENCE LISTING

```
<160> NUMBER OF SEQ ID NOS: 215

<210> SEQ ID NO 1
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 1

caacctcact agtaaatgaa agaaatattg taatttgtat ttgatctgct gggtctttgg     60

agtcagaact ggttttatca gcagtttgat cttctgaggt ctggtatgta gtttgctggc    120

ccacagaacc ttcacgtgta ttcacagcct caatgccata aggaaactct tttagaagtt    180

ctgacagctg gtcatgtagg tataagacag gtgccttatc actgtggatt tcatttcttg    240

caggatcttg gggagtatag ttgctggatg catctatttc ctgagggtaa atatcctcct    300

ggncgacgcg gccgctcgag tctagagggc ccgtttaaac ccgctgatca gcctcgactg    360

tgccttctan ttgccancca tntgttgttt gcccct                              396


<210> SEQ ID NO 2
<211> LENGTH: 396
<212> TYPE: DNA
<213> ORGANISM: Homo sapien

<400> SEQUENCE: 2

cgaccaaaaa gtaaactcca agtgaacatc aaatcaaatc taatcctttt ggccacatga     60

ctggttgttc tttatctcat agttacaatg aatcatataa actgtagact gccactacca    120

cgatacttct gtgacacaga aggaatgtcc tatttgccta tctatctgag gaatgttaaa    180

tagagaaaaa tagattataa aacaacctgg aggtcacagg attctgagat aatccctctg    240

ttaaaaaaca tctgaacagc aaatgtccaa tctgtaataa aatagttaaa ggtccaagtc    300

aagtccactt ctacttggct ggcccagcac aagaaatcta acagcacttt gtaatcattt    360

tgcttttcta attttcccgg aggacatggg ccattg                              396
```

-continued

<210> SEQ ID NO 3
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 3 cgccctttt tttttttttt tnattggnnn aantcncttt nantnnaaaa acntgnangg 60
naancccann cccnnggnac cannnccagg agttgggtgg anactgagtg gggtttgtgt 120
gggtgagggg gcatctactc ctnttgcaac aagccaaaag tagaacagcc taaggaaaag 180
tgacctgcct tggagcctta gtccctccct tagggccccc tcagcctacc ctatccaagt 240
ctgaggctat ggaagtctcc ctcctagttc actagcaggt tccccatctt ttccaggctg 300
cccctagcac tccacgtttt tctgaaaaaa tctanacagg ccctttttgg gtacctaaaa 360
cccagctgag gttgtgagct tgtaaggtaa agcaag 396

<210> SEQ ID NO 4
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 4
gaccaatcct tgncncacta ncaaaangac cccnctnacc nccaggaact gaacctnnnt 60
gtnnacctcc nnctgcnnag ccntatntcc aanatcaccc accgtatcca ctgggaatct 120
gccagcctcc tgcgatcaga agagaccaat cgaaaatgag ggtttcacan tcacagctga 180
aggaaaaggc caaggcacct tgtcggnggn gacaatgtac catgctaagg ccaaagatca 240
actcacctgt aataaattcg acctcaaggt caccataaaa ccagcaccgg aacagaaaaa 300
gaggcctnag gatgcccaag aaacactttt gatcctttga aaactgtacc aaggtaccgg 360
ggggagaccc aggaaaggnc cnttatgtnt nnntnt 396

<210> SEQ ID NO 5
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 5
gacgccggag ctgccgcgcc agtcgcctag caggtcctct accggcttat tcctgtgccg 60
gatcttcatc ggcacagggg ccactgagac gtttctgcct ccctctttct tcctccgctc 120
tttctcttcc ctctngttta gtttgcctgg gagcttgaaa ggagaaagca cnggggtcgc 180
cccaaaccct ttctgcttct gcccatcaca agtgccacta ccgccatggg cctcactatc 240
tcctccctct tctcccgact atttggcaag aagcagatgc gcattttgat ggttggattg 300
gatgctgctg gcaagacaac cattcttgat aaactgaaag tangggganat aagnaccacc 360 atttctacca ttgggtttaa tgggggaaac agtana 396

-continued

<210> SEQ ID NO 6
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 6
acgggaggcg ccgggaagtc gacggcgccg gcggctcctg caggaggcca ctgtctgcag 60
ctcccgtgaa gatgtccact ccagacccac ccctgggcgg aactcctcgg ccaggtcctt 120
ccccgggccc tgcccttccc ctggagccat gctgggccct agcccgggtc cctcgccggg 180
ctccgcccac agcatgatgg ggcccagccc angggccgcc ctcagcagga caccccatcc 240
ccacccaggg gcctggaggg taccctcagg acaacatgca ccagatgcac aagcccatgg 300
agtccatgca tgagaagggc atgtcggacg acccgcgcta caaccagatg aaaggaatgg 360
ggatgcggtc agggggccat gctgggatgg ggcccc 396

<210> SEQ ID NO 7
<211> LENGTH: 396
<212> TYPE: DNA
<213> ORGANISM: Homo sapien

<400> SEQUENCE: 7
acccgagagt cgtcggggtt tcctgcttca acagtgcttg gacggaaccc ggcgctcgtt 60
ccccaccccg gccggccgcc catagccagc cctccgtcac ctcttcaccg caccctcgga 120
ctgccccaag gcccccgccg ccgctccagc gccgcgcagc caccgccgcc gccgccgcct 180
ctccttagtc gccgccatga cgaccgcgtc cacctcgcag gtgcgccaga actaccacca 240
ggactcagag gccgccatca accgccagat caacctggag ctctacgcct cctacgttta 300
cctgtccatg tcttactact ttgaccgcga tgatgtggct ttgaagaact ttgccaaata 360
ctttcttcac caatctcatg aggagaggga acatgc 396

<210> SEQ ID NO 8
<211> LENGTH: 396
<212> TYPE: DNA
<213> ORGANISM: Homo sapien

<400> SEQUENCE: 8
cgacaacaag gttaatacct tagttcttaa catttttttt ctttatgtgt agtgttttca 60
tgctaccttg gtaggaaact tatttacaaa ccatattaaa aggctaattt aaatataaat 120
aatataaagt gctctgaata aagcagaaat atattacagt tcattccaca gaaagcatcc 180
aaaccaccca aatgaccaag gcatatatag tatttggagg aatcaggggt ttggaaggag 240
tagggaggag aatgaaggaa aatgcaacca gcatgattat agtgtgttca tttagataaa 300
agtagaaggc acaggagagg tagcaaaggc caggcttttc tttggttttc ttcaaacata 360
ggtgaaaaaa acactgccat tcacaagtca aggaac 396

<210> SEQ ID NO 9
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G -continued

<400> SEQUENCE: 9
tcgacatcgc ggcaactttt tgcggattgt tcttgcttcc aggctttgcg ctgcaaatcc 60
agtgctacca gtgtgaagaa ttccagctga acaacgactg ctcctccccc gagttcattg 120
tgaattgcac ggtgaacgtt caagacatgt gtcagaaaga agtgatggag caaagtgccg 180
ggatcatgta ccgcaagtcc tgtgcatcat cagcggcctg tctcatcgcc tctgccgggt 240
accagtcctt ctgctcccca gggaaactga actcagtttg catcagctgc tgcaacaccc 300
ctctttgtaa cgggccaagg nccaaaaaaa ggggaaagtt ctgncctcgg ccctcaggcc 360
agggctccgc accaccatcc tgttcctcaa attagc 396

<210> SEQ ID NO 10
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 10
cctttttttt tttttttttt tttttttttt tttttttttt tttttttttt tttttttttt 60
tttttttttt tttttttttt tttttttttt tttttttttt ttttaaaaaa aaaannnttt 120 ttttttttn aaaaaaangg gnnnnntttt ttncccnnnn gggngggggg ggggnnnnnt 180
ttnaaanaaa aaaaccnnaa annnnngggg nnnannnaan nncccncccc naancnntaa 240
aaaannnggn aaaanagggg gggnannnnn nngggggggna aaanttttttt ttttttnaag 300 ggnnnggnaa aaaantnnnn nnnttttttt ttnnaanngg gnnaaaaaaa aaaaaaaaaa 360
attttttngg gntnaggggn nggggggaaaa ncccna 396

<210> SEQ ID NO 11
<211> LENGTH: 396
<212> TYPE: DNA
<213> ORGANISM: Homo sapien

<400> SEQUENCE: 11
agaacacagg tgtcgtgaaa actacccta aaagccaaaa tgggaaagga aaagactcat 60
atcaacattg tcgtcattgg acacgtagat tcgggcaagt ccaccactac tggccatctg 120
atctataaat gcggtggcat cgacaaaaga accattgaaa aatttgagaa ggaggctgct 180
gagatgggaa agggctcctt caagtatgcc tgggtcttgg ataaactgaa agctgagcgt 240
gaacgtggta tcaccattga tatctccttg tggaaatttg agaccagcaa gtactatgtg 300
actatcattg atgccccagg acacagagac tttatcaaaa acatgattac agggacatct 360
caggctgact gtgctgtcct gattgttgct gctggt 396

<210> SEQ ID NO 12
<211> LENGTH: 396
<212> TYPE: DNA
<213> ORGANISM: Homo sapien

<400> SEQUENCE: 12
cgaaaacctt taaaccccgg tcatccggac atcccaacgc atgctcctgg agctcacagc 60
cttctgtggt gtcatttctg aaacaagggc gtggatccct caaccaagaa gaatgtttat 120
gtcttcaagt gacctgtact gcttggggac tattggagaa aataaggtgg agtcctactt 180

-continued

```
gtttaaaaaa tatgtatcta agaatgttct agggcactct gggaacctat aaaggcaggt    240

atttcgggcc ctcctcttca ggaatcttcc tgaagacatg gcccagtcga aggcccagga    300

tggcttttgc tgcggccccg tggggtagga gggacagaga gacagggaga gtcagcctcc    360

acattcagag gcatcacaag taatggcaca attctt                              396


<210> SEQ ID NO 13
<211> LENGTH: 396
<212> TYPE: DNA
<213> ORGANISM: Homo sapien

<400> SEQUENCE: 13

accacaggct ggccacaaga agcgctggag tgtgctggcg gctgcaggcc tacggggcct     60

ggtccggctg ctgcacgtgc gtgccggctt ctgctgcggg gtcatccgag cccacaagaa    120

ggccatcgcc accctgtgct tcagccccgc ccacgagacc catctcttca cggcctccta    180

tgacaagcgg atcatcctct gggacatcgg ggtgcccaac caggactacg aattccaggc    240

cagccagctg ctcacactgg acaccacctc tatccccctg cgcctctgcc ctgtcgcctc    300

ctgcccggac gcccgcctgc tggccggctg cgagggcggc tgctgctgct gggacgtgcg    360

gctggaccag ccccaaaaga ggagggtgtg tgaagt                              396


<210> SEQ ID NO 14
<211> LENGTH: 396
<212> TYPE: DNA
<213> ORGANISM: Homo sapien

<400> SEQUENCE: 14

acggcgtcct cgtggaagtg acatcgtctt taaaccctgc gtggcaatcc ctgacgcacc     60

gccgtgatgc ccagggaaga cagggcgacc tggaagtcca actacttcct taagatcatc    120

caactattgg atgattatcc gaaatgtttc attgtgggag cagacaatgt gggctccaag    180

cagatgcagc agatccgcat gtcccttcgc gggaaggctg tggtgctgat gggcaagaac    240

accatgatgc gcaaggccat ccgagggcac ctggaaaaca acccagctct ggagaaactg    300

ctgcctcata tccgggggaa tgtgggcttt gtgttcacca aggaggacct cactgagatc    360

agggacatgt tgctggccaa taaggtgcca gctgct                              396


<210> SEQ ID NO 15
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 15

accgcgcggg cacagggtgc cgctgaccga ggcgtgcaaa gactccagaa ttggaggcat     60

gatgaagact ctgctgctgt ttgtggggct gctgctgacc tgggagagtg ggcaggtcct    120

gggggaccag acggtctcag acaatgagct ccaggaaatg tccaatcagg gaagtaagta    180

cgtcaataag gaaattcaaa atgcttgtca acggggtgaa acagataaag actctcatag    240

aaaaaacaaa cgaagagcgc aagacactgc tcagcaacct agaagaagcc aagaagaaga    300

aagaggatgc cctaaatgag accagggaat canagacaaa gctgaaggag ctcccaggag    360

tgtgcaatga gaccatgatg gccctctggg aagagt                              396
```

-continued

<210> SEQ ID NO 16
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 16
tttttttttt tttttttttt tttttttttt tttttttttt tttttttttt tttttttttt 60
tttttttttt tttttttttt tttttttttt tttttttttt tttttttttt tttngggggg 120
nnnaaanttt tttntnanan nnnngggnaa aaaaaaaaaa aanaangggg gnnntnnggc 180
ccnnnanaaa aaaanngnna annaancccc ccnnnnnnnc ccncnnntnn ggaaananna 240
aaaccccccc cngggnnggg nnaaaaannc ccnggggnan tttttatnnn anncccccccc 300 ccnggggggg gnggaaaaaa aaaantnccc ccnannaaaa nnggggnccc cccnttttnc 360 aaaangggggg nccgggcccc ccnnantntt nggggg 396

<210> SEQ ID NO 17
<211> LENGTH: 396
<212> TYPE: DNA
<213> ORGANISM: Homo sapien

<400> SEQUENCE: 17
accacactaa ccatatacca atgatggcgc gatgtaacac gagaaagcac ataccaaggc 60
caccacacac cacctgtcca aaaaggcctt cgatacggga taatcctatt tattacctca 120
gaagtttttt tcttcgcagg atttttctga gccttttacc actccagcct agcccctacc 180
ccccaactag gagggcactg gcccccaaca ggcatcaccc cgctaaatcc cctagaagtc 240
ccactcctaa acacatccgt attactcgca tcaggagtat caatcacctg agctcaccat 300
agtctaatag aaaacaaccg aaaccaaata attcaagcac tgcttattac aattttactg 360
ggtctctatt ttaccctcct acaagcctca gagtac 396

<210> SEQ ID NO 18
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 18
tttttttttt tttttttttt tttttttttt tttttttttt ttttttttta ntcnaaaggg 60 gaaggncccct ttttattaaa nttggncatt ttactttnct tttttnaaaa ngctaanaaa 120
aaanttttnt ttntncttaa aaaaaccctn natntcacna ncaaaaaaaa cnattcccnc 180
ntncnttttg tgataaaaaa aaaggcaatg gaattcaacn tancctaana aaactttncc 240
tgggaggaaa aaaaattnnt ccgngggaaa cacttggggc tntccaaant gnanccatnc 300
tangaggacc ntctntaaga tttccaaang aaaccccttc ctnccaaang nantaccccg 360
ntgcctacnn cccataaaaa aaacctcanc cntaan 396

<210> SEQ ID NO 19
<211> LENGTH: 396
<212> TYPE: DNA
<213> ORGANISM: Homo sapien
<220> FEATURE:

-continued

<221> NAME/KEY: misc_feature
<222> LOCATION: (1)...(396)
<223> OTHER INFORMATION: n = A,T,C or G

<400> SEQUENCE: 19
tttttttttt tttttttttt tttttttttt tttttttttt ttttttntgg tctgggcttt 60
tattttacna aaaanctaan ggnaaanntn cnttaaacta antngaanac aaagtnttaa 120
ngaaaaaggn ctgggggnnt cntttacaaa aanggncngg gncanntttg ggcttaaaan 180
ttcaaaaagg gnncntcaaa ngggtttgca tttgcatgtt tcancnctaa ancgnangaa 240
naaacccngg ngnccnctgg gaaaagttnt tnanctncca aaanatnaan tntttgnanc 300
agggnntttt tgggnaaaaa aannanttcc anaaactttc catcccctgg ntttgggttc 360
ggccttgngt tttcggnatn atntccntta angggg 396

<210> SEQ ID NO 20
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 20
tttttttttt tttttttttt ttttttctna acaaaccctg ttnttgggng ggngngggta 60
taatactaag ttganatgat ntcatttacg ggggaaggcn ctttgtgaan naggccttat 120
ttctnttgnc ctttcgtaca gggaggaatt tgaagtaaan anaaaccnac ctggattact 180
ccggtctgaa ctcaaatcac gtaggacttt aatcgttgaa caaacaaacc tttaatagcg 240
gctgcnccat tgggatgtcc tgatccaaca tcgaggncgt aaaccctatt gttgatatgg 300
actctaaaaa taggattgcg ctgttatccc tagggtaact tgttcccgtg gtcaaagtta 360
ttggatcaat tgagtataag tagttcgctt tgactg 396

<210> SEQ ID NO 21
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 21
acatanatnt tatactanca ttnaccatct cacttgnagg aanactanta tatcnctcac 60
acctnatatc ctncntacta tgcctagaag gaataatact atngctgttn attatancta 120
ctntnataac cctnaacacc cactccctct tanccaatat tgtgcctatt gccatactag 180
tntttgccgc ctgcnaagca gnggngggcc tanccntact agnctcaatc tccaacacnt 240
atggcctana ctacgtacat aacctaaacc tactcnaatg ctaaaactaa tcnncccaac 300
anttatntta ctaccactga catgactttc caaaaaacac atantttgaa tcaacncanc 360
cacccacanc ctanttatta ncatcatccc cntact 396

<210> SEQ ID NO 22
<211> LENGTH: 396
<212> TYPE: DNA
<213> ORGANISM: Homo sapien
<220> FEATURE:
<221> NAME/KEY: misc_feature -continued

```
<222> LOCATION: (1)...(396)
<223> OTHER INFORMATION: n = A,T,C or G

<400> SEQUENCE: 22

tttttttttt ttttganaaa agccggcata aagcactttt attgcaataa taaaacttga     60

gactcataaa tggtgctggg ggaagggtgc agcaacgatt tctcaccaaa tcactacaca    120

ggacagcaaa ggggtgagaa ggggctgagg gaggaaaagc caggaaactg agatcagcag    180

agggagccaa gcatcaaaaa acaggagatg ctgaagctgc gatgaccagc atcattttct    240

taanagaaca ttcaaggatt tgtcatgatg gctgggcttt cactgggtgt taagtctaca    300

aacagcacct tcaattgaaa ctgtcaatta aagttcttaa gatttaggaa gtggtggagc    360

ttggaaagtt atgagattac aaaattcctg aaagtc                              396


<210> SEQ ID NO 23
<211> LENGTH: 396
<212> TYPE: DNA
<213> ORGANISM: Homo sapien

<400> SEQUENCE: 23

acaaaggcgg ttccaagcta aggaattcca tcagtgcttt tttcgcagcc accaaattta     60

gcaggcctgt gaggttttca tatcctgaag agatgtattt taaagctttt tttttttaat    120

gaaaaaatgt cagacacaca caaaagtaga atagtaccat ggagtcccca cgtacccagc    180

ctgcagcttc aacagttacc acatttgcca accggagaga ctgccaaggc aggaaaaagc    240

cctggaaagc ccacggcccc tttttccctt gggtcagagg ccttagagct ggctgccaaa    300

gcagccaacc aaaggggcag ctcagctcct tcgtggcacc agcagtgttc ctgatgcagt    360

tgaagagttg atgtctttga caacatacgg acactg                              396


<210> SEQ ID NO 24
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 24

cgactatcct ctcagattct tatctggcac taatttataa ctattatatt atcagagact     60

atgtagcaat atatcagtgc acaggcgcat cccaggcctg tacagatgta tgtctacacg    120

taagtataaa tgaatttgca taccaggttt tacacttgca tctctaatag agattaaaaa    180

caacaaattg gcctcttcct aagtatatta atatcattta tccttacatt ttatgcctcc    240

ccctaaatta atgactgagt tggtggaaag cggctaggtt ttattcatac tgtttttttgt    300

tctcaacttc aanagtaatc tacctctgaa aaatttntan tttaatattn nnnnnnagga    360

atttgngcca ctttannnct tncnntntnn tnnccn                              396


<210> SEQ ID NO 25
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 25
```

-continued

```
tttttttttt tttttttttt gtcttttaaa aaatataaaa gtgttattat tttaaaacat     60

caagcattac agactgtaaa atcaattaan aactttctgt atatgaggac aaaaatacat    120

ttaanacata tacaanaaga tgctttttcc tgagtagaat gcaaactttt atattaagct    180

tctttgaatt ttcaaaatgt aaaataccaa ggctttttca catcagacaa aaatcaggaa    240

tgttcacctt cacatccaaa aagaaaaaaa aaaaaaancc aattttcaag ttgaagttna    300

ncaanaatga tgtaaaatct gaaaaaagtg gccaaaattt taanttncaa canannngnn    360

ncagntttna tggatctntn nnnnnncttc nnntnn                              396


<210> SEQ ID NO 26
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 26

gacgctcccc cctccccccg agcgccgctc cggctgcacc gcgctcgctc cgagtttcag     60

gctcgtgcta agctagcgcc gtcgtcgtct cccttcagtc gccatcatga ttatctaccg    120

ggacctcatc agccacgatg agatgttctc cgacatctac aagatccggg agatcgcgga    180

cgggttgtgc ctggaggtgg aggggaagat ggtcagtagg acagaaggta acattgatga    240

ctcgctcatt ggtggaaatg cctccgctga aggccccgag ggcgaaggta cccgaaagca    300

cagtaatcac tgnngncnat nttgtcatga accatcacct gcnngaaaca annttnacaa    360

aanaancctn cnnnnannnc ctnnnnnatt ncnnnn                              396


<210> SEQ ID NO 27
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 27

tttttttttt tttttttttt tttttttttt tttttttttt tggctaaant ttatgtatac     60

nggttnttca aangnggggg aggggggggg gcatccatnt anncncncca ggtttatggn    120

gggntnttnt actattanna nttttcnctt caaancnaag gnttntcaaa tcatnaaaat    180

tattaanatt ncngctgnta aaaaaangaa tgaaccnncn nanganagga nntttcatgg    240

ggggnatgca tcggggnann ccnaanaacc ncggggccat tcccganagg cccaaaaaat    300

gtttnnnnaa aaagggtaaa nttaccccn tnaantttat annnnaaann nnannnnagc    360

ccaannnttn nnnnnnnnnn nnnccnnnna nnnnnn                              396


<210> SEQ ID NO 28
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 28

cgaccttttt tttttttttt atagatgaaa gagggtttat ttattaatat atgatagcct     60
```

-continued

```
tggctcaaaa aagacaaatg agggctcaaa aaggaattac agtaacttta aaaaatatat    120

taaacatatc caagatccta aatatattat tctccccaaa agctagctgc ttccaaactt    180

gatttgatat tttgcatgtt ttccctacgt tgcttggtaa atatatttgc ttctcctttc    240

tgcaatcgac gtctgacagc tgatttttgc tgttttgnca acntgacgtt tcaccttntg    300

tttcaccant tctggaggaa ttgttnaaca ncttacanca ctgccttgaa naaannnnan    360

gcctcaaaag ntcttgnnct atnctnnttc ntnnnt                              396


<210> SEQ ID NO 29
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 29

gacttgctca tttagagttt gcaggaggct ccatactagg ttcagtctga aagaaatctc     60

ctaatggtgc tatagagagg gaggtaacag aaagactctt ttagggcatt tttctgactc    120

atgaaaagag cacagaaaag gatgtttggc aatttgtctt ttaagtctta accttgctaa    180

tgtgaatact gggaaagtga ttttttttctc actcgttttt gttgctccat tgtaaagggc    240

ggaggtcagt cttagtggcc ttgagagttg cttttggcat ttaaatattc taagagaatt    300

aactgtattt cctgtcacct attcactant gcangaaata tacttgctcc aaataagtca    360

ntatgagaag tcactgtcaa tgaaanttgn tttgtt                              396


<210> SEQ ID NO 30
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 30

tttttttttt ttttttttg aaatttanaa acaaatttta tttaagatct gaaatacaat     60

tcctaaaata tcaacttttc canaaaaccg tggctacaca ataatgcatt gcctctatca    120

tgttanaacg tgcattanac tcaaatacaa aaaccatgaa acaaatcacc atccttcaac    180

aatttgagca aagatagaat gcctaagaac aacatagatg gacttgcaga ggatgggctg    240

ttttacttca agcnccataa aaaaaaaaaa gagcncaaat gcattgggtt ttcaggtnta    300

tacattaagn ngaacctttg gcactaggaa tcagggcgtt ttgtcacata gcnttaacac    360

atnttaaaaa attntgtant gtcaaaggga tangaa                              396


<210> SEQ ID NO 31
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 31

gacgggccag ggccatctgg aaagggaact cggcttttcc agaacgtggt ggatcatctg     60
```

-continued

```
tcgggtgtgt ggtgaacacg ttcagttcat cagggcctac gctccgggaa ggggccccca    120

gctgtggctc tgccatgccg ggctgtgttt gcagctgtcc gagtctccat ccgcctttag    180

aaaaccagcc acttcttttc ataagcactg acagggccca gcccacagcc acaggtgcga    240

tcagtgcctc acgcaggcaa atgcactgaa acccaggggc acacncncgc agagtgaaca    300

gtgagttccc ccgacagccc acgacagcca ggactgccct ccccaccccn ccccgacccc    360

angancacgg cacacanntc ancctctnan ctngct                              396
```

<210> SEQ ID NO 32
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 32

```
cgactggcct cataccttgt ctacacagtc cctgcacagg gttcctaacc tgtggttagt     60

aaagaatgtc actttctaac aggtctggaa gctccgagtt tatcttggga actcaagagg    120

agaggatcac ccagttcaca ggtatttgag gatacaaacc cattgctggg ctcggcttta    180

aaagtcttat ctgaaattcc ttgtgaaaca gagtttcatc aaagccaatc caaaaggcct    240

atgtaaaaat aaccattctt gctgcacttt atgcaaataa tcaggccaaa tataagacta    300

cagtttattt acaatttgtt tttaccaaaa atgaggacta nagagaaaaa tggtgctcca    360

aagcttatca tacatttgtc attaagtcct agtctc                              396
```

<210> SEQ ID NO 33
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 33

```
cctttttttt tttttttttt tttttttttt tttttttttt tttttttttt tttttttttt     60

tttttttttt tttttttttt tttttttttt tttttttttt tttttttttt tttttttttt    120

nngnnntntn nnnnannaaa aaaaaaaaaa aannnnnnna aaaaaaannn nnnnnnnnnt    180

tttnnggggg gnttttnann gnannttnnn nttnnnnnaa anccccnnng ggnngggggg    240

nntnnnnnng gnaaaaaaan nnnnngggn cnnnngggnc cncncccnan nnnnaaaann    300

nnnggntttt ttnnttttna aaaaaanngn nnnnnaacaa aantttttnn nnaanttttn    360

gggggaaann ncccntttnt ttttttnnan nnnnnn                              396
```

<210> SEQ ID NO 34
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 34

```
acggaccnag ctggaggagc tgggtgtggg gtgcgttggg ctggtgggga ggcctagttn     60

gggtgcaagt angtctgatt gagcttgtgt tgtgctgaag ggacagccct gggtctaggg    120
```

-continued ganagagncc ctgagtgtga gacccacctt ccccngtccc agcccctccc anttccccca 180
gggacggcca cttcctgntc cccgacncaa ccatggctga agaacaaccg caggtcgaat 240
tgttcntgaa ggctggcagt gatggggcca agattgggaa ctgcccattc tcccacagac 300
tgttnatggt actgtggctc aaggnagtca ccttcaatgt taccaccnnt gacaccaaaa 360
ggcggaccna nacagtgcan aagctgtgcc canngg 396

<210> SEQ ID NO 35
<211> LENGTH: 396
<212> TYPE: DNA
<213> ORGANISM: Homo sapien

<400> SEQUENCE: 35
tcgaccaaaa tcaaatctgg cactcacaag ccctggccga cccccaatgg gttttaccac 60
tccccctcta gaccctgtct tgcaaaatcc tctccctagc cagctagtat tttctgggct 120
aaagactgta caaccagttc ctccatttta tagaagttta ctcactccag gggaaatggt 180
gagtcctcca acctcccttt caaccagtcc catcattcca accagtggta ccatagagca 240
gcaccccccg ccaccctctg agccagtagt gccagcagtg atgatggcca cccatgagcc 300
cagtgctgac ctggcaccca agaaaaagcc caggaagtca agcatgcctg tgaagattga 360
gaaggaaatt attgataccg ccgatgagtt tgatga 396

<210> SEQ ID NO 36
<211> LENGTH: 396
<212> TYPE: DNA
<213> ORGANISM: Homo sapien

<400> SEQUENCE: 36
tcgacgggaa gagcctgcta cggtggactg tgagactcag tgcactgtcc tcctcccagc 60
gaccccacgc tggaccccct gccggaccct ccacccttcg gcccccaagc ttcccagggg 120
cttcctttgg actggactgt ccctgctcat ccattctcct gccaccccca gacctcctca 180
gctccaggtt gccacctcct ctcgccagag tgatgaggtc ccggcttctg ctctccgtgg 240
cccatctgcc cacaattcgg gagaccacgg aggagatgct gcttgggggt cctggacagg 300
agcccccacc ctctcctagc ctggatgact acgtgaggtc tatatctcga ctggcacagc 360
ccacctctgt gctggacaag gccacggccc agggcc 396

<210> SEQ ID NO 37
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 37
cgacggtgtc agcaactggc catgccacag cacataaaga ttacagtgac aagaaaaaca 60
ttgtttgagg attcctttca acagataatg agcttcagtc cccaagatct gcgaagacgt 120
ttgtgggtga tttttccagg agaagaaggt ttagattatg gaggtgtagc aagagaatgg 180
ttctttcttt tgtcacatga agtgttgaac ccaatgtatt gcctgtttga atatgcaggg 240
aaggataact actgcttgca gataaacccc gcttcttaca tcaatccaga tcacctgaaa 300
tattttcgtt ttattggcag atttattgcc atggctctgt tccatgggaa aattcataga 360

-continued

```
cacgggtttt tctttnccat tctataagcg tatctt                          396


<210> SEQ ID NO 38
<211> LENGTH: 396
<212> TYPE: DNA
<213> ORGANISM: Homo sapien

<400> SEQUENCE: 38

cgaccaaaat gataaatagc tttaagaatg tgctaatgat aaatgattac atgtcaattt     60

aatgtactta atgtttaata ccttatttga ataattacct gaagaatata ttttttagta    120

ctgcatttca ttgattctaa gttgcacttt ttacccccat actgttaaca tatctgaaat    180

cagaatgtgt cttacaatca gtgatcgttt aacattgtga caaagtttaa tggacagttt    240

tttcccatat gtatatataa aataatgtgt tttacaatca gtggcttaga ttcagtgaaa    300

tacagtaatt cattcaatta tgatagtatc tttacagaca ttttaaaaat aagttatttt    360

tatatgctaa tattctatgt tcaagtggaa tttgga                          396


<210> SEQ ID NO 39
<211> LENGTH: 396
<212> TYPE: DNA
<213> ORGANISM: Homo sapien

<400> SEQUENCE: 39

tcgaccaaga atagatgctg actgtactcc tcccaggcgc cccttccccc tccaatccca     60

ccaaccctca gagccacccc taaagagata ctttgatatt ttcaacgcag ccctgctttg    120

ggctgccctg gtgctgccac acttcaggct cttctccttt cacaaccttc tgtggctcac    180

agaacccttg gagccaatgg agactgtctc aagagggcac tggtggcccg acagcctggc    240

acagggcaag tgggacaggg catggccagg tggccactcc agacccctgg cttttcactg    300

ctggctgcct tagaaccttt cttacattag cagtttgctt tgtatgcact ttgttttttt    360

ctttgggtct tgtttttttt ttccacttag aaattg                          396


<210> SEQ ID NO 40
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 40

tttttttttt ttttgttatt tagtttttat ttcataatca taaacttaac tctgcaatcc     60

agctaggcat gggagggaac aaggaaaaca tggaacccaa agggaactgc agcgagagca    120

caaagattct aggatactgc gagcaaatgg ggtggagggg tgctctcctg agctacagaa    180

ggaatgatct ggtggttaan ataaaacaca agtcaaactt attcgagttg tccacagtca    240

gcaatggtga tcttcttgct ggtcttgcca ttcctggacc caaagcgctc catggcctcc    300

acaatattca tgccttcttt cactttgcca aacaccacat gcttgccatc caaccactca    360

gtcttggcag tgcanatgaa aaactgggaa ccattt                          396


<210> SEQ ID NO 41
<211> LENGTH: 396
<212> TYPE: DNA
<213> ORGANISM: Homo sapien
<220> FEATURE:
<221> NAME/KEY: misc_feature
```

-continued

<222> LOCATION: (1)...(396)
<223> OTHER INFORMATION: n = A,T,C or G

<400> SEQUENCE: 41
tcgacctctt gtgtagtcac ttctgattct gacaatcaat caatcaatgg cctagagcac 60
tgactgttaa cacaaacgtc actagcaaag tagcaacagc tttaagtcta aatacaaagc 120
tgttctgtgt gagaattttt taaaaggcta cttgtataat aacccttgtc atttttaatg 180
tacaaaacgc tattaagtgg cttagaattt gaacatttgt ggtctttatt tactttgctt 240
cgtgtgtggg caaagcaaca tcttccctaa atatatatta cccaaagnaa aagcaagaag 300
ccagattagg tttttgacaa aacaaacagg ccaaaagggg gctgacctgg agcagagcat 360
ggtgagaggc aaggcatgag agggcaagtt tgttgt 396

<210> SEQ ID NO 42
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 42
cttttttttt tttttttttt tttttttttt tttttttttt tttttttttt tttttttttt 60
aaaanccnna nnaananang gnaannnann aaaaaannca aaccncntnt anaaaangcc 120
nntntnaggg gggggttca aaaccaaang gnngntngga ngnaaannna aaanttnnnn 180
gggggnanaa anaaaaaggg nngaaanntg acccnanaan gaccngaaan cccgggaaac 240
cnngggntan aaaaaaagnt gancccctaaa nncccccgna aaangggga agggnaannc 300 caaatccnnt gngggttggg ggnggggaaa aaaaaaaccc cnaaaaantg naaaaaaccg 360
ggnttnaaan atttgggttc gggggntttn tnttaa 396

<210> SEQ ID NO 43
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 43
tttttttttt ttttgcttca ctgctttatt tttgaaatca caagcaattc aaagtgatca 60
tcattgaggc ttctgttaaa agttcttcca aagttgccca gttttaanat taaacaatat 120
tgcactttaa gatgaactaa cttttgggat tctcttcaaa gaaggaaagt attgctccat 180
ctgtgctttt cttanactaa aagcatactg canaaaactc tattttaaaa atcaacactg 240
cagggtacag taacatagta aagtacctgc ctattttana atcctanaga acatttcatt 300
gtaagaaact agcccattat ttaagtgtcc acagtatttt tcatttcant ggtccaagat 360
gccaaggttt ccaaacacaa tcttgttctc taatac 396

<210> SEQ ID NO 44
<211> LENGTH: 396
<212> TYPE: DNA
<213> ORGANISM: Homo sapien

<400> SEQUENCE: 44

-continued

```
gacctagttt tacctcttaa atatctctgt tcccttctaa gttgtttgct gtgttttctt     60

cagagcaaga aggttatatt ttttaaaatt tacttagtaa tgcacattca aaacacacat    120

caagtcttca ggataaagtt caaaaccgct gtcatggccc catgtgatct ctccctcccc    180

taccccctcta tcatttagtt tcttctgcgc aagccactct ggcttccttt cagttttgtg    240

gttcccgttt ttagctagtt cagtggtttt caatgggcat ttcttgcctt tttttttcta    300

aacgacaaat agaaatacat cttctttatt atcctccaaa tccaattcag aggtaatatg    360

ctccacctac acacaatttt agaaataaat taaaaa                              396
```

<210> SEQ ID NO 45
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 45

```
tttttttttt ttttaaannt tntaaatttt taatgaaann ganttagaac aatgtattat     60

tnacatgtaa ataaaaaaag agancataan ccccatatnc tcnnnaaagg aaggganacn    120

gcnggccntt tatnagaana nnnnncatat aagaccccat taagaagaat ctggatctaa    180

anacttncaa acaggagttc acagtangtg aacagcannc cctaatccca ctgatgtgat    240

gnttcanata aaatcancan cgntgatcgg gnatcnnanc aatntgancg gaanannact    300

gctcnatatn tttnaggann cngatgtggt catttttttac aaagataatg gccacaccct    360

tccngnccga atcgancnga nctcccnntt ctgtgn                              396
```

<210> SEQ ID NO 46
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 46

```
tttttttttt tttttttttc tganacagag tctcattctg ttgcctaggc tggattgcag     60

tggtgccatc tcggctcact gcaacctccg cctcctgggt tccanaaatt ctcctgcctc    120

agcctcccgg gtagctggga ctanaggcac acgccaccac gccaggctaa tttttatatt    180

tttagtanan atggcgtttc accatgttga ccanactgat ctcgaactcc cgacctcgtg    240

atccacccac ctcggcctcc caaagtgctg ggattacagg cgtgaaacca ccaggcccgg    300

cctgaaatat ctatttnttt tcagattatt tttaaaattc catttgatga atcttttaaa    360

gtgagctana naaagtgngt gtgtacatgc acacac                              396
```

<210> SEQ ID NO 47
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 47

```
tttttttttt tttttttgct gttgccaact gtttattcag ggccctgaac gggtggtgcg     60
```

-continued

```
tggacatgca acacactcgg gcccacagca gcgtgaccgg ccgctcccaa gccccgggcg    120

cacaaccaca gccaggagca gcccctgcca ccactgggcc accgtccagg gccccacagg    180

accagccgaa ggtgccccgg gccgaggcca gctgggtcag gtgtacccct agcctggggt    240

tgagtgagga gcggcacccc cagtatcctg tgtaccccaa gttgcccagn aggccgaggg    300

ggccttgggc tccatctgca ctggccaccc cgtgccaagc atcacagctg cgtgagcagg    360

tttgtgtgtg agcgtgtggc ggggcctggt tgtccc                              396


<210> SEQ ID NO 48
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 48

ctgggcctgt gccgaagggt ctgggcagat cttccaaaga tgtacaaaat gtagaaattg     60

ccctcaagca aatgcaaaga tgctcaacac ccttagtcat caagaaaatg caaatggaat    120

ccacagagag atactgcaca ctgacaaaga tggtcgtatt actaaaggtg aataaccagc    180

gcggggggca cgtggagtca ctggaacatt tgtgcaatgc tggtgggaat gtcaacccgt    240

gcggccctct ggaataagcc tggcagctcc tccaagagtt acccgtgtga cccagcaatt    300

ccactcctag ctccacccac aggaattgaa agcaaagacg caaacagatg cctgtgcacc    360

aaagttcacg gcagcatcct tcgccatagt ggnaan                              396


<210> SEQ ID NO 49
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 49

accccaaaat gggaaaggaa aagactcata tnaacattgn cgtnattgga cacgtacatt     60

cggncaagtn caccactact ggncatntga tntataaatg cggnggcatc gacanaanaa    120

ccatngnaan atttganaag gaggctgctg atatnggaaa gggctccntc nantntgcct    180

gggtcttgga tnaactgaaa nctgancntg aacgtggnnt caccattgat atctncttgt    240

ggaaatntna gaccancann tactatgtna ctatcattga tgccccagga cacaganact    300

ttatcnaaan catgattacn nggacatnta nagctgactg tgctngcctg attgtngctg    360

ctggtgttgg tgaatttgaa nctggtatnt ccaana                              396


<210> SEQ ID NO 50
<211> LENGTH: 396
<212> TYPE: DNA
<213> ORGANISM: Homo sapien

<400> SEQUENCE: 50

cgacttcttg ctggtgggtg gggcagtttg gtttagtgtt atactttggt ctaagtattt     60

gagttaaact gctttttttgc taatgagtgg gctggttgtt agcaggtttg tttttcctgc    120

tgttgattgt tactagtggc attaactttt agaatttggg ctggtgagat taattttttt    180
```

-continued

```
taatatccca gctagagata tggcctttaa ctgacctaaa gaggtgtgtt gtgatttaat    240

tttttcccgt tccttttttct tcagtaaacc caacaatagt ctaaccttaa aaattgagtt    300

gatgtcctta taggtcacta cccctaaata aacctgaagc aggtgttttc tcttggacat    360

actaaaaaat acctaaaagg aagcttagat gggctg                              396


<210> SEQ ID NO 51
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 51

tttttttttt ttcagcgngg atttatttta tttcattttt tactctcaag anaaagaana     60

gttactattg caggaacaga cattttttta aaaagcgaaa ctcctgacac ccttaaaaca    120

gaaaacattg ttattcacat aataatgngg ggctctgtct ctgccgacag gggctgggtt    180

cgggcattag ctgtgccgtc gacaatagcc ccattcaccc cattcataaa tgctgctgct    240

acaggaaggg aacagcggct ctcccanaga gggatccacc ctggaacacg agtcacctcc    300

aaagagctgc gactgtttga naatctgcca anaggaaaac cactcaatgg gacctggata    360

acccaggccc gggagtcata gcaggatgtg gtactt                              396


<210> SEQ ID NO 52
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 52

acctcgctaa gtgttcgcta cgcggggcta ccggatcggt cggaaatggc agaggtggag     60

gagacactga agcgactgca nagccagaag ggagtgcagg gaatcatcgt cgtgaacaca    120

gaaggcattc ccatcaagag caccatggac aaccccacca ccacccagta tgccagcctc    180

atgcacagnt tcatcctgaa ggcacggagc accgtgcgtg acatcgaccc ccagaacgat    240

ctcaccttcc ttcgaattcg ctccaagaaa aatgaaatta tggttgcacc agataaagac    300

tatttcctga ttgtgattca gaatccaacc gaataagcca ctctcttggc tccctgtgtc    360

attccttaat ttaatgcccc ccaagaatgt taatgt                              396


<210> SEQ ID NO 53
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 53

tttttttttt tttttttttt tttttttttt tttttttttt tttttttttt tttttttttt     60

tttttttttt tttttttttt tttttttttt tttttttttt tttttttttt tttttttttt    120

tttttttttt tttttttttt tttttttttt tttttttttt tttttttttt tttttttttt    180

tttttttttt tttttttttt tttttttttt tttttttttt ttannttntt ttttnttttn    240
```

-continued cctttntttt aattcanaaa aagaanaaga aaanataana nnnancnnan nnnnnnnatn 300
ntncttnata ntnnttnnnn nanngggnnn gcgagnnnnn nnnnnnnnnn nntctnnnnt 360
tnnnnnnctt gcnccccttn nnttngnnnn angcaa 396

<210> SEQ ID NO 54
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 54
ctcttggggc tgctgggact cgcgtcggtt ggcgactccc ggacgtaggt agtttgttgg 60
gccgggttct gaggccttgc ttctctttac ttttccactc taggccacga tgccgcagta 120
ccagacctgg gaggagttca gccgcgctgc cgagaagctt tacctcgctg accctatgaa 180
ggcacgtgtg gttctcaaat ataggcattc tgatgggaac ttgtgtgtta aagtaacaga 240
tgatttagtt tgtttggtgt ataaaacaga ccaagctcaa gatgtaaaga agattgagaa 300
attccacagt caactaatgc gacttatggt agccaaggaa gcccgcaatg ttaccatgga 360
aactgantga atggtttgaa atgaagactt tgtcgt 396

<210> SEQ ID NO 55
<211> LENGTH: 396
<212> TYPE: DNA
<213> ORGANISM: Homo sapien

<400> SEQUENCE: 55
cgacggtttg ccgccagaac acaggtgtcg tgaaaactac ccctaaaagc caaaatggga 60
aaggaaaaga ctcatatcaa cattgtcgtc attggacacg tagattcggg caagtccacc 120
actactggcc atctgatcta taaatgcggt ggcatcgaca aaagaaccat tgaaaaattt 180
gagaaggagg ctgctgagat gggaaagggc tccttcaagt atgcctgggt cttggataaa 240
ctgaaagctg agcgtgaacg tggtatcacc attgatatct ccttgtggaa atttgagacc 300
agcaagtact atgtgactat cattgatgcc ccaggacaca gagactttat caaaaacatg 360
attacaggga catctcaggc tgactgtgct gtcctg 396

<210> SEQ ID NO 56
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 56
tttttttttt ttttttctca tttaactttt ttaatgggtc tcaaaattct gtgacaaatt 60
tttggtcaag ttgtttccat taaaaagtac tgattttaaa aactaataac ttaaaactgc 120
cacacgcaaa aaanaaaacc aaagnggtcc acaaaacatt ctcctttcct tctgaaggtt 180
ttacgatgca ttgttatcat taaccagtct tttactacta aacttaaatg gccaattgaa 240
acaaacagtt ctganaccgt tcttccacca ctgattaana gtggggtggc aggtattagg 300
gataatattc atttagcctt ctgagctttc tgggcanact tggngacctt gccagctcca 360

-continued

```
gcagccttnt tgtccactgc tttgatgaca cccacc                              396


<210> SEQ ID NO 57
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 57

cctttttttt tttttttttt tttttttttt tttttttttt tttttttttt tnaaaanntt     60

ntttttgcaa anccnancaa aaanggnngg aangaaaaan nggaaaaatt ntttttncnt    120

ntttgggaac nnnnagccct tnntttgaaa aaangnggnc ttaaaanngn tgaannaaag    180

gnnannccn gntncttnnn tttaaaaana anggggnngn tttttttaa anaanatttt     240

ttttttccct aanancnncn anntgaaacn ngncccnacn nctnncttna aagggnnnaa    300

atnanangnn aaaaaanccc tnancccccc cccttannt tncnannana naaagncntt     360

ttgggncntg naaaaanaan cctttttnnt gcnttn                              396


<210> SEQ ID NO 58
<211> LENGTH: 396
<212> TYPE: DNA
<213> ORGANISM: Homo sapien

<400> SEQUENCE: 58

cgacctcaaa tatgccttat tttgcacaaa agactgccaa ggacatgacc agcagctggc     60

tacagcctcg atttatattt ctgtttgtgg tgaactgatt ttttttaaac caaagtttag    120

aaagaggttt ttgaaatgcc tatggtttct ttgaatggta aacttgagca tcttttcact    180

ttccagtagt cagcaaagag cagtttgaat tttcttgtcg cttcctatca aaatattcag    240

agactcgagc acagcaccca gacttcatgc gcccgtggaa tgctcaccac atgttggtcg    300

aagcggccga ccactgactt tgtgacttag gcggctgtgt tgcctatgta gagaacacgc    360

ttcacccccca ctccccgtac agtgcgcaca ggcttt                             396


<210> SEQ ID NO 59
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 59

cttttttttt tttttttttt tcagnggaaa ataactttta ttganacccc accaactgca     60

aaatctgttc ctggcattaa gctccttctt cctttgcaat tcggtctttc ttcagnggtc    120

ccatgaatgc tttcttctcc tccatggtct ggaagcggcc atggccaaac ttggaggngg    180

tgtcaatgaa cttaaggnca atcttctcca nagcccgccg cttcntctgc accancaagg    240

acttgcggag ggngagcacc cgcttnttgg ttcccaccac ncagcctttc agcatgacaa    300

agtcattggt cacttcacca tagnggacaa agccacccaa agggttgatg ctccttggca    360

aataggncat agtcacngga ggcattgtnc ttgatc                              396


<210> SEQ ID NO 60
<211> LENGTH: 396
```

-continued

<212> TYPE: DNA
<213> ORGANISM: Homo sapien

<400> SEQUENCE: 60
acctcagctc tcggcgcacg gcccagcttc cttcaaaatg tctactgttc acgaaatcct 60
gtgcaagctc agcttggagg gtgatcactc tacaccccca agtgcatatg ggtctgtcaa 120
agcctatact aactttgatg ctgagcggga tgctttgaac attgaaacag ccatcaagac 180
caaaggtgtg gatgaggtca ccattgtcaa cattttgacc aaccgcagca atgcacagag 240
acaggatatt gccttcgcct accagagaag gaccaaaaag gaacttgcat cagcactgaa 300
gtcagcctta tctggccacc tggagacggt gattttgggc ctattgaaga cacctgctca 360
gtatgacgct tctgagctaa aagcttccat gaaggg 396

<210> SEQ ID NO 61
<211> LENGTH: 396
<212> TYPE: DNA
<213> ORGANISM: Homo sapien

<400> SEQUENCE: 61
tagcttgtcg gggacggtaa ccgggacccg gtgtctgctc ctgtcgcctt cgcctcctaa 60
tccctagcca ctatgcgtga gtgcatctcc atccacgttg gccaggctgg tgtccagatt 120
ggcaatgcct gctgggagct ctactgcctg gaacacggca tccagcccga tggccagatg 180
ccaagtgaca agaccattgg gggaggagat gactccttca acaccttctt cagtgagacg 240
ggcgctggca agcacgtgcc ccgggctgtg tttgtagact tggaacccac agtcattgat 300
gaagttcgca ctggcaccta ccgccagctc ttccaccctg agcagctcat cacaggcaag 360
gaagatgctg ccaataacta tgcccgaggg cactac 396

<210> SEQ ID NO 62
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 62
tcgacgtttc ctaaagaaaa ccactctttg atcatggctc tctctgccag aattgtgtgc 60
actctgtaac atctttgtgg tagtcctgtt ttcctaataa ctttgttact gtgctgtgaa 120
agattacaga tttgaacatg tagtgtacgt gctgttgagt tgtgaactgg tgggccgtat 180
gtaacagctg accaacgtga agatactggt acttgatagc ctcttaagga aaatttgctt 240
ccaaatttta agctggaaag ncactggant aactttaaaa aagaattaca atacatggct 300
ttttagaatt tcnttacgta tgttaagatt tgngtacaaa ttgaantgtc tgtnctganc 360
ctcaaccaat aaaatctcag tttatgaaan aaannn 396

<210> SEQ ID NO 63
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 63

-continued

```
ttnttttttt nttttntntt ttntcnttgn ttgnacngaa cccggcgctn nttccccacn     60

nnnnacggcc gcccntattc annnntncnt canntannna ccgcaccctc ggactgcnnn    120

tngggccccg ccgncnannc nccnncnccc anttcnccgc cgccgccgcc gccttttttt    180

attggcnncc atnanaaccg gggncacctc ncangngcgc cnaaantngg ggcangactc    240

anagggggcc atcaaccncc aagnncaanc tgganctcta caaacggcct acgntttntg    300

nccatgnggg tagggnttta cccgcnatga tgannatgnn aanaactttn ncaanccctt    360

tattaaccaa tgnggtgngg agacggaacn tggtta                              396
```

```
<210> SEQ ID NO 64
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 64

tcgacgtcgg ggtttcctgc ttcaacagtg cttggacgga acccggcgct cgttccccac     60

cccggccggc cgcccatagc cagccctccg tcacctcttc accgcaccct cggactgccc    120

caaggccccc gccgccgctc cagcgccgcg cagccaccgc cgccgccgcc gcctntnctt    180

agtcgccgcc atgacgaccg cgtccacctc gcaggtgcgc cagaactacc accaggactc    240

agaggccgcc atcaaccgcc agatcaacct ggagctctac gcctcctacg tttacctgtc    300

catgtcttac tactttgacc gcgatgatgt ggctttgaan aactttgcca aatactttct    360

tcccaatctc atgaggagaa ggaacatgct ganaaa                              396
```

```
<210> SEQ ID NO 65
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 65

tttttttttt tttttttttt tttttnacca ataatgcttt tattttccac atcaanatta     60

atttatatgt tagttttagt acaagtacta aaatgtatac ttnttgccct aatagctaag    120

gnatacataa gcttcaccat acatnttgca nccncctgtc tgtcctatgt cattgttata    180

aatgtanana ttttaggaaa ctnttttatt caacctggga catntatact gtaggagtta    240

gcactgacct gatgtnttat ttaaaagtaa tgnatattac ctttacatat attccttata    300

tattnaaacg tatttccatg ttatccagct taaaatcaca tggnggttaa aagcatgagt    360

tctgagtcaa atctggactg aaatcctgat gctccc                              396
```

```
<210> SEQ ID NO 66
<211> LENGTH: 396
<212> TYPE: DNA
<213> ORGANISM: Homo sapien

<400> SEQUENCE: 66

tcgacttttt tttttccagg acattgtcat aattttttat tatgtatcaa attgtcttca     60

atataagtta caacttgatt aaagttgata gacatttgta tctatttaaa gacaaaaaaa    120

ttcttttatg tacaatatct tgtctagagt ctagcaaata tagtaccttt cattgcagga    180
```

-continued tttctgctta atataacaag caaaaacaaa caactgaaaa aatataaacc aaagcaaacc 240
aaaccccccg ctcaactaca aatgtcaata ttgaatgaag cattaaaaga caaacataaa 300
gtaacttcag cttttatcta gcaatgcaga atgaatacta aaattagtgg caaaaaaaca 360
aacaacaaac aacaaacaaa acaaaacaaa caaaca 396

<210> SEQ ID NO 67
<211> LENGTH: 396
<212> TYPE: DNA
<213> ORGANISM: Homo sapien

<400> SEQUENCE: 67
acgcttttgt ccttcatttt aactgttatg tcatactgtt atgttgacat atttctttat 60
aagagaatag aggcaaaagt atagaactga ggatcatttg tatttttgag ttggaaatta 120
tgaaacttca ccatattatg atcatacata ttttgaagaa cagactgacc aaagctcacc 180
tgttttttgt gttaggtgct ttggctgaac ttgattccag ccccctttc cctttggtgt 240 tgtgtatgtc tcttcatttc ctctcaaatc ttcaactctt gccccatgtc tccttggcag 300
caggatgctg gcatctgtgt agtcctcata ctgtttactg ataacccaca aattcatttt 360
catggcagac ctaagctcag accctgcctt gtcctg 396

<210> SEQ ID NO 68
<211> LENGTH: 396
<212> TYPE: DNA
<213> ORGANISM: Homo sapien

<400> SEQUENCE: 68
acctgagtcc tgtcctttct ctctccccgg acagcatgag cttcaccact cgctccacct 60
tctccaccaa ctaccggtcc ctgggctctg tccaggcgcc cagctacggc gcccggccgg 120
tcagcagcgc ggccagcgtc tatgcaggcg ctgggggctc tggttcccgg atctccgtgt 180
cccgctccac cagcttcagg ggcggcatgg ggtccggggg cctggccacc gggatagccg 240
ggggtctggc aggaatggga ggcatccaga acgagaagga gaccatgcaa agcctgaacg 300
accgcctggc ctcttacctg gacagagtga ggagcctgga gaccgagaac cggaggctgg 360
agagcaaaat ccgggagcac ttggagaaga agggac 396

<210> SEQ ID NO 69
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 69
ntcncngnng ntgtggtnnt ttttttaatt tttatntttt cttttttttt ctngctagcn 60 cttnctttt ttggaattnc ggtnccttt tntntcnatt ttttngacaa aaanaacctn 120
ttntttnana ccanagnnng gnncacncnt nnaatntncc ccttttncgn tngggagctn 180
cncnttnnnc gccnacntca ntcgagacng tnctttttnnn tnnancannn tnngtncgtt 240
gncngcnttn ntncannant nttccctatn nacntgnnnt cncncatnnt tggacnancn 300
cctagccttn ccatnntttn nttntttntn natnancctn gaaaacntcn gnntnttcnc 360
nncnttnccn cncncncctt cntatgtncn atgncn 396

<210> SEQ ID NO 70
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 70
tttttttttt ttttnttttt tttttttttt ttttttttntt tttttttttt ttttttntnc 60
aannnntnaa cttttaanng gccnccngcn ccccaanggg gaccctgctt ttgnnggcta 120
aatgccnnaa aactttgggg nantnggtat naaaccccnc tttgcccnnc annttncngg 180
gggggggggg tttttgnngg ggaacangna naacnttttn ncnanggnat caccaaaaan 240
aaagcccnnc cctttttccn annggggggg ggngggggga aantcanccc ccanattgac 300
cttnatttca aaanggggct tataatcctg ggcntggann cttccctnta cccgggggtt 360
gnccacnttt tattanaggg gnangnggat ccccnt 396

<210> SEQ ID NO 71
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 71
gcatctagag ggccngttta ntctagaggn ccngnntaaa cnnnnncatc nacctncnnt 60
gcncctgctn gttgccnccc ntctgtgnct tgcnnnnccc nngagcgtnc cttnaccnnn 120
gaangtgcct nnnnnactga nnnnnncnna taanatgngg anantncgtc gncattntnt 180
natnnggggt gatgctattc tggggggtgg ggnggngnna tnnnatactn nggggacgtn 240
nnatnangag nnatntcnng nttntctnnt gntttntggg gggcnatnng nnntctntnn 300
ggactcntcg cncannnatc aatancttna ttcngtgtan ngtccgnccn tagnncngcn 360
ngtactnnan ngttgnnntc attactnttc gtnngg 396

<210> SEQ ID NO 72
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 72
tntttttttt tttctaaaac atnactnttt attnnnnang ntttntgaac ctctnngcnt 60
natggtgaga gtttgtctga ttaataanaa tnggannntt nannanangc ntgnncgcaa 120
ngatggcnnc nctgtatatc ccaccatccc attacactnt gaaccttttn tttgattaat 180
aaaaggaagg natgcgggga angggaaag agaatgcttg aacattncca tgngnccttn 240
gacaaacttt ccaatggagg cnggaacnaa nnaccaccan ncaactcccc tttttgtaat 300
ttnnnaactt ncaacnncta nctntttatt ttggcntccc tggnngaaac agnctgtatn 360
annnnnaagn ccntgagaac atccctggnt nncnna 396

-continued

<210> SEQ ID NO 73
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 73
ntcaacntng actnctgtga ggnatggtgc tgggngcnta tgcngtgngn ttttggatac 60
naccttatgg acantngcnn tcccnnggaa ngatnataat ncttactgna gnnactnnaa 120
nnttccntnt cnaaaangtt naaaancatt ggatgtgcca caatgatgac agtttatttg 180
ctactcttga gtgctataat gatgaagatc ttanccacca ttatcttaac tgangcaccc 240
aanatggtga nttggggaac atatanagta cacctaagtt cacatgaagt tgtttnttcc 300
caggnnctaa agagcaagcc taactcaagc cattgncaca caggtgagac acctctattt 360
tgtacttctc acttttaagg gattagaaaa tagcca 396

<210> SEQ ID NO 74
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 74
cctttttttt tttttttact gngaatatat actttttatt tagtcatttt tgtttacaat 60
tgaaactctg ggaattcaaa attaacatcc ttgcccgtga gcttcttata gacaccanaa 120
aaagtttcaa ccttgtgttc cacattgttc tgctgtgctt tgtccaaatg aacctttatg 180
agccggctgc catctagttt gacgcggatt ctcttgccca caatttcgct tgggaagacc 240
aagtcctcaa ggatggcatc gtgcacagct gtcagagtac ggctcctggg acgcttttgc 300
ttattttttg tacggctttt tcgagttggc ttaggcagaa ttctcctctg agcgataaag 360
acgacatgct tcccactgaa ctttttctcc aattcg 396

<210> SEQ ID NO 75
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 75
tttttttttt tttntttttt tttttttttt tttttttnaa ntntaanggg ganggcccct 60 ttttttttaaa ctngnccntt ttnctttcct tttttnaaaa ggaaaaaaaa anntttnttt 120
ttcnttnaaa aaccctttt cccacnaaca aaaaaaaccn ttccccntnc cttttnnnna 180
aaaaaaaggg gctnggnntt tccccttann caaaaaaccn tntccnnggg naaaaaantt 240
ntcnccgggg gggaaacnnn tgggggtgtn nccnaaattt gggggccntc ggaaggggg 300 nnccncncct aaagangtnt ttcaaaanaa aaacccccnt cctnttntaa aaanaaaana 360
aaanaangnn ngnntttttt ntcnttnncc ccccaa 396

<210> SEQ ID NO 76

-continued

<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 76
acattcttca gaaatacagt gatgaaaatt cattttgaaa ctcaaatatt ttcattttgg 60
atattctcct gtttttatta aaccagngat tacncctggc cntccctnta aatgttctag 120
gaaggcatgt ctgttgtnnt ttnnnnaaaa nnaaattntt tttttttngn naaaccccaa 180
atcccanttt atcaggaagt tagncnaatg aaatggaaat tggntaatgg acaaaagcta 240
gcttgtaaaa aggaccaccc nnccacnngn ctttaccccc ttggttngtt gggggaaaaa 300
ccatnnttaa ccntntggnn aaaattgggn ncntaaagtt tncntggnna acagtncntn 360
cngtattnaa ttgncnttat nggaaaatcn gggatt 396

<210> SEQ ID NO 77
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 77
tttttttttt tttttttttt tttttttttt tatcaacatt tatatgcttt attgaaagtt 60
ganaanggca acagttaaat ncngggacnc cttacaattg tgtaaanaac atgcncanaa 120
acatatgcat ataactacta tacaggngat ntgcaaaaac ccctactggg aaatccattt 180
cattagttan aactgagcat ttttcaaagt attcaaccag ctcaattgaa anacttcagt 240
gaacaaggat ttacttcagc gtattcagca gctanatttc aaattacnca aagngagtaa 300
ctgngccaaa ttcttaaaat ttntttaggg gnggtttttg gcatgtacca gtttttatgt 360
aaatctatnt ataaaagtcc acacctcctc anacag 396

<210> SEQ ID NO 78
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 78
agctggcnaa aggngnatgn gctgcnangc gattangnnn ggtaacgtca nnggntnncc 60
agtgcangac nttgtaaaac gacggccaca tgaattgtaa tacgactcac tatngggcgn 120
attgggccgt gnaggatngt gntcacactc gaatgtatnc tggcngatnc ananngcttt 180
atngctnttg acggngnntn anccanctng ggctttaggg ggtatcccct cgcccctgct 240
tcnttgattt gcacgggcnn ctccganttc cttcataata ccngacgctt cnatccccta 300
gctcngacct ntcantntnt tcnntgggtt ntnnccgntc acngcttncc cgnangntat 360
aatctnggct cctttnggga tccattantc tttact 396

<210> SEQ ID NO 79
<211> LENGTH: 396

-continued

<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 79
caccaaccaa aacctggcgc cgttggcatc gtagagtgaa cacaacccaa aaacgatacg 60
ccatctgttc tgccctggct gcctcagccc taccagcact ggtcatgtct aaaggncatc 120
gtattgagga agttcctgaa cttcctttgg tangttgaag ataaagctga aggctacaag 180
aagaccaang aagntgtttt gctccttaan aaacttanac gcctggaatg atatcaaaaa 240
ngctatgcct ctcagcgaat gagactggan angcaaaatg agaaaccntc nccgcatcca 300
gcgnaggggc cgtgcatctc tatnntgang atnntggnan cnttcaaggc cttcagaacc 360
tccctngaaa tnctctnctt taangaacca aactgn 396

<210> SEQ ID NO 80
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 80
tgtacatagg catcttattc actgcaccct gtcacaccca gcaccccccg ccccgcacat 60
tatttgaaag actgggaatt taatggttag ggacagtaaa tctacttctt tttccaggga 120
cgactgtccc ctctaaagtt aaagtcaata caagaaaact gtctattttt agcctaaagt 180
aaaggctgtg aagaaaattc attttacatt gggtagacag taaaaaacaa gtaaaataac 240
ttgacatgag cacctttaga tccttccctt catggggctt tgggcccaga atgacctttg 300
aggcctgtaa anggattgna atttcctata agctgtatag tggagggatt ggngggtcat 360
ttgagtaagc cctccaagat acnttcaata cctggg 396

<210> SEQ ID NO 81
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 81
gcagctgaag ttcagcaggt gctgaatcga ttctcctcgg cccctctcat tccacttcca 60
acccctccca ttattccagt actacctcag caatttgtgc cccctacaaa tgttagagac 120
tgtatacgcc ttcgaggtct tccctatgca gccacaattg aggacatcct gcatttcctg 180
ggggagttcg ccacagatat tcgtactcat ggggttcaca tggttttgaa tcaccagggn 240
ccgccatcag gagatgcctt tatccagatg aagtctgcgg acagancatt tatggctgca 300
cagaagtggc ataaaaaaaa catgaaggac agatatgttg aagttttcag tgtcagctga 360
nganagaaca ttgnngtann ngggggnact ttaaat 396

<210> SEQ ID NO 82
<211> LENGTH: 396
<212> TYPE: DNA

-continued

<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 82
gactcagaaa tgtcagtctc atgaagttca aaagatcgag aatgtttgct atcttggtgg 60
agcagccgca gccaagcaag taacttgtaa aatgaggaat gccatcaccc ctcgagtgtc 120
catcccacat aacttggggt tagagcacaa gcgttcccag gaactactca ccttaccatc 180
ttggccgttt catttgcttc caccagttct ggaaagagan ggcctagaag ttcaaaaaaa 240
aagtaggaaa ngtgcttttg gagaaaatca cctgctcctc agaactgggc ttacaanctg 300
ngaagtacnc tatgtgccac ctaatcctca tatatgacct caagagacnc caataagcat 360
atttccacca cggaatgacc agtgctttgg gtaana 396

<210> SEQ ID NO 83
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 83
tttgatttaa ganatttatt attttttaa aaaaagcaac ttccagggtt gtcattgtac 60
aggttttgcc cagtctccta tagcatggta tagtgataac tgatttttta taacaatgac 120
tcagaggcat tgaagatcca taactatctt ctgaattatc acagaaagaa gaaagttaga 180
agagtttaat gttaagtgta ttaaaaatca tattctaatt cttttaattt ggttatctga 240
gtatgataat ataggagagc tcagataaca aggaaaaggc attggggtaa gaacactcct 300
tcccacagga tggcattaac agactttttc tgcatatgct ttatatagtt gccaactaat 360
tcacctttta cncagcttna ttttttttta ctnggg 396

<210> SEQ ID NO 84
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 84
tttttacagc aatttttttt tattgatgtt taacctgtat acaaccatac ccattttaag 60
ngtacagaca aatgaatttt gacaaattca ttcactcatc taatcatcac tataaccatg 120
atacagattt ttatcactcc aaaagtccat cctgtgctct tttcaagtcc atcctcctca 180
tctgataccc caagccacca ttgttttgct ttctggaact acagttttgg gntttagaa 240 tttcatatat ggtngaatca taccatttgn natttggggc tgacgncttt cctccaataa 300
tggatttgag aattatctac attttgcatg gatcctgggt tatttatacc aacnangggt 360
tattatgnaa aatnggacca caatttggng gcanta 396

<210> SEQ ID NO 85
<211> LENGTH: 396
<212> TYPE: DNA
<213> ORGANISM: Homo sapien -continued
<220> FEATURE:
<221> NAME/KEY: misc_feature
<222> LOCATION: (1)...(396)
<223> OTHER INFORMATION: n = A,T,C or G

<400> SEQUENCE: 85
cagtgaccgt gctcctaccc agctctgctc cacagcgccc acctgtctcc gcccctcggc 60
ccctcgcccg gctttgccta accgccacga tgatgttctc gggcttcaac gcagactacg 120
aggcgtcatc ctcccgctgc agcagcgcgt ccccggccgg ggatagcctc tcttactacc 180
actcacccgc agactccttc tccagcatgg gctcgcctgc aacgcgcagg acttctgcac 240
ggacctggcc gctccagtgc caacttcatt ccacggcact gcatctcgac canccggact 300
tgcannggtt ggggaanccg cccttgtttc tccgtggccc atctaanacc aaacccntca 360
ccttttcgga gnccccnccc ctccgntggg nttact 396

<210> SEQ ID NO 86
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 86
ttttnnactg aatgtttaat acatttgnag gaacagaaga aatgcagtan ggattaanat 60
tttataatta gacattaatg taacagatgn ttcatttttc aaagaagntn ccccttntc 120 cctatctttt tttaatcttc cttanagcaa taantagtaa ttactatatt tgtggacaag 180
ctgctccact gtgntggaca gtaattatta aatctttatg tttcacatca ttattacctt 240
ccanaattct accttcattt ccctgcacag gttcactgga ctggntcaca ancaaattgn 300
actccactca antanaagag cccaaagaaa ttagagtaac gncnantcct atgaattana 360
gacccaaaga tttnaggngn tgattagaaa cataan 396

<210> SEQ ID NO 87
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 87
atggaggcgc tggggaagct gaagcagttc gatgcctacc ccaagacttt ggaggacttc 60
cgggtcaaga cctgcggggg cgccaccgtg accattgtca gtggccttct catgctgcta 120
ctgttcctgt ccgagctgca gtattacctc accacggagg tgcatcctga gctctacgtg 180
gacaagtcgc ggggagataa actgaagatc aacatcgatg tactttttcc ncacatgcct 240
tgtgcctatc tgagtattga tgccatggat gtggccngag aacancagct ggatgnggaa 300
cacaacctgt ttaagccacc actagataaa gatgcatccc ngtgagctca nagctgagcg 360
gcatgagctt gngaaantcn aggtgaccgg gtttga 396

<210> SEQ ID NO 88
<211> LENGTH: 396
<212> TYPE: DNA
<213> ORGANISM: Homo sapien
<220> FEATURE:

-continued

<221> NAME/KEY: misc_feature
<222> LOCATION: (1)...(396)
<223> OTHER INFORMATION: n = A,T,C or G

<400> SEQUENCE: 88

```
tccagagcag agtcagccag catgaccgag cgccgcgtcc ccttctcgct cctgcggggc     60

cccagctggg acccccttccg cgactggtac ccgcatagcc gctcttcgac caggccttcg    120

ggctgccccg gctgccggag gagtggtcgc agtggttagg cggcagcagc tggccaggct    180

acgtgcgccc cctgcccccc gccgcatcga gagccccgca gtggccgcgc ccgctacagc    240

cgcgcngctc agccggcaac tcacancggg gctcggagat ccgggacact gcggaccgct    300

ngcgcgtgcc ctggatgtca ccactttngc ccggacaact gacggtnana caaggatggg    360

gggtgganan nccngtaanc caagaanggg naggac                               396
```

<210> SEQ ID NO 89
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 89

```
gagagaacag taaacatcca gccttagcat ctctcangag tactgcagat cttcattagc     60

tatattcaca tggagnaatg ctattcaacc tatttctctt atcaaaacta attttgtatt    120

ctttgaccaa tgttcctaaa ttcactctgc ttctctatct caatcttttt cccctttctc    180

atctttcctc ctttttcag tttctaactt tcactggttc tttggaatgn tttttctttc     240

atctcttttc ttttacattt tggggtgtcc cctctctttt cttaccctct ttctncatcc    300

ttcttnttct tttgaattgg ctgcccttta tcntctcatc tgctgncatc ttcatttctc    360

ctccctcctn tttccnntca ttctactctc tcccnt                               396
```

<210> SEQ ID NO 90
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 90

```
gggcgccggc gcgccccccc acccccgccc cacgtctcgt cgcgcgcgcg tccgctgggg     60

gcggggagcg gtcgggccgg cngcggtcgg ccggcggcag ggtggtgcgn tttcnttttn    120

nattnnccnc nttcttcttn nttnnncnnn ctnntanncn ntnncnttcn cnnnntttnc    180

tntntcttna ccnnntttn taatcntctt ctncntnnnn tctcttnnat ntnttnctta     240

nttcctnnnn tttnttctnt cntttctcnc ctnnntctcn nnctcnncnc tcnncatttt    300

nntnttttnt nccttctnnt cttnnttctn ntnntnnttt nnnnttctnt tnntcatntt    360

ncctntntta ctntcanctt ntatnnncct cntttt                               396
```

<210> SEQ ID NO 91
<211> LENGTH: 396
<212> TYPE: DNA
<213> ORGANISM: Homo sapien
<220> FEATURE:
<221> NAME/KEY: misc_feature -continued
<222> LOCATION: (1)...(396)
<223> OTHER INFORMATION: n = A,T,C or G

<400> SEQUENCE: 91
ntntcctnna tttttnnntc nncttttttt tnnaattttt ctttnttttn tttataaaaa 60
tcnncacnta aaacngcgga anaggggatt tnttnttngg gngtancncn nggccncaaa 120
naaccccaaa aatancccaa aatgcacagg nccngggnaa angaccnacn tgggtntttt 180
ntttntnaac aaggggggtt ttaaagggna tnggnatcaa agggnataaa ntttaaacct 240
ttganaaatt ttttaanagg cttgcccccc actttggncc ccnccccncn gnngggatcc 300
aatttttttt cnttggggct cccngncccn nannttccgg gttnntggnc nntcctnntt 360
tttttttttt tgccttcacc cntnccattn cntttt 396

<210> SEQ ID NO 92
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 92
ctntttnnnt ntttttttcc ccatcatcca naaatgggtt ttattctcag ccgagggaca 60
gcaggactgg taaaaactgt caggccacac ggttgcctgc acagcacccc catgcttggt 120
agggggtggg agggatggcg ggggctggnt gnccacaggc cgggcatgac aaggaggctc 180
actggaggtg gcacactttg gagtgggatg tcgggggaca ncttctttgg tanttgggcc 240
acaagattcc caaggatanc acnnnnactg attnccannc tanagncaag cggntggcca 300
tntgtangnn nttntntatn tgactattta tagattttta tanaacaggg naagggcata 360
ccncaaaagg gnccaanttt ttaccnccgg gcnccc 396

<210> SEQ ID NO 93
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 93
gctgccacag atctgttcct ttgtccgttt ttgggatcca caggccctat gtatttgaag 60
ggaaatgtgt atggctcaga tcctttttga aacatatcat acaggttgca gtcctgaccc 120
aagaacagtt ttaatggacc actatgagcc cagttacata aagaaaaagg agtgctaccc 180
atgttctcat ccttcagaag aatcctgcga acggagcttc agtaatatat cgtggcttca 240
catgtgagga agctacttaa cactagttac tctcacaatg aaggacctgn aatgaaaaat 300
ctgnttctaa ccnagtcctn tttanatttt agngcanatc cagaccancg ncggtgctcg 360
agtaattctt tcatgggacc tttggaaaac tttcag 396

<210> SEQ ID NO 94
<211> LENGTH: 396
<212> TYPE: DNA
<213> ORGANISM: Homo sapien
<220> FEATURE:
<221> NAME/KEY: misc_feature
<222> LOCATION: (1)...(396)

-continued

```
<223> OTHER INFORMATION: n = A,T,C or G

<400> SEQUENCE: 94

tgccttaacc agtctctcaa gtgatgagac agtgaagtaa aattgagtgc actaaacgaa     60

taagattctg aggaagtctt atcttctgca gtgagtatgg cccaatgctt tctgnggcta    120

aacagatgta atgggaagaa ataaaagcct acgtgttggt aaatccaaca gcaagggaga    180

tttttgaatc ataataactc atanngtgct atctgtcagt gatgccctca gagctcttgc    240

tgntagctgg cagctgacgc ttctangata gttagnttgg aaatggtctt cataataact    300

acacaaggaa agtcanccnc cgggcttatg aggaattgga cttaataaat ttagngngct    360

tccnacctaa aatatatctt ttggaagtaa aattta                              396


<210> SEQ ID NO 95
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 95

cctcccaccc ncttanttca tgagattcga naatgncact tntgtgctnt ttnctnnttn     60

tattctnacn atttctttct tggngcggna nnaatcccnt ttttnngggc gnctctcccn    120

ncttntnntt tcntggngct ntcccttttc nnnnnaaact tntacnnngt ttanaantnt    180

ttctgnangg gggnntccna aanantttt ccncctncct nattccnctc tnaannctcn    240

cnaattgttt cccccccccn ntagnntatt ttttctaaaa aattaactcc nacgganaaa    300

attttcccta aaatttcncc tccanatttn gaaaaaacnc gcccggganct nntntncgaa    360

tntnaatttt tnaaaaaaan ttattttcat cnggnn                              396


<210> SEQ ID NO 96
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 96

cctgggtacc aaatttcttt atttgaagga atggtacaaa tcaaagaact taagtggatg     60

ttttggacaa cttatagaaa aggtaaagga aaccccaaca tgcatgcact gccttggcga    120

ccagggaagt caccccacgg ctatggggaa attagcccga ngcttaactt tcattatcac    180

tgcttccaag ggngtgcttg gcaaaaaaat attccgccaa ccaaatcggg cgctccatct    240

tgcccagttg gtnccgggnc cccaattctt ggatgctttc ncctcttntt ccggaatgng    300

ctcatgaant cccccaanng gggcattttg ccagnggccn tttngccatt cnagnnggcc    360

tgatccattt tttccaatgt aatgccnctt cattgn                              396


<210> SEQ ID NO 97
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G
```

-continued

<400> SEQUENCE: 97

```
ctcaccctcc tcntnnttnt canaatattg ngaacttnnt nctgntcgaa tcactggcat     60

taaagganca ctagctaatg gcactaaatt tacnnactan ggaaactttt ttataatant    120

gcaaaaacat ntnaaaaaga ntgnagttcg cccatttctg cttnggaaga nctcttcact    180

tntaanccon natgnngncc tttgggtcaa aanctccgcg attattacng ngttnccenc    240

tatttgncct tcctttntcc ccaangccnc anatttcnna actttnccnt naaatgcctt    300

tatttnatnn cntttcnacn ncttaanntt ccctttnaan aangatccct ncttcaaatn    360

ntttcccngt tcctngcatt ncccnnnnat ttctct                              396
```

<210> SEQ ID NO 98
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 98

```
acagggacaa tgaagccttt gaagtgccag tctatgaaga ggccgtggtg ggactagaat     60

cccagtgccg cccccaagag ttggaccaac caccccctac agcactgttg tgataccccc    120

agcacctgan gaggaacaac ctaccatcca gaggggccag gaaaagccaa actggaacag    180

aggcgaatgg ctcagagggg tncatggcca agaaggaagc cctggaagaa cttcaatcac    240

cttcggtttc gggaccaccg gcttgtgtcc ctgttctgac tgcanaactt ggcgcngtnc    300

cccattanaa cctntgactc nncccttgct ataagnctgt tttggcccct gatgatgata    360

gggtttttat gangacactt gggcaccccc ttaatg                              396
```

<210> SEQ ID NO 99
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 99

```
nttntttttc cgncnaaagg gcaagngttt ncatctttcc tgnccncnca ananngggtn     60

tntgtgcntt tntttttttcc caaaacccgg gtnggggaca ccttttgagg anccactnnt    120

cntccggggc nnnnttttag aaggngncta anaagcntct tgnnggggga aaaacatctt    180

tttgcncccn acatacccc  aaggggggggg ggtgtctggg agganactaa ngacttttnt    240

tttttnnccn caaanaactg anggccccca ttgctccccc cccantcttt aaaaaacccc    300

ttcaatttcc ttgncnggna aaaanggttg gnaaaaaang agngngcntc nnttncnttt    360

natggaaggn aaaaggtttt tggttgnaaa accccg                              396
```

<210> SEQ ID NO 100
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G -continued

<400> SEQUENCE: 100

```
ctaacacggt gaaaccctgt ctctactaaa aatacaaaaa aattagccag gcgtggtggc     60
gggcacctgt agtcccagct gctcaggaag ctgaggcagg agaatggcgt gaacccagaa    120
ggcggagctt gcagtgagct gagatcgtgt cagtgcactc cagcctgggc gacagagcga    180
gactcccgct caaaaaaaaa aaaaaaaaga gaaaagaaaa agctgcagng agctgggaat    240
gggccctatc ccctccttgg ggatcaatga gaccccttt caaaanaaaa aaaaaaataa    300
tgngattttg gnaacatatg gcactggtgc ttcnnggaat tctgtttntn ggcatgnccc    360
cctntgactg nggaaaaatc cagcaggagg cccana                              396
```

<210> SEQ ID NO 101
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 101

```
agttataact caacagttca tttatatgct gttcatttaa cagttcattt aaacagttca     60
ttataactgt ttaaaaatat atatgcttat agncaaaann tgttgtggcg nagttgttgc    120
cgcttatagc tgagcattat ttcttaaatt cttgaatgtt cttttggngg gntnctaaaa    180
ccgtatatga tccattttna tgggaaacng aattcntnnc attatcncac cttggaaata    240
cnnaacgtgg gggaaaaaaa tcattcccnc cntccaaaac tatacttctt ttatctngan    300
nttcttgntc ctgcncnggt ttngaatata nctgggcaaa nggntttncc aaatccntnt    360
acnntncttt gggaantanc ggcaantcnt cncttt                              396
```

<210> SEQ ID NO 102
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 102

```
actatacata agaacangct cacatgggag gctggaggtg ggtacccagc tgctgtggaa     60
cgggtatgga caggtcataa acctagagtc agngtcctgt tggcctagcc catttcagca    120
ccctgccact tggagnggac ccctctactc ttcttagcgc ctaccctcat acctatctcc    180
ctnctcccat ctcctacgga ctggcgccaa atggctttcc tgccaatttt gggatcttct    240
ctggctctcc agcctgctta ctcctctatt tttaaagggc caaacaaatc ccttctcttt    300
ctcaaacaca gtaatgnggc actgacccta ccacacctca tgaagggggc ttgttgcttt    360
tatttgggcc cgatctgggg ggggcaaaat attttg                              396
```

<210> SEQ ID NO 103
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 103

-continued

```
ttgtgttggg actgctgata ggaagatgtc ttcaggaaat gctaaaattg ggcaccctgc     60

cccaacttca aagccacagc tggtatgcca natggtcagg ttaaagatat caacctgctg    120

actacaaagg aaaatatggt ggggtcttct tttaccctct tgacttccct ttgngngccc    180

cccgaganca ttgctttccg ngatagggca aaanaaatta aaaaacttaa ctggccagtg    240

aatggggctt ctgnggatct ccttctggca ttacatnggc aatccctaaa aaacaagang    300

actgggaccc ataacattct tttgnatcaa ccgaagcccc cattgttang atatngggct    360

taaangctga tnaagcatct cgtccgggcn ttttat                              396
```

<210> SEQ ID NO 104
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 104

```
aagggagggc gcgccaagac cttcccactc gngcacactg ggggcgccga cangacgcaa     60

cccagtccaa cttggatacc cttggnttta gttctcggac acttctttta tctctccgtc    120

gcaacttgtc aagttctcaa nactgtctct ctgngntatc ttttttcttc gctgctcttc    180

nncccccgac gtatttntca aaangtctgc aattgttgna tacntnganc tncaccactg    240

ttacnaggtc atnaatttcn cntcaactct ntnccncttg ttccctgata tntcggccgg    300

ngncnccaat tctgtatttt nctcntcaac gntctcactt ttncctcctc cnggccactt    360

tctccccttc cttattccgg cnttgtttgc cnccat                              396
```

<210> SEQ ID NO 105
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 105

```
tcaatagcca gccagtgttc atttttatcc ttgagctttt agtaaaaact tcctggnttt     60

atttttagtc attgggtcat acagcactaa agtctgctat ttatggaaac taactttttt    120

gtttttaatc caggccaaca tgtatgtaaa ttaaattttt agataattga ttatctcttt    180

gtactacttg agatttgatt atgagatgtg catattgctt tgggaagagc tcgaggaagg    240

aaataattct ctcctttggt ttgaacctca actagataaa ccctaggaat tgttaactgc    300

acaagnattt tcattccaca aaacctgagg cagctctttt gccagagcgt tcctgnaccc    360

ccccacccca cttgccttgg gtctttanaa ngagcc                              396
```

<210> SEQ ID NO 106
<211> LENGTH: 396
<212> TYPE: DNA
<213> ORGANISM: Homo sapien

<400> SEQUENCE: 106

```
gctgtgtagc acactgagtg acgcaatcaa tgtttactcg aacagaatgc atttcttcac     60

tccgaagcca aatgacaaat aaagtccaaa ggcattttct cctgtgctga ccaaccaaat    120
```

-continued

```
aatatgtata gacacacaca catatgcaca cacacacaca cacacccaca gagagagagc    180

tgcaagagca tggaattcat gtgtttaaag ataatccttt ccatgtgaag tttaaaatta    240

ctatatattt gctgatggct agattgagag aataaaagac agtaaccttt ctcttcaaag    300

ataaaatgaa aagcaattgc tcttttcttc ctaaaaaatg caaaagattt acattgctgc    360

caaatcattt caactgaaaa gaacagtatt gctttg                              396


<210> SEQ ID NO 107
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 107

ttcacagaac anggtggttt attatttcaa tagcaaagag ctgaaaaatg tcgggtccca     60

taaaggagca gaacctgacc cagagcctgc agtacatttc caccccacag gggtgcaggc    120

tgggccaggc agggccaaag gcagcagaaa tgggagtaag agactgtgcc cactgagaag    180

ctctgctggg tgtgggcagg tgggcatgan atgatgatga tgtagtgtaa ggaccaggta    240

ggcaaaacct gtcaggnttg ntgaatgtca nagtggatcc aaaaggctga gggggtcgtc    300

anaaggccgg nggncccncc cttgcccgta tgggccttca aaaagtatgc ttgctcatcc    360

gttgtttncc ccanggagct gccanggana aggctn                              396


<210> SEQ ID NO 108
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 108

gcctgctttt gatgatgtct acagaaaatg ctggctgagc tgaacacatt tgcccaattc     60

caggtgtgca cagaaaaccg agaatattca aaattccaaa tttttttctt aggagcaaga    120

agaaaatgtg gccctaaagg gggttagttg aggggtaggg ggtagtgagg atcttgattt    180

ggatctcttt ttatttaaat gtgaatttca acttttgaca atcaaagaaa agacttttgt    240

tgaaatagct ttactgcttc tcacgtgttt tggagaaaan natcancccct gcaatcactt   300

tttgnaactg ncnttgattt tcngcnncca agctatatcn aatatcgtct gngtanaaaa    360

tgncctggnc ttttgaanga atacatgngt gntgct                              396


<210> SEQ ID NO 109
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 109

ggccgtaggc agccatggcg cccagcccgg aatggcatgg tcttgaagcc ccacttccac     60

aaggactggc agcggcgcgt ggccacgtgg ttcaaccagc cggcccggaa gatccgcaga    120

cgtaaggccc ggcaagccaa ggcgcgccgc atcgctccgc gccccgcgtc gggtcccatc    180
```

-continued

```
cggcccatcg tgcgctgccc acggttcggt accacacgaa gggcgcgccg gcgcggnttc    240

agcctggagg agctcagggt ggccggattt acaagaagng gccngacatc ngtattcttg    300

ggatncnnga agnggaacaa gtcacngagt ccttgcagcc acntcagcgg ntgatgacac    360

cgttcnaact catctnttcc caagaaacct cngnnc                              396


<210> SEQ ID NO 110
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 110

nntgggctcc tnncantnat aataaaccng actcatacnc cacaaggaga tgaacaggan     60

tatgtncatn ctgacgcgga aacagngcan ggagctgagg aggngccaag atgagaccta    120

nnggccnngg tgggcgcatt cccggnggag ggggccacta aggantacga nnntcnagcg    180

gctcttgnng gcngncctcc tcacncctgn ntattcgatt gtcncnnatg ncntcctatn    240

atnntcanna ttctntnntn atctcntnta cnncntcncn ttcatgntta cngntccctc    300

tcnttctnac cnttntctgn anctcctttc tnnnnctttc atctntnttc ngctttcttt    360

ctnnaatcnt nntttaacnt nntctncttt ntnatt                              396


<210> SEQ ID NO 111
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 111

taangancat nctggnttnt gcctnnccgn ctnattgant gttaaaggca attntgtggn     60

tgtcccagng aatgncggct nattttcttt ccacattgng cncattcact cctcccactc    120

ttggcatgtn gngacataag canggtacat aatngnaaaa atctgnattt ctgatgccan    180

angggtanan cntnttgnat ntcattccat tgatatacag ccactntttt atttttgatc    240

ancggccttc ggntcactgc ncanggtact tgacctcagt gtcactatta tgggntttgg    300

tttcnctctt ttncnggccn ttntntttcn cacnttncan cttncttnnt nnaaaannna    360

nncactctct cttgctctct ngatacnnng tctnaa                              396


<210> SEQ ID NO 112
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 112

tcaacgtcac caattactgc catttagccc acgagctgcg tctcagctgc atggagagga     60

aaaaggtcca gattcgaagc atggatccct ccgccttggc aagcgaccga tttaacctca    120

tactggcaga taccaacagt gaccggctct tcacagtgaa cgatgttaaa gntggaggct    180
```

-continued

```
ccaagnatgg tatcatcaac ctgcaaagtc tgaagacccc tacgctcaag gtgttcatgc    240

acgaaaacct ctacttcacc aaccggaagg tgaattcggg gggctgggcc tcgctgaatc    300

acttggattc cacattctgc tatgcctcat gggactcgca gaacttcagg ctggccaccc    360

tgctcccacc atcactgntn gncaatantc acccag                              396


<210> SEQ ID NO 113
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 113

nnnnttnnnn nggagcctta atttcagagt tttattgtat tgcactaaag gaacagcagg     60

atggntatac aattttctct cattcagttt tgaaaatctg tagtacctgc aaattcttaa    120

gaataccttt accaccagat tagaacagta agcataataa ccaatttctt aataagtaat    180

gtcttacaaa taaaaacaca tttaaaatag ctttaaatgc attcttcaca agtaattcag    240

catatatttt atatcatggt tacttatgct tangaattnn agcaggatnt ttattctttt    300

gatggaaata tgggaaaact ntattcatgc atatacangg ataatattca gcgaagggaa    360

aatcccgttt ttattttggn aatgattcat atataa                              396


<210> SEQ ID NO 114
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 114

aaatgggaca acgtgattct tttgttttaa ataaatactn agaacacgga cttggctcct     60

acaagcattt ggactctaag gnttagaact ggagagtctt acccatgggc cccncncagg    120

gacgccacgg ttccctccca ccccgngatc aagacacgga atcngntggc gatngttgga    180

tcgcnatgtg ccccttatct atagccttcc cnggncatnt acangcagga tgcggntggg    240

anaactacaa ctgnaatntc tcnaacggtn atggtcccca ccgatnaaga ttctacctng    300

tcttttcntc ccctggagtg tgagtgnnng aggaagaagc ccttncctta catcaccttt    360

tgnacttctg aacaaganca anacnatggc cccccc                              396


<210> SEQ ID NO 115
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 115

ccgcctggtt cggcccgcct gcctccactc ctgcctctac catgtccatc agggtgaccc     60

agaagtccta caaggtgtcc acctctggcc cccgggcctt cagcagccgc tcctacacga    120

gtgggcccgg ttcccgcatc agctcctcga gcttctcccg agtgggcagc agcaactttc    180

gcggtggcct ggcggcggct atggtggggc cagcggcatg ggaggcatca cccgcagtta    240
```

-continued

```
cggcaaccag agcctgctga gccccttgcc tggaggngga ccccaacatc aagccgngcg    300

cacccaggaa aaggagcaga ncaagaccct caacaacaag nttgcttctt catagacaag    360

ggaccggtcc ttgaacagca naacaagatg ntggag                              396


<210> SEQ ID NO 116
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 116

atctcagttt actagctaag tgactttggg caagggattt aacctctcgt ccctcagttt     60

cctcctatgt aaaatgacaa ggataatagt accaacccaa tgtagattaa atgagtttac    120

gaagtgttag aatagtgctt ggcacattag tgctttacaa ctgctatttt gattgttgtt    180

gtgggctctc tcaaatgcat tgtctctaga tgccagtgac ccaggtcaaa atttaccttt    240

aaccaagctg catgtttccc agactgntgc acagtcctct accctgagan aaagcttcca    300

cccaaggata cttttacttt ctgctggaaa actgatgagc aanggcaaca ngggacactt    360

atcgccaact ggaaangaga aattcttcct tttgct                              396


<210> SEQ ID NO 117
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 117

aaacattttt taataaaatt cctatagaaa gctcagtcat agggcaaata ctcagttctc     60

tttcccatat caccgaggat tgagagctcc caatattctt tggagaataa gcagtagttt    120

tgctggatgt tgccaggact cagagagatc acccatttac acattcaaac cagtagttcc    180

tattgcacat attaacatta cttgccccta gcaccctaaa tatatggnac ctcaacaaat    240

aacttaaaga tttccgtggg gcgcganacc atttcaattt gaactaatat ccttgaaaaa    300

aatcacatta ttacaagntt taataaatac nggaagaaga gctggcattt ttctaanatc    360

tgaattcnga cttggnttta ttccataaat acggtt                              396


<210> SEQ ID NO 118
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 118

accnncacct gntnnntttt aacnattaca acttctttat atggcagttt ttactgggng     60

cctaacactc tctttactgn ctcaagngga agtccaaaca aatttcattt ttgtagtaaa    120

aaatctttat ttccaaaatg atttgttagc caaaagaact ataaaccacc taacaagact    180

ttggaagaaa gagacttgat gcttcttata aattccccat tgcanacaaa aaataacaat    240
```

```
ccaacaagag catggtaccc attcttacca ttaacctggn tttaannctc caaancnnga        300

tttaaaaatg accccactgg gcccaatcca acatganacc taggggggnt tgccttgatt        360

angaatcccc cttanggact ttatctnggc tganaa                                 396
```

<210> SEQ ID NO 119
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 119

```
atggccagct cactttaaat accacctcaa gactcatcga aatgaccgct ccttcatctg         60

tcctgcagaa ggttgtggga aaagcttcta tgtgctgcag aggctgaagg tgcacatgag        120

gacccacaat ggagagaagc cctttatgtg ccatgagtct ggctgtggta agcagtttac        180

tacagctgga aacctgaaga accaccggcg catccacaca ggagagaaac ctttcctttg        240

tgaagcccaa ngatgtggcc gtcctttgct gagtattcta ncttcgaaaa catctggngg        300

ntactcanga gagaaagcct cattantgcc antctgnggg aaaaccttct ntcagagngg        360

angcaggaat gtgcatatta aaaagctncc ttgnac                                 396
```

<210> SEQ ID NO 120
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 120

```
catgggtcag tcggtcctga gagttcgaag agggcacatt cccaaagaca ttcccagtca         60

tgaaatgtag aagactggaa aattaagaca ttatgtaaag gtagatatgg cttttagagt        120

tacattatgc ttggcatgaa taaggtgcca ggaaaacagt ttaaaattat acatcagcat        180

acagactgct gttagaaggt atgggatcat attaagataa tctgcagctc tactacgcat        240

ttattgttaa ttgagttaca nangncattc annactgagt ttatagancc atattgctct        300

atctctgngn agaacatttg attccattgn gaagaatgca gtttaaaata tctgaatgcc        360

atctagatgt attgtaccna aagggaaaa ataaca                                  396
```

<210> SEQ ID NO 121
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 121

```
tttttttttt ttttttttaa aatcaagtta tgtttaataa acattaataa atgtttactt         60

aaaagggtta ataaacnttt actacatggc aaattatttt agctagaatg cttttggctt        120

caagncatan aaaccagatt cnaatgccct taaanaattt tnaaanatcc attgangggg        180

ataactgtaa tccccaaggg gaanagggtt gggtatgaca ggtacanggg gccagcccag        240

tnntnncana nncagactct taccntcttt ctgctgtgnc accctcaggc attggctcca        300
```

-continued ttctcngggn tgcncatggg aagatggctt tggacntaac nacacccttt tgtncacgta 360
aaggccngat gcagggtcaa anagnttccn ccatnt 396

<210> SEQ ID NO 122
<211> LENGTH: 396
<212> TYPE: DNA
<213> ORGANISM: Homo sapien

<400> SEQUENCE: 122
gtcgacatgg ctgccctctg ggctcccaga acccacaaca tgaaagaaat ggtgctaccc 60
agctcaagcc tgggcctttg aatccggaca caaaaccctc tagcttggaa atgaatatgc 120
tgcactttac aaccactgca ctacctgact caggaatcgg ctctggaagg tgaagctaga 180
ggaaccagac ctcatcagcc caacatcaaa gacaccatcg gaacagcagc gcccgcagca 240
cccaccccgc accggcgact ccatcttcat ggccaccccc tgcggtggac ggttgaccac 300
cagccaccac atcatcccag agctgagctc ctccagcggg atgacgccgt ccccaccacc 360
tccctcttct tctttttcat ccttctgtct ctttgt 396

<210> SEQ ID NO 123
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 123
gccctttttt tttttttttt tttcctagtg ccaggtttat tccctcacat gggtggttca 60
catacacagc acanaggcac gggcaccatg gganagggca gcactcctgc cttctgaggg 120
gatcttggcc tcacggtgta anaagggana ggatggtttc tcttctgccc tcactagggc 180
ctagggaacc cagnagcaaa tcccaccacg ccttccatnt ctcagccaag ganaagccac 240
cttggtgacg tttagttcca accattatag taagtggana agggattggc ctggtcccaa 300
ccattacagg gtgaanatat aaacagtaaa ggaanataca gtttggatga ggccacagga 360
aggagcanat gacaccatca aaagcatatg caggga 396

<210> SEQ ID NO 124
<211> LENGTH: 396
<212> TYPE: DNA
<213> ORGANISM: Homo sapien

<400> SEQUENCE: 124
gaccattgcc ccagacctgg aagatataac attcagttcc caccatctga ttaaaacaac 60
ttcctccctt acagagcata caacagaggg ggcacccggg gaggagagca catactgtgt 120
tccaatttca cgcttttaat tctcatttgt tctcacacca acagtgtgaa gtgcgtggta 180
taatctccat ttcaaaacca aggaagcagc ctcagagtgg tcgagtgaca cacctcacgc 240
aggctgagtc cagagcttgt gctcctcttg attcctggtt tgactcagtt ccaggcctga 300
tcttgcctgt ctggctcagg gtcaaagaca gaatggtgga gtgtagcctc cacctgatat 360
tcaggctact cattcagtcc caaatatgta ttttcc 396

<210> SEQ ID NO 125
<211> LENGTH: 396
<212> TYPE: DNA

-continued

<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 125 ccctttttttt ttttttttt ttttttttt tttttttactt tgnaacaaaa atttattagg 60
attaagtcaa attaaaaaac ttcatgcncc nccncttgtc atatttacct gaaatgacaa 120
agttatactt agcttgagng naaaacttgn gccccaaaaa ttntgtttgg aaagcaaaaa 180
aataattgat gcncatagca gngggcctga tnccnccaca gngaatgttg tttaaggnct 240
aacaaacagg ggncancaaa gcatacatta cttttaagct ttgggnccaa ggaaaangtc 300
attccctacc tccttcaaaa gcaaactcat natagcctgg gcncctaggn ctggagcctn 360
ttttttcgag tctaanatga acatntggat ttcaan 396

<210> SEQ ID NO 126
<211> LENGTH: 396
<212> TYPE: DNA
<213> ORGANISM: Homo sapien

<400> SEQUENCE: 126
cgcgtcgact cgcaagtgga atgtgacgtc cctggagacc ctgaaggctt tgcttgaagt 60
caacaaaggg cacgaaatga gtcctcaggt ggccaccctg atcgaccgct ttgtgaaggg 120
aaggggccag ctagacaaag acaccctaga caccctgacc gccttctacc ctgggtacct 180
gtgctccctc agccccgagg agctgagctc cgtgcccccc agcagcatct gggcggtcag 240
gccccacgac ctggacacgc tggggctacg gctacagggc ggcatcccca acggctacct 300
ggtcctagac ctcagcatgc aagaggccct ctcggggacg ccctgcctcc taggacctgg 360
acctgttctc accgtcctgg cactgctcct agcctc 396

<210> SEQ ID NO 127
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 127
tttttttttt ttggnggtaa aatgcaaatg ttttaaaata tgtttatttt gtatgtttta 60
caatgaatac ttcagcaaag aaaataatta taatttcaaa atgcaatccc tggatttgat 120
aaatatcctt tataatcgat tacactaatc aatatctaga aatatacata gacaaagtta 180
gctaatgaat aaaataagta aaatgactac ataaactcaa tttcagggat gagggatcat 240
gcatgatcag ttaagtcact ctgccacttt ttaaaataat acgattcaca tttgcttcaa 300
tcacataaac attcattgca ggagttacac ggctaatcat tgaaaattat gatctttgtt 360
agcttaaaag aaaattcagt ttaatacaaa gacatt 396

<210> SEQ ID NO 128
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 128
gccctttttt ttttttttta aaggcaaata aaataagttt attgggatgt aaccccatca 60
taaattgagg agcatccata caggcaagct ataaaatctg gaaaatttaa atcaaattaa 120
attctgcttt taaaaaggtg ccttaagtta accaagcatt ttgataacac attcaaattt 180
aatatataaa aatagatgta tcctggaaga tataatgaan aacatgccat gtgtataaat 240
tcanaatacg ctttttacac aaagaactac aaaaagttac aaagacagcc ttcaggaacc 300
acacttagga aaagtgagcc gagcagcctt cacgcaaagc ctccttcaaa naagtctcac 360
aaagactcca gaaccagccg agtntgtgaa aaagga 396

<210> SEQ ID NO 129
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 129
gccctttttt tttttttttt ttttactcag acaggcaata tttgctcaca tttattctct 60
tgcatcgtaa atagtagcca actcacaaaa ataaagtata caanaatgta atattttttta 120 aaataagatt aacagtgtaa gaaggaaaat ctcaaaaaaa gcanatagac aatgtanaaa 180
attgaaatga aatcccacag taanaaaaaa aaaacanaaa agtgcctatt taanaattat 240
gctacatgtg gaacttaact agaccatttt aanaaagacc aatttctaat gcaaattttc 300
tgaggttttc anattttatt tttaaaatat gttatagcta catgttgtcn acncggccgc 360
tcgagtctan agggcccgtt taaacccgct gatcag 396

<210> SEQ ID NO 130
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 130 cgccctttttt tttttttttt tanngnacgt gnctttattt ctggatgata taaaanaaaa 60
aacttaaaaa acaccccaaa ccaaacacca atggatcccc aaagcgatgt gactccctct 120
tcccacccgg ataaatagag acttctgtat gtcagtctac cctcccgccc ccataacccc 180
ctctgctata nacatactct gggtatatat tactctactc ggcaatagac atctcccgaa 240
aatagaattc ctgccctgac acctgactct tccctggccg catcanacca cccgccactg 300
tagcacactg gtgtccttgc cccctgtggt cagggccatg ctgtcatccc acaanaaggc 360
cacatttgtc acatggctgc tgtgtccacc gtactt 396

<210> SEQ ID NO 131
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G -continued

<400> SEQUENCE: 131
gccctttttt tttttttttt tttttttttt ttcagtttac acaaaaacnc tttaattgac 60
agtatacnnt tttccaaaat atnttttngt aanaaaatgc aataattatt aactatagtt 120
tttacaaaca agtttntcan taaattccag tgtncttnaa accccnnncn annaaaacat 180
atatganccc ccagttcctg ggcaaactgt tgaacattca ctgcanacaa aaagaccanc 240
nccaaanagt catctgngnc ctccatgctg ngtttgcacc aaacctgagg gancagctag 300
ngaccgtgac aaaagctntg ctacagtttt actntngccc tntntgcctc ccccatnatg 360
tttccttggt ccctcantcc tgtnggagta agttcc 396

<210> SEQ ID NO 132
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 132
cgcgtcgacc gcggccgtag cagccgggct ggtcctgctg cgagccggcg gcccggagtg 60
gggcggcgnt atgtaccttc cacattgagt attcagaaag aagtgatctg aactctgacc 120
attctttatg gatacattaa gtcaaatata agagtctgac tacttgacac actggctcgg 180
tgagttctgc tttttctttt taatataaat ttattatgtt ggtaaattta gcttttggct 240
tttcactttg ctctcatgat ataagaaaat gtaggttttc tctttcagtt tgaattttcc 300
tattcagtaa aacaacatgc tagaaaacaa acttttggaa aggcattgta actatttttt 360
caaatagaac cataataaca agtcttgtct taccct 396

<210> SEQ ID NO 133
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 133
ntattacccc tcctggnnan ntggnnatan nctgcaaggn gatnnncccg nngaacttca 60
ctgatnnncc aatnaaaact gctttaaanc tgactgcaca tatgaattnt aatacttact 120
tngcgggagg ggtggggcag ggacagcaag ggggaggatt gggaanacaa tagacaggca 180
tgctggggat gcngcgggct ctatggcttc tgangcgnaa agaaccagct ggggctctag 240
ggggtatccc cacgcgccct gtagcngcnc attaaacgcg gcgggtgtgg nggttacttc 300
gcaaagngac cgatncactt gccagcgccc tagctgcccg ctcctttngc tttcttccct 360
tcctttctcg ccacnttnnc cggctntccc cgncaa 396

<210> SEQ ID NO 134
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 134

-continued tttttttttt ttctgctttt tatatgttta aaaatctctc attctattgc tgctttattt 60
aaagaaagat tactttcttc cctacaagat ctttattaat tgtaaaggga aaatgaataa 120
ctttacaatg ganacacctg gcanacacca tcttaaccaa agcttgaagt taacataacc 180
agtaatagaa ctgatcaata tcttgtgcct cctgatatgg ngtactaana aaaacacaac 240
atcatgccat gatagtcttg ccaaaagtgc ataacctaaa tctaatcata aggaaacatt 300
anacaaactc aaattgaagg acattctaca aagtgccctg tattaaggaa ttattcanag 360
taaaggagac ttaaaagaca tggcaacaat gcagta 396

<210> SEQ ID NO 135
<211> LENGTH: 396
<212> TYPE: DNA
<213> ORGANISM: Homo sapien

<400> SEQUENCE: 135
gcgtcgacgc tggcagagcc acaccccaag tgcctgtgcc cagagggctt cagtcagctg 60
ctcactcctc cagggcactt ttaggaaagg gtttttagct agtgtttttc ctcgctttta 120
atgacctcag ccccgcctgc agtggctaga agccagcagg tgcccatgtg ctactgacaa 180
gtgcctcagc ttccccccgg cccgggtcag gccgtgggag ccgctattat ctgcgttctc 240
tgccaaagac tcgtgggggc catcacacct gccctgtgca gcggagccgg accaggctct 300
tgtgtcctca ctcaggtttg cttcccctgt gcccactgct gtatgatctg ggggccacca 360
ccctgtgccg gtggcctctg ggctgcctcc cgtggt 396

<210> SEQ ID NO 136
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 136
ttatgcttcc ggctcgtntg ttgtgtggaa ttgtgagcgg ataacaattt cacacaggaa 60
acagctatga ccatgattac gccaagctat ttaggtgaca ctatagaata ctcaagctat 120
gcatcaagct tggtaccgag ctcggatcca ctagtaacgg ccgccagtgt gctggaattc 180
gcggncgntc nantctagag ggcccgttta aacccgctga tcagcctcga ctgtgccttc 240
tagttgccag ccatctgttg tttgcccctc ccccgtgcct tccttgaccc tggaaggtgc 300
cactcccact gtcctttcct aataaaatga ggaaattgca tcgcattgtc tgagtaggtg 360
tcattctatt ctggggggtg gggtggggca ggacan 396

<210> SEQ ID NO 137
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 137
tttttttttt ttctgctttg tacttgagtt tatttcacaa aaccacggag aaagatactg 60
aaatggagct ctttccagcc tccaagcaag gaggccccag cagccagtct ccagcccctt 120

-continued

```
gagcccttttt tgttaggccc acacccaaaa gagganaacc agtgtgtgcg cgaaggtaca    180

tggcaaggca cttttgaaaa catcccagtt taccgnggtg aaattgaact tactctgaaa    240

cagatgaaaa gggacatgca aaattgctga gcacatggag gtgtttgtta gtaggtgaaa    300

atcatgtcct gggtataacc cagcttctcc aggttagggt gagccgccgt ctggatcagt    360

ggtggcgggc cacacaccag gatgagcgtg gacttc                              396
```

```
<210> SEQ ID NO 138
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 138

cccttttttt ttttttttac aaatgagaaa aatgtttatt aagaaaacaa tttagcagct     60

ctcctttana attttacaga ctaaagcaca acccgaaggc aattacagtt tcaatcatta    120

acacactact taaggngctt gcttactcta caactggaaa gttgctgaag tttgtgacat    180

gccactgtaa atgtaagtat tattaaaaat tacaaattgt ttggtgatta ttttgatgac    240

ctcttgagca gcagctcccc ccaanaatgc ancaatggta tgtggctcac cagctccata    300

tcggcaaaat tcgtggacat aatcatcttt caccattaca gataaaccat attcctgaag    360

gaagccagtg agacaagact tcaactttcc tatatc                              396
```

```
<210> SEQ ID NO 139
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 139

ccgccctttt tttttttttt ttcacaaaag cactttttat ttgaggcaaa nagaagtctt     60

gctgaaagga ttccagttcc aagcagtcaa aactcaaccg ttagnggcac tattttgacc    120

tggtanattt tgcttctctt tggtcanaaa agggtattca ggttgtactt tccccagcag    180

ggtaaaaaga agggcaaagc aaactggaan anacttctac tctactgaca gggctnttga    240

natccaacat caagctanac acnccctcgc tggccactct acaggttgct gtcccactgc    300

tgagtgacac aggccatact acatttgcaa ggaaaaaaat gaggcaanaa acacaggtat    360

aggtcacttg gggacgagca ggcaaccaca gcttca                              396
```

```
<210> SEQ ID NO 140
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 140

tttttttttt tttttttttt tttttttctc atttaacttt tttaatgggn ctcaaaattn     60

tgngacaaat ttttggtcaa gttgtttcca ttaaaaagtn ctgattttaa aaactaataa    120

cttaaaactg ccncncccaa aaaaaaaaac caaaggggtc cacaaaacat tntcctttcc    180
```

-continued ttntgaaggn tttacnatgc attgttatca ttaaccagtn ttttactact aaacttaaan 240
ggccaattga aacaaacagt tntganaccg ttnttccncc actgattaaa agnggggggg 300
caggtattag ggataatatt catttancct tntgagcttt ntgggcanac ttggngacct 360
tgccagctcc agcagccttn ttgtccactg ntttga 396

<210> SEQ ID NO 141
<211> LENGTH: 396
<212> TYPE: DNA
<213> ORGANISM: Homo sapien

<400> SEQUENCE: 141
acgccgagcc acatcgctca gacaccatgg ggaaggtgaa ggtcggagtc aacggatttg 60
gtcgtattgg gcgcctggtc accagggctg cttttaactc tggtaaagtg gatattgttg 120
ccatcaatga ccccttcatt gacctcaact acatggttta catgttccaa tatgattcca 180
cccatggcaa attccatggc accgtcaagg ctgagaacgg gaagcttgtc atcaatggaa 240
atcccatcac catcttccag gagcgagatc cctccaaaat caagtggggc gatgctggcg 300
ctgagtacgt cgtggagtcc actggcgtct tcaccaccat ggagaaggct ggggctcatt 360
tgcagggggg agccaaaagg gtcatcatct ctgccc 396

<210> SEQ ID NO 142
<211> LENGTH: 396
<212> TYPE: DNA
<213> ORGANISM: Homo sapien

<400> SEQUENCE: 142
acgcaggaga ggaagcccag cctgttctac cagagaactt gcccaggtca gaggtctgcg 60
tagaagccct tttctgagca tcctctcctc tcctcacacc tgccactgtc ctctgcgttg 120
ctgtcgaatt aaatcttgca tcaccatggt gcacttctgt ggcctactca ccctccaccg 180
ggagccagtg ccgctgaaga gtatctctgt gagcgtgaac atttacgagt ttgtggctgg 240
tgtgtctgca actttgaact acgagaatga ggagaaagtt cctttggagg ccttctttgt 300
gttccccatg gatgaagact ctgctgttta cagctttgag gccttggtgg atgggaagaa 360
aattgtagca gaattacaag acaagatgaa ggcccg 396

<210> SEQ ID NO 143
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 143
tttttttttt tttccatana aaataggatt tattttcaca tttaaggnga acacaaatcc 60
atgttccana aatgttttat gcataacaca tcatgagtag attgaatttc tttaacacac 120
anaaaaatca aagcctacca ggaaatgctt ccctccggag cacaggagct tacaggccac 180
ttntgttagc aacacaggaa ttcacattgt ctaggcacag ctcaagngag gtttgttccc 240
aggttcaact gctcctaccc ccatgggccc tcctcaaaaa cgacagcagc aaaccaacag 300
gcttcacagt aaccaggagg aaagatctca gngggggaac cttcacaaaa gccctgagtt 360
gtgtttcaaa agccaagctc tggggtctgn ggcctg 396

-continued

<210> SEQ ID NO 144
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 144

```
tttttttttt tttcgctctt tggtctgaca agaaaagagt tttaggtgtg tgaagtaggg     60

tgggaaaaaa ggtcagtttc aaattcagta acatatggta acactaagtt aggctgctgc    120

attcttttct ttgggtactt aagccagctg gcacttccac tttgtaacca attatattat    180

gatcaacaac taatcagtta gttcctcagc ttcaactgaa nagttcctga ttacctgatg    240

aaggacatac ttgctctggc ttcaattagc atgctgtcaa gcatccctct ccatgcttaa    300

catggcaaca caaaacccaa gagtccttct ntttttttca ttagccatga ataaacactc    360

acaaagggga agagtagaca ctgcttttag taaacg                              396
```

<210> SEQ ID NO 145
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 145

```
tttttttttt tttttttcaa tggatccgtt agctttacta ctaanatctt gctganatca     60

nanaagggct tctgggcagg ctgagcactg ggggtgtgca acatggtaac tctgaataan    120

anaaaccctg agttttactg ggcaaanaaa naacaagngg taggtatgat ttctgaacct    180

ggaaatagcg aaaatgaagg aaattccaaa agcgcgtatt tccaaataat gacaggccag    240

caagaggaca ccaaacctnt anaaagaggt attntttctt ccagctactg atggctttgg    300

catcccacag gcacattcct ttggccttca ggatcttana tgcanatgtg ganagtcaag    360

aggtaggctg actctgagtc ttcagctaaa ttcttt                              396
```

<210> SEQ ID NO 146
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 146

```
tttttttttt ttttcattag caaggaagga tttatttttt cttttgaggg gagggcggaa     60

cagccgggat ttttggaaca ctacctttgt ctttcacttt gttgtttgtg tgttaacacn    120

aataaatcan aagcgacttt aaatctccct tcgcaggact gtcttcacgt atcagngcan    180

acaanaaaac agtggcttta caaaaaaanat gttcaagtag gctgcacttt gcctctgngg    240

gtgaggcaca ctgngggana nacaaggtcc cctgnaacca gaggngggaa ggacanagct    300

ggctgactcc ctgctctccc gcattctctc ctccatgtgt tttgaanagg gaagcaacat    360

gttgaggtct gatcatttct acccagggaa cctgtt                              396
```

-continued

<210> SEQ ID NO 147
<211> LENGTH: 396
<212> TYPE: DNA
<213> ORGANISM: Homo sapien

<400> SEQUENCE: 147
acggggaagc caagtgaccg tagtctcatc agacatgagg gaatgggtgg ctccagagaa 60
agcagacatc attgtcagtg agcttctggg ctcatttgct gacaatgaat tgtcgcctga 120
gtgcctggat ggagcccagc acttcctaaa agatgatggt gtgagcatcc ccggggagta 180
cacttccttt ctggctccca tctcttcctc caagctgtac aatgaggtcc gagcctgtag 240
ggagaaggac cgtgaccctg aggcccagtt tgagatgcct tatgtggtac ggctgcacaa 300
cttccaccag ctctctgcac cccagccctg tttcaccttc agccatccca acagagatcc 360
tatgattgac aacaaccgct attgcacctt ggaatt 396

<210> SEQ ID NO 148
<211> LENGTH: 396
<212> TYPE: DNA
<213> ORGANISM: Homo sapien

<400> SEQUENCE: 148
acgtcccatg attgttccag accatgactc ttcctggttg tgggtttgtt acagagcagg 60
agaagcagag gttatgacag ttatgcagac tttccccctc ctttttctct tttctcttcc 120
ccttgctttt ccactgtttc ttcctgctgc cacctgggcc ttgaattcct gggctgtgaa 180
gacatgtagc agctgcaggg tttaccacac gtgggagggc agcccagtac tgtccctctg 240
ccttccccac tttgagaata tggcagcccc tttcattcct ggcttggggt aggggagacc 300
attgaagtag aagcctcaaa gcagactttt ccctttactg tgtgtactcc aggacgaaga 360
aggaagatca tgcttgatac ttagattggt tttccc 396

<210> SEQ ID NO 149
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 149
tttttttttt tttaaagagt cacattttat tcaatgccta tttgtacatg ttactagcaa 60
taaactcttt tatctttaat tttgagaagt tttacaaata cagcaaagca gaatgactaa 120
tagagccggt aaccaggaca cagatttgga aaaataggtc taattggttg ttacactgtg 180
tttatgtcat acatttcgct tatttttatc aaanaaaaat cagaatttat aaaatgttaa 240
ttaaaaggaa aacattctga gtaaatttag tcccgtgttt cttcctccaa atctntttgt 300
tctacactaa caggtcagga taagtatgga tggggaggct ggaaaaaggg catccttccc 360
catgcggtcc ccagagccac cctctccaag caggac 396

<210> SEQ ID NO 150
<211> LENGTH: 396
<212> TYPE: DNA
<213> ORGANISM: Homo sapien

<400> SEQUENCE: 150
acgcctctct tcagttggca cccaaacatc tggattggca aatcagtggc aagaagttcc 60

-continued

```
agcatctgga cttttcagaa ttgatcttaa gtctactgtc atttccagat gcattatttt    120

acaactgtat ccttggaaat atatttctag ggagaatatt attgaagaaa atgttaatag    180

cctgagtcaa atttcagcag acttaccagc atttgtatca gtggtagcaa atgaagccaa    240

actgtatctt gaaaaacctg ttgttccttt aaatatgatg ttgccacaag ctgcattgga    300

gactcattgc agtaatattt ccaatgtgcc acctacaaga gagatacttc aagtctttct    360

tactgatgta cacatgaagg aagtaattca gcagtt                              396


<210> SEQ ID NO 151
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 151

acaaaatgcc cagcctacag agtctgagaa ggaaatttat aatcaggtga atgtagtatt     60

aaaagatgca gaaggcatct tggaggactt gcagtcatac agaggagctg gccacgaaat    120

acgagaggca atccagcatc cagcanatga gaagttgcaa gagaaggcat ggggtgcagt    180

tgttccacta gtaggcaaat taaagaaatt ttacgaattt tctcagaggt tagaagcagc    240

attaagaggt cttctgggag ccttaacaag taccccatat tctcccaccc agcatctana    300

gcgagagcag gctcttgcta aacagtttgc anaaattctt catttcacac tccggtttga    360

tgaactcaag atgacaaatc ctgccataca gaatga                              396


<210> SEQ ID NO 152
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 152

acgcagcgct cggcttcctg gtaattcttc acctcttttc tcagctccct gcagcatggg     60

tgctgggccc tccttgctgc tcgccgccct cctgctgctt ctctccggcg acggcgccgt    120

gcgctgcgac acacctgcca actgcaccta tcttgacctg ctgggcacct gggtcttcca    180

ggtgggctcc agcggttccc agcgcgatgt caactgctcg gttatgggac cacaagaaaa    240

aaaagtagng gtgtaccttc agaagctgga tacagcatat gatgaccttg gcaattctgg    300

ccatttcacc atcatttaca accaaggctt tgagattgtg ttgaatgact acaagtggtt    360

tgcctttttt aagtataaag aagagggcag caaggt                              396


<210> SEQ ID NO 153
<211> LENGTH: 396
<212> TYPE: DNA
<213> ORGANISM: Homo sapien

<400> SEQUENCE: 153

ccagagacaa cttcgcggtg tggtgaactc tctgaggaaa aacacgtgcg tggcaacaag     60

tgactgagac ctagaaatcc aagcgttgga ggtcctgagg ccagcctaag tcgcttcaaa    120

atggaacgaa ggcgtttgcg ggttccatt cagagccgat acatcagcat gagtgtgtgg     180

acaagcccac ggagacttgt ggagctggca gggcagagcc tgctgaagga tgaggccctg    240
```

-continued

```
gccattgccg ccctggagtt gctgcccagg gagctcttcc cgccactctt catggcagcc    300

tttgacggga gacacagcca gaccctgaag gcaatggtgc aggcctggcc cttcacctgc    360

ctccctctgg gagtgctgat gaagggacaa catctt                              396


<210> SEQ ID NO 154
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 154

acagcaaacc tcctcacagc ccactggtcc tcaagagggg cnacntcttc acacatcanc     60

acaactacgc attgcctccc tncactcgga aggactatcc tgctgccaag agggtcaagt    120

tggacagtgt cagagtcctg agacagatca gcaacaaccg aaaatgcacc agccccaggt    180

cctcggacac cgaggagaat gtcaagaggc gaacacacaa cgtcttggag cgccagagga    240

ggaacgagct aaaacggagc ttttttgccc tgcgtgacca gatcccggag ttggaaaaca    300

atgaaaaggc ccccaaggta gttatcctta aaaaagccac agcatacatc ctgtccgtcc    360

aagcagagga gcaaaagctc atttctgaag aggact                              396


<210> SEQ ID NO 155
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 155

ttttttttt tgaananaca ggtctttaat gtacggagtc tcacaaggca caaacaccct     60

caccaggacc aaataaataa ctccacggtt gcaggaaggc gcggtctggg gaggatgcgg    120

catctgagct ctcccagggc tggtgggcga gccgggggtc tgcagtctgt gaggggcctc    180

ctgggtgtgt ccgggcctct anagcgggtc cagtctccag gatggggatc gctcactcac    240

tctccgagtc ggagtagtcc gccacgaggg aggagccgan actgcagggg tgccgcgtgt    300

cgggggtgtc agctgcctcc tgggaggagc ctgctggcna caggggcttg tcctgacggc    360

tcccttcctg ccccctcggg ctgctgcact tggggg                              396


<210> SEQ ID NO 156
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 156

gaagggggc ngggcagggg cggaatgtan anattantgc catgattgaa gatttaagaa     60

acgtgagatt caggattttc accacatccc catttagtta gcttgctcgt ttggctggtg    120

caaatgccag atggattatg aacaatgaca gtaaattaat gcaacataat caggtaatga    180

tgccaagcgt atctggtgtt ccaggtattg tacctttacc ggaacaaatc agtaaatcca    240
```

-continued

```
caatccctgg cacctgttag gcagctatta acctagtaaa tgctccccca tcccatctca    300

atcagcaang acaatcaaaa acatttgctt tnagtggcag gaacactggt acatttttac    360

ttgctccaag ggctgtgcca acgctccctc tctctg                              396
```

<210> SEQ ID NO 157
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 157

```
tttttttttt tttttgggga atgtaaatct tttattaaaa cagttgtctt tccacagtag     60

taaagctttg gcacatacag tataaaaaat aatcacccac cataattata ccaaattcct    120

nttatcaact gcatactaag tgttttcaat acaatttttt ccgtataaaa atactgggaa    180

aaattgataa ataacaggta ananaaagat atttctaggc aattactagg atcatttgga    240

aaaagtgagt actgnggata tttaaaatat cacagtaaca agatcatgct tgttcctaca    300

gtattgcggg ccanacactt aagtgaaagc anaagtgttt gggtgacttt cctacttaaa    360

attttggnca tatcatttca aaacatttgc atcttg                              396
```

<210> SEQ ID NO 158
<211> LENGTH: 396
<212> TYPE: DNA
<213> ORGANISM: Homo sapien

<400> SEQUENCE: 158

```
tttccgaaga cgggcagctt cagagaagag gattattcgg gagattgctg gtgtggccca     60

tagactcttt ggcatagact ctttcgcagg cagccactct gagtgtggcc agttctataa    120

ccatccccaa actagctgga gcctgatgga taggaacggg tagtctgtcc tcttccccat    180

aaaaatgttc caaaaagtta tctccagaga gagtccctta tgaagacagt tgccaagctg    240

tattctcatt ctttaaacca atacccaggt cagggctagt tcacactagc actgttaggg    300

acatggtgtg gctagaaatg aattgagtgt gacttctccc tacaacccca ggcccaggga    360

taggaggagg cagaggggtg cctggagttt ctgcac                              396
```

<210> SEQ ID NO 159
<211> LENGTH: 396
<212> TYPE: DNA
<213> ORGANISM: Homo sapien

<400> SEQUENCE: 159

```
tccgcgcgtt gggaggtgta gcgcggctct gaacgcgctg agggccgttg agtgtcgcag     60

gcggcgaggg cgcgagtgag gagcagaccc aggcatcgcg cgccgagaag gccgggcgtc    120

cccacactga aggtccggaa aggcgacttc cgggggcttt ggcacctggc ggaccctccc    180

ggagcgtcgg cacctgaacg cgaggcgctc cattgcgcgt gcgcgttgag ggcttcccg     240

cacctgatcg cgagacccca acggctggtg gcgtcgcctg cgcgtctcgg ctgagctggc    300

catggcgcag ctgtgcgggc tgaggcggag ccgggcgttt ctcgccctgc tgggatcgct    360

gctcctctct ggggtcctgg cggccgaccg agaacg                              396
```

<210> SEQ ID NO 160
<211> LENGTH: 396

-continued

<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 160
ggaaaccttc tcaactaaga gaacatcatt tctggcaaac tatttttgtt agctcacaat 60
atatgtcgta cactctacaa tgtaaatagc actganccac ancttacaga aggtaaaaag 120
angnataana acttccttta caaaanantt cctgttgttc ttaatactcc ccattgctta 180
tganaattnt ctatangtct ctcangantg ttcgcaccca tttcttttnt aacttctact 240
aaaaanccat ttacattgna nagtgtacna cntatatttg ngagctaaca aaaaatngtt 300
ttccnganat gatgttcttt tagtttnaga nggttcnnnc aanttnctac tccngcccgc 360
cactgnncnc cacatttnnn naattacacc ncacng 396

<210> SEQ ID NO 161
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 161
tttttgtttg attattttta ttataatgaa attaaactta tgactattac agtatgctca 60
gcttaaaaca tttatgagta ctgcaaggac taacagaaac aggaaaaatc ctactaaaaa 120
tatttgttga tgggaaatca ttgtgaaagc aaacctccaa atattcattt gtaagccata 180
agaggataag cacaaccata tgggaggaga taaccagtct ctcccttcat atatattctt 240
ttttatttct tggtatacct tcccaaaaca nanacattca acagtagtta gaatggccat 300
ctcccaacat tttaaaaaaa ctgcnccccc caatgggtga acaaagtaaa gagtagtaac 360
ctanagttca gctgagtaag ccactgtgga gcctta 396

<210> SEQ ID NO 162
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 162
tttttttttt tttttttttt tttttttttt ttnggggncc aaattttttt ntttgaagga 60
angggacaaa nnaaaaaact taaggggntg ttttggnncn acttanaaaa aagggaaagg 120
aaaccccaac atgcatgccc tnccttgggg accanggaan ncnccccncn ggtntgggga 180
aantaacccn aggnttaact ttnattatca ctgncnccca gggggggctt nnaaaaaaaa 240
nnttccccca anccaaantn gggnncnccc attttncnca anttggncnc cnggncnccc 300 natttttga ngggtttcnc cngcncattn agggaanggg nntcaannaa accncncaaa 360
ngggggnnat ttttntcang ggccnatttg ngcnnt 396

<210> SEQ ID NO 163
<211> LENGTH: 396
<212> TYPE: DNA

-continued

<213> ORGANISM: Homo sapien

<400> SEQUENCE: 163
cactgtccgg ctctaacaca gctattaagt gctacctgcc tctcaggcac tctcctcgcc 60
cagtttctga ggtcagacga gtgtctgcga tgtcttcccg cactctattc ccccagcctc 120
tttctgcttt catgctcagc acatcatctt cctaggcagt ctcttcccca aagtctcacc 180
ttttcttcca atagaaaatt ccgcttgacc tttggtgcac tgcccacttc ccagctccac 240
tggcccaagt ctgagccgga ggcccttgtt ttgggggcgg ggggagagtt ggatgtgatt 300
gcccttgaag aacaaggctg acctgagagg ttcctggcgc cctgaggtgg ctcagcacct 360
gcccagggta ggcctggcat gaggggttag gtcagc 396

<210> SEQ ID NO 164
<211> LENGTH: 396
<212> TYPE: DNA
<213> ORGANISM: Homo sapien

<400> SEQUENCE: 164
gacacgcggc ggtgtcctgt gttggccatg gccgactacc tgattagtgg gggcacgtcc 60
tacgtgccag acgacggact cacagcacag cagctcttca actgcggaga cggcctcacc 120
tacaatgact ttctcattct ccctgggtac atcgacttca ctgcagacca ggtggacctg 180
acttctgctc tgaccaagaa aatcactctt aagaccccac tggtttcctc tcccatggac 240
acagtcacag aggctgggat ggccatagca atggcgctta caggcggtat tggcttcatc 300
caccacaact gtacacctga attccaggcc aatgaagttc ggaaagtgaa gaaatatgaa 360
cagggattca tcacagaccc tgtggtcctc agcccc 396

<210> SEQ ID NO 165
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 165
tttttttttt tttttttttt ttttttcang ggncactgag gctttttatt ttgancncaa 60
aaccnccggg gatctancct gnggccnccc cggaaatnac ncnaggctca catnactnta 120
aacncttggg ggaaagggag gcaaaaaaaa caatgacttg ggccaattnc ncnactgcaa 180
agntananct gccaacaggg ctccagggag cttggnttnt gtaaaanttn taaggaagcg 240
gnncnaactc cncggggggg gggcnctaac tancagggac ccctgcaagn gttggncggg 300
ggcctcaacc tgcctgagct nacncaaggg gnggggtntn tntanccaac aggggaccna 360
agggcttgcc tncccacagn ttacttggcc aagggg 396

<210> SEQ ID NO 166
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 166 tttttcaaa ttcagagcat ttttattaaa agaacaaaat attaaggcac aaaatacatc 60

-continued aatttttcaa atgaaaaccc ttcaaacggt tatgtcctac attcaacgaa acttcttcca 120
aattacggaa taatttaact ttttaaaata naaaaataca agttcttaaa tgcctaaaat 180
ttctccccaa ataaatgttt tcttagtttt aatgaagtct cttcatgcag tactgagctc 240
caatattata atgtncactt ccttaaaaat ctagttttgc cacttatata cattcaatat 300
gtttaaccag tatattaacc agtatattaa ccaatatgtt aaacttcttt taagtataag 360
gcttggtatt ttgtattgct tattgcatgc tttgat 396

<210> SEQ ID NO 167
<211> LENGTH: 396
<212> TYPE: DNA
<213> ORGANISM: Homo sapien

<400> SEQUENCE: 167
tggcggcagc ggcggtggcg gtggctgagc agaggacccg gcgggcggcc tcgcgggtca 60
ggacacaatg tttgcacgag gactgaagag gaaatgtgtt ggccacgagg aagacgtgga 120
gggagccctg gccggcttga agacagtgtc ctcatacagc ctgcagcggc agtcgctcct 180
ggacatgtct ctggtgaagt tgcagctttg ccacatgctt gtggagccca atctgtgccg 240
ctcagtcctc attgccaaca cggtccggca gatccaagag gagatgacgc aggatgggac 300
gtggcgcaca gtggcacccc aggctgcaga gcgggcgccg ctcgaccgct tggtctccac 360
ggagatcctg tgccgtgcag cgtgggggca agaggg 396

<210> SEQ ID NO 168
<211> LENGTH: 396
<212> TYPE: DNA
<213> ORGANISM: Homo sapien

<400> SEQUENCE: 168
taggatggta agagtattat aaggattggt acaaggcatg atgagtcctt ttgcttttag 60
gcttttgact tctggtttta gactttcttt agcttctgtt gttagacaac attgtgcaag 120
cttggttttt ataagtttgc atggattaaa ctgaacttaa tgaaattgtc cctcccccca 180
aattctcagc acaattttta ggcccacaag gagtcaagca cctcaaggag atcttcagtt 240
tgaacttggt gtagacacag ggatactgat gaatcaatat tcaaattagc tgttacctac 300
ttaagaaaga gaggagacct tggggatttc gaggaagggt tcataaggga gattttagct 360
gagaaatacc atttgcacag tcaatcactt ctgacc 396

<210> SEQ ID NO 169
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 169
tttttttttt tttcanaatt aaattcttta atacaaaatg cttttttttt tttaaaanat 60
atctgtattt ctttgncgtt gttnaaaaat aaatatgtnc tacggaatat ntcnaaaaac 120
tgcnctaaaa acaaanacgn gatgttaata tcttttcccc ncaattntta cggataaaca 180
gtanccccna taaataaatg atancnaatn ttaaaattaa aaaagganan anatttagta 240
tgnaaaattc tctatttttt cttggtttgg ttttncntat aaaaaacana atagcaatgt 300

-continued ntnttttatc anaatcccnt ntntncctaa acnttttttt ttttntttnc ccccnaatnc 360
aagnngccaa anatntntnt agnatgnana tgtntn 396

<210> SEQ ID NO 170
<211> LENGTH: 396
<212> TYPE: DNA
<213> ORGANISM: Homo sapien

<400> SEQUENCE: 170
tgagaagtac catgccgctt ctgcagagga acaggcaacc atcgaacgca acccctacac 60
catcttccat caagcactga aaaactgtga gcctatgatt gggctggtac ccatcctcaa 120
gggaggccgt ttctaccagg tccctgtacc cctacccgac cggcgtcgcc gcttcctagc 180
catgaagtgg atgatcactg agtgccggga taaaaagcac cagcggacac tgatgccgga 240
gaagctgtca cacaagctgc tggaggcttt ccataaccag ggccccgtga tcaagaggaa 300
gcatgacttg cacaagatgg cagaggccaa ccgtgccctg gcccactacc gctggtggta 360
gagtctccag gaggagccca gggccctctg cgcaag 396

<210> SEQ ID NO 171
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 171
ggtcctcgtc gtggtgagcg cagccactca ggctggtcct gggggtgggg ctgtagggga 60
aagtgctaaa gccgctgagt gaagtaagaa ctctgctaga gaggaaaatg ggcttgcttt 120
catcatcatc ctnctcagct ggtggggtca agtgggaagt tctgtcactg ggatctggtt 180
cagtgtctca agaccttgcc ccaccacgga aagccttttt cacntacccc aaaggacttg 240
gagagatgtt agaagatggn tctnaaaanat tcctctgcna atntgttttt agctatcaag 300
tggcttcccc ccttaancag gnaaaacatg atcagcangt tgctcggatg gaaaaactan 360
cttggtttgn naaaaaanct ggaggcttga caatgg 396

<210> SEQ ID NO 172
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 172
agccttgggc caccctcttg gagcatctgg ctgtcgaatt cttgtgaccc tgttacacac 60
actggagaga atgggcagaa gtcgtggtgt tgcagccctg tgcattgggg gtgggatggg 120
aatagcaatg tgtgttcaga gagaatgaat tgcttaaact ttgaacaacc tcaatttctt 180
tttaaactaa taaagtacta ggttgcaata tgtgaaaaaa aaaaaaaaag ggcggccgnt 240
cnantntana gggcccnttn aaacccgttg atcaacctcg actgtgcctt ctagttgcca 300
gccatctgtt gttngcccct cccccgtgnc tttcttgacc ttgaaagggg ccccnccccct 360 gtctttccta anaaaaanga agaantnncc ttccnt 396

-continued

<210> SEQ ID NO 173
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 173
aagcatgtgg atatgtttag ctacgtttac tcacagccag cgaactgaca ttaaaataac 60
taacaaacag attcttttat gtgatgctgg aactcttgac agctataatt attattcaga 120
aatgactttt tgaaagtaaa agcagcataa agaatttgtc acaggaaggc tgtctcagat 180
aaattatggt aaaattttgc aggggacann ctttttaaga cttgcacaat tnccggatcc 240
tgcnctgact ttggaaaagg catatatgtn ctagnggcat gganaatgcc ccatactcat 300
gcatgcaaat taaacaacca agtttgaatc tttttggggg ngngctatnc tttaacccng 360
tacnggcntt attatntaan gnccctgnnn cntgtg 396

<210> SEQ ID NO 174
<211> LENGTH: 924
<212> TYPE: DNA
<213> ORGANISM: Homo sapiens

<400> SEQUENCE: 174 ctgacgacc cggcgacggc gacgtctctt ttgactaaaa gacagtgtcc agtgctccag 60 ctaggagtc tacggggacc gcctcccgcg ccgccaccat gcccaacttc tctggcaact 120 gaaaatcat ccgatcggaa aacttcgagg aattgctcaa agtgctgggg gtgaatgtga 180 gctgaggaa gattgctgtg gctgcagcgt ccaagccagc agtggagatc aaacaggagg 240 agacacttt ctacatcaaa acctccacca ccgtgcgcac cacagagatt aacttcaagg 300 tggggagga gtttgaggag cagactgtgg atgggaggcc ctgtaagagc ctggtgaaat 360 ggagagtga gaataaaatg gtctgtgagc agaagctcct gaagggagag ggccccaaga 420 ctcgtggac cagagaactg accaacgatg gggaactgat cctgaccatg acggcggatg 480 cgttgtgtg caccagggtc tacgtccgag agtgagtggc cacaggtaga accgcggccg 540 agcccacca ctggccatgc tcaccgccct gcttcactgc cccctccgtc ccacccccctc 600 ttctaggat agcgctcccc ttaccccagt cacttctggg ggtcactggg atgcctcttg 660
cagggtcttg ctttctttga cctcttctct cctcccctac accaacaaag aggaatggct 720
gcaagagccc agatcaccca ttccgggttc actccccgcc tccccaagtc agcagtccta 780
gccccaaacc agcccagagc agggtctctc taaaggggac ttgagggcct gagcaggaaa 840
gactggccct ctagcttcta ccctttgtcc ctgtagccta tacagtttag aatatttatt 900
tgttaatttt attaaaatgc ttta 924

<210> SEQ ID NO 175
<211> LENGTH: 3321
<212> TYPE: DNA
<213> ORGANISM: Homo sapiens

<400> SEQUENCE: 175 tgaagattt tgatacttgg tatttttctg tttttatgta gtaccccagc ctgggcgaaa 60 aaaagcatt attacattgg aattattgaa acgacttggg attatgcctc tgaccatggg 120 aaaagaaac ttatttctgt tgacacggaa cattccaata tctatcttca aaatggccca 180

-continued

```
atagaattg ggagactata taagaaggcc ctttatcttc agtacacaga tgaaaccttt     240
aggacaacta tagaaaaacc ggtctggctt gggtttttag gccctattat caaagctgaa    300
actggagata aagtttatgt acacttaaaa aaccttgcct ctaggcccta cacctttcat    360
tcacatggaa taacttacta taaggaacat gagggggcca tctaccctga taacaccaca    420
gattttcaaa gagcagatga caaagtatat ccaggagagc agtatacata catgttgctt    480
gccactgaag aacaaagtcc tggggaagga gatggcaatt gtgtgactag gatttaccat    540
tcccacattg atgctccaaa agatattgcc tcaggactca tcggaccttt aataatctgt    600
aaaaaagatt ctctagataa agaaaaagaa aaacatattg accgagaatt tgtggtgatg    660
ttttctgtgg tggatgaaaa tttcagctgg tacctagaag acaacattaa aacctactgc    720
tcagaaccag agaaagttga caaagacaac gaagacttcc aggagagtaa cagaatgtat    780
tctgtgaatg gatacacttt tggaagtctc ccaggactct ccatgtgtgc tgaagacaga    840
gtaaaatggt acctttttgg tatgggtaat gaagttgatg tgcacgcagc tttctttcac    900
gggcaagcac tgactaacaa gaactaccgt attgacacaa tcaacctctt tcctgctacc    960
ctgtttgatg cttatatggt ggcccagaac cctggagaat ggatgctcag ctgtcagaat   1020
ctaaaccatc tgaaagccgg tttgcaagcc tttttccagg tccaggagtg taacaagtct   1080
tcatcaaagg ataatatccg tgggaagcat gttagacact actacattgc cgctgaggaa   1140
atcatctgga actatgctcc ctctggtata gacatcttca ctaaagaaaa cttaacagca   1200
cctggaagtg actcagcggt gtttttgaa caaggtacca caagaattgg aggctcttat    1260
aaaaagctgg tttatcgtga gtacacagat gcctccttca caaatcgaaa ggagagaggc   1320
cctgaagaag agcatcttgg catcctgggt cctgtcattt gggcagaggt gggagacacc   1380
atcagagtaa ccttccataa caaaggagca tatcccctca gtattgagcc gattggggtg   1440
agattcaata agaacaacga gggcacatac tattccccaa attacaaccc ccagagcaga   1500
agtgtgcctc cttcagcctc ccatgtggca cccacagaaa cattcaccta tgaatggact   1560
gtccccaaag aagtaggacc cactaatgca gatcctgtgt gtctagctaa gatgtattat   1620
tctgctgtgg atcccactaa agatatattc actgggctta ttgggccaat gaaaatatgc   1680
aagaaaggaa gtttacatgc aaatgggaga cagaaagatg tagacaagga attctatttg   1740
tttcctacag tatttgatga gaatgagagt ttactcctgg aagataatat tagaatgttt   1800
acaactgcac ctgatcaggt ggataaggaa gatgaagact ttcaggaatc taataaaatg   1860
cactccatga atggattcat gtatgggaat cagccgggtc tcactatgtg caaaggagat   1920
tcggtcgtgt ggtacttatt cagcgccgga aatgaggccg atgtacatgg aatatacttt   1980
tcaggaaaca catatctgtg gagaggagaa cggagagaca cagcaaacct cttccctcaa   2040
acaagtctta cgctccacat gtggcctgac acagagggga cttttaatgt tgaatgcctt   2100
acaactgatc attacacagg cggcatgaag caaaaatata ctgtgaacca atgcaggcgg   2160
cagtctgagg attccacctt ctacctggga gagaggacat actatatcgc agcagtggag   2220
gtggaatggg attattcccc acaaagggag tgggaaaagg agctgcatca tttacaagag   2280
cagaatgttt caaatgcatt tttagataag ggagagtttt acataggctc aaagtacaag   2340
aaagttgtgt atcggcagta tactgatagc acattccgtg ttccagtgga gagaaaagct   2400
gaagaagaac atctgggaat tctaggtcca caacttcatg cagatgttgg agacaaagtc   2460
aaaattatct ttaaaaacat ggccacaagg ccctactcaa tacatgccca tggggtacaa   2520
acagagagtt ctacagttac tccaacatta ccaggtgaaa ctctcactta cgtatggaaa   2580
```

-continued

```
atcccagaaa gatctggagc tggaacagag gattctgctt gtattccatg ggcttattat   2640

tcaactgtgg atcaagttaa ggacctctac agtggattaa ttggccccct gattgtttgt   2700

cgaagacctt acttgaaagt attcaatccc agaaggaagc tggaatttgc ccttctgttt   2760

ctagtttttg atgagaatga atcttggtac ttagatgaca acatcaaaac atactctgat   2820

caccccgaga aagtaaacaa agatgatgag gaattcatag aaagcaataa aatgcatgct   2880

attaatggaa gaatgtttgg aaacctacaa ggcctcacaa tgcacgtggg agatgaagtc   2940

aactggtatc tgatgggaat gggcaatgaa atagacttac acactgtaca ttttcacggc   3000

catagcttcc aatacaagca caggggagtt tatagttctg atgtctttga cattttccct   3060

ggaacatacc aaaccctaga aatgtttcca agaacacctg gaatttggtt actccactgc   3120

catgtgaccg accacattca tgctggaatg gaaaccactt acaccgttct acaaaatgaa   3180

gacaccaaat ctggctgaat gaaataaatt ggtgataagt ggaaaaaaga gaaaaaccaa   3240

tgattcataa caatgtatgt gaaagtgtaa aatagaatgt tactttggaa tgactataaa   3300

cattaaaaga gactggagca t                                              3321
```

<210> SEQ ID NO 176
<211> LENGTH: 487
<212> TYPE: DNA
<213> ORGANISM: Homo sapiens

<400> SEQUENCE: 176

```
gaaatacttt ctgtcttatt aaaattaata aattattggt ctttacaaga cttggataca     60

ttacagcaga catggaaata taattttaaa aaatttctct ccaacctcct tcaaattcag    120

tcaccactgt tatattacct tctccaggaa ccctccagtg gggaaggctg cgatattaga    180

tttccttgta tgcaaagttt ttgttgaaag ctgtgctcag aggaggtgag aggagaggaa    240

ggagaaaact gcatcataac tttacagaat tgaatctaga gtcttccccg aaaagcccag    300

aaacttctct gcagtatctg gcttgtccat ctggtctaag gtggctgctt cttccccagc    360

catgagtcag tttgtgccca tgaataatac acgacctgtt atttccatga ctgctttact    420

gtatttttaa ggtcaatata ctgtacattt gataataaaa taatattctc ccaaaaaaaa    480

aaaaaaa                                                              487
```

<210> SEQ ID NO 177
<211> LENGTH: 3999
<212> TYPE: DNA
<213> ORGANISM: Homo sapiens

<400> SEQUENCE: 177

```
caagattcca catttgatgg ggtgactgac aaacccatct tagactgctg tgcctgcgga     60

actgccaagt acagactcac attttatggg aattggtccg agaagacaca cccaaaggat    120

taccctcgtc gggccaacca ctggtctgcg atcatcggag gatcccactc caagaattat    180

gtactgtggg aatatggagg atatgccagc gaaggcgtca aacaagttgc agaattgggc    240

tcacccgtga aaatggagga agaaattcga caacagagtg atgaggtcct caccgtcatc    300

aaagccaaag cccaatggcc agcctggcag cctctcaacg tgagagcagc accttcagct    360

gaattttccg tggacagaac gcgccattta atgtccttcc tgaccatgat gggccctagt    420

cccgactgga acgtaggctt atctgcagaa gatctgtgca ccaaggaatg tggctgggtc    480

cagaaggtgg tgcaagacct gattccctgg gacgctggca ccgacagcgg ggtgacctat    540
```

-continued

```
gagtcaccca acaaacccac cattccccag gagaaaatcc ggcccctgac cagcctggac    600
catcctcaga gtcctttcta tgacccagag ggtgggtcca tcactcaagt agccagagtt    660
gtcatcgaga gaatcgcacg gaagggtgaa caatgcaata ttgtacctga caatgtcgat    720
gatattgtag ctgacctggc tccagaagag aaagatgaag atgacacccc tgaaacctgc    780
atctactcca actggtcccc atggtccgcc tgcagctcct ccacctgtga caaaggcaag    840
aggatgcgac agcgcatgct gaaagcacag ctggacctca gcgtcccctg ccctgacacc    900
caggacttcc agccctgcat gggccctggc tgcagtgacg aagacggctc cacctgcacc    960
atgtccgagt ggatcacctg gtcgccctgc agcatctcct gcggcatggg catgaggtcc   1020
cgggagaggt atgtgaagca gttcccggag gacggctccg tgtgcacgct gcccactgag   1080
gaaacggaga agtgcacggt caacgaggag tgctctccca gcagctgcct gatgaccgag   1140
tggggcgagt gggacgagtg cagcgccacc tgcggcatgg gcatgaagaa gcggcaccgc   1200
atgatcaaga tgaaccccgc agatggctcc atgtgcaaag ccgagacatc acaggcagag   1260
aagtgcatga tgccagagtg ccacaccatc ccatgcttgc tgtccccatg gtccgagtgg   1320
agtgactgca gcgtgacctg cgggaagggc atgcgaaccc gacagcggat gctcaagtct   1380
ctggcagaac ttggagactg caatgaggat ctggagcagg tggagaagtg catgctccct   1440
gaatgcccca ttgactgtga gctcaccgag tggtcccagt ggtcggaatg taacaagtca   1500
tgtgggaaag gccacgtgat tcgaacccgg atgatccaaa tggagcctca gtttggaggt   1560
gcaccctgcc cagagactgt gcagcgaaaa aagtgccgca tccgaaaatg ccttcgaaat   1620
ccatccatcc aaaagctacg ctggagggag gcccgagaga gccggcggag tgagcagctg   1680
aaggaagagt ctgaagggga gcagttccca ggttgtagga tgcgcccatg gacggcctgg   1740
tcagaatgca ccaaactgtg cggaggtgga attcaggaac gttacatgac tgtaaagaag   1800
agattcaaaa gctcccagtt taccagctgc aaagacaaga aggagatcag agcatgcaat   1860
gttcatcctt gttagcaagg gtacgagttc cccagggctg cactctagat tccagagtca   1920
ccaatggctg gattatttgc ttgtttaaga caatttaaat tgtgtacgct agttttcatt   1980
tttgcagtgt ggttcgccca gtagtcttgt ggatgccaga gacatccttt ctgaatactt   2040
cttgatgggt acaggctgag tggggcgccc tcacctccag ccagcctctt cctgcagagg   2100
agtagtgtca gccaccttgt actaagctga aacatgtccc tctggagctt ccacctggcc   2160
agggaggacg gagactttga cctactccac atggagaggc aaccatgtct ggaagtgact   2220
atgcctgagt cccagggtgc ggcaggtagg aaacattcac agatgaagac agcagattcc   2280
ccacattctc atctttggcc tgttcaatga aaccattgtt tgcccatctc ttcttagtgg   2340
aactttaggt ctcttttcaa gtctcctcag tcatcaatag ttcctgggga aaaacagagc   2400
tggtagactt gaagaggagc attgatgttg ggtggctttt gttctttcac tgagaaattc   2460
ggaatacatt tgtctcaccc ctgatattgg ttcctgatgc ccccccaaca aaaataaata   2520
aataaattat ggctgcttta tttaaatata aggtagctag tttttacacc tgagataaat   2580
aataagctta gagtgtattt ttcccttgct tttgggggtt cagaggagta tgtacaattc   2640
ttctgggaag ccagccttct gaactttttg gtactaaatc cttattggaa ccaagacaaa   2700
ggaagcaaaa ttggtctctt tagagaccaa tttgcctaaa ttttaaaatc ttcctacaca   2760
catctagacg ttcaagtttg caaatcagtt tttagcaaga aaacattttt gctatacaaa   2820
cattttgcta agtctgccca aagccccccc aatgcattcc ttcaacaaaa tacaatctct   2880
gtactttaaa gttattttag tcatgaaatt ttatatgcag agagaaaaag ttaccgagac   2940
```

-continued

```
agaaaacaaa tctaagggaa aggaatatta tgggattaag ctgagcaagc aattctggtg   3000
gaaagtcaaa cctgtcagtg ctccacacca gggctgtggt cctcccagac atgcatagga   3060
atggccacag gtttacactg ccttcccagc aattataagc acaccagatt cagggagact   3120
gaccaccaag ggatagtgta aaaggacatt ttctcagttg ggtccatcag cagtttttct   3180
tcctgcattt attgttgaaa actattgttt catttcttct tttataggcc ttattactgc   3240
ttaatccaaa tgtgtaccat tggtgagaca catacaatgc tctgaataca ctacgaattt   3300
gtattaaaca catcagaata tttccaaata caacatagta tagtcctgaa tatgtacttt   3360
taacacaaga gagactattc aataaaaact cactgggtct ttcatgtctt taagctaagt   3420
aagtgttcag aaggttcttt tttatattgt cctccacctc catcattttc aataaaagat   3480
agggcttttg ctcccttgtt cttggaggga ccattattac atctctgaac tacctttgta   3540
tccaacatgt tttaaatcct taaatgaatt gctttctccc aaaaaaagca caatataaag   3600
aaacacaaga tttaattatt tttctacttg gggggaaaaa agtcctcatg tagaagcacc   3660
cacttttgca atgttgttct aagctatcta tctaactctc agcccatgat aaagttcctt   3720
aagctggtga ttcctaatca aggacaagcc accctagtgt ctcatgtttg tatttggtcc   3780
cagttgggta cattttaaaa tcctgatttt ggagacttaa aaccaggtta atggctaaga   3840
atgggtaaca tgactcttgt tggattgtta tttttgttt gcaatgggga atttataaga    3900
agcatcaagt ctctttctta ccaaagtctt gttaggtggt ttatagttct tttggctaac   3960
aaatcatttt ggaaataaag attttttact acaaaaatg                          3999
```

<210> SEQ ID NO 178
<211> LENGTH: 1069
<212> TYPE: DNA
<213> ORGANISM: Homo sapiens

<400> SEQUENCE: 178

```
aaaaaagatg aataaatgaa taagagagat gaataaacaa atttacatta catgtgatag     60
ttatcatggt atggccttca tgacaagatg gatgagaata tcactgatag gatattagcc    120
ttctttcata tctttatatt gaaatatggg ctttacttca atttgaaggt ctttcatgaa    180
caataaaaga gagtagaagg actgtctgag aaggcaggag acatataaaa cagatgactg    240
aaagactgac tagctcctgg aaagggaaac atttggaaca tccagagtaa gggcaaatgg    300
gcttctacca gcacaacaaa gagcctccag gtggcaacat ggaagcaggt tatcagagaa    360
aataaatgtg caaattcctt atttacaatg actcacttaa ccccacaaac atgtttcact    420
gctgccttcc ccagttgtcg cttatgtact gttgttacct ttcagttaca tgcctttgat    480
cctaaaattc tctactttg gtgccttatc agttctttgc aatctgcctg tggttatcag     540
cacttaaagc acaattttga aggggaaaaa aatgataatc accttagtcc caaagaaata    600
atttgtcaaa ctgccttatt agtattaaaa acagacacac tgaatgaagt agcatgatac    660
gcatatatcc tactcagtat cattggcctt ttatcaaatg gggaaactat acttttgtat    720
tacatagttt tagaaatcga aagttagaga ctctttataa gtaatgtcaa ggaacagtaa    780
tttaaaaaca aagttctaac aaatatattg tttgcttaat cacaatgccc tcaacttgta    840
tttgaataac taaataggac atgtcttcct tggagctgtg ggcattagtt cagaagcact    900
acctgcatct taattttcaa aacttaagtt ttattagcaa atcctcttct ctgtaagact    960
tagctatgaa gtggtatatt ttttccaaat atttttctga aacatttgt tgttgtaact    1020
```

-continued gcacaataaa agtccagttg caattaaaaa aaaaaaaaaa aaaaaaaaa 1069

<210> SEQ ID NO 179
<211> LENGTH: 1817
<212> TYPE: DNA
<213> ORGANISM: Homo sapiens

<400> SEQUENCE: 179
tgctattctg ccaaaagaca atttctagag tagttttgaa tgggttgatt tcccccactc 60
ccacaaactc tgaagccagt gtctagctta ctaaaaaaag agttgtatat aatatttaag 120
atgctgagta tttcatagga aagctgaatg ctgctgtaaa gtgctcttta agtctttttt 180
ttttttaatc cccttctaat gaatgaaact aggggaattt caggggacag agatgggatt 240
tgttgtatga taaactgtat gtagttttta gtctttctgt tttgagaagc agtggttggg 300
gcatttttaa gatggctggc tactcttgtt ttccctcatg ataataaatt tgtcataact 360
cagtaacatg aacttgcccc tagaggtagt tgttaataat tttgaaatat taaggtcttg 420
ccaagcttct gatgattcac acctgtacta ctgattatta agcaggacag actgagcttt 480
ctgttgcaaa taccttggag gagaaagtaa tttctaaata tacagagagg taacttgact 540
atatatgttg catcctgtgc ctcccttcat attaatattt gataaagatt ttaatttatg 600
taaaacttct aaagcagaat caaagctcct cttggggaaa tggcaagtct ttaggatagg 660
caagaccctg tatgaatagt accaaagcat taccgcatgg tagagaacac actcgattaa 720
aaatgttaag ctatctgaaa aataaaatgt gcaagtcttc aggatggcac aaaacaaagg 780
ttaatgcttc ttggggcaca tttcttagag ggcttgctga gtgtgtaaat ataatcgact 840
tttgtttgtg ttacatgact tctgtgactt cattgaaaat ctgcacaatt cagtttcagc 900
tctggattac ttcagttgac ctttgtgaag gtttttatct gtgtagaatg ggtgtttgac 960
ttgttttagc ctattaaatt tttattttct ttcactctgt attaaaagta aaacttacta 1020
aaagaaaaga ggtttgtgtt cacattaaat ggttttggtt tggcttcttt tagtcaggct 1080
ttctgaacat tgagatatcc tgaacttaga gctcttcaat cctaagattt tcatgaaaag 1140
cctctcactt gaacccaaac cagagtactc ttactgcctc ttttctaaat gttcaggaaa 1200
agcattgcca gttcagtctt ttcaaaatga gggagaaaca tttgcctgcc ttgtaataac 1260
aagactcagt gcttattttt taaactgcat tttaaaaatt ggatagtata ataacaataa 1320
ggagtaagcc accttttata ggcaccctgt agttttatag ttcttaatct aaacatttta 1380
tatttccttc ttttggaaaa aacctacatg ctacaagcca ccatatgcac agactataca 1440
gtgagttgag ttggctctcc cacagtcttt gaggtgaatt acaaaagtcc agccattatc 1500
atcctcctga gttatttgaa atgatttttt ttgtacattt tggctgcagt attggtggta 1560
gaatatacta taatatggat catctctact tctgtattta tttatttatt actagacctc 1620
aaccacagtc ttctttttcc ccttccacct ctctttgcct gtaggatgta ctgtatgtag 1680
tcatgcactt tgtattaata tattagaaat ctacagatct gttttgtact ttttatactg 1740
ttggatactt ataatcaaaa cttttactag ggtattgaat aaatctagtc ttactagaaa 1800
aaaaaaaaaa aaaaaaa 1817

<210> SEQ ID NO 180
<211> LENGTH: 2382
<212> TYPE: DNA
<213> ORGANISM: Homo sapiens

<400> SEQUENCE: 180

-continued

```
acttttattg gaagcagcag ccacatccct gcatgatttg cattgcaata caaccataac     60
cgggcagcca ctcctgagtg ataaccagta taacataaac gtagcagcct caatttttgc    120
ctttatgacg acagcttgtt atggttgcag tttgggtctg gctttacgaa gatggcgacc    180
gtaacactcc ttagaaactg gcagtcgtat gttagtttca cttgtctact ttatatgtct    240
gatcaatttg gataccattt tgtccagatg caaaaacatt ccaaaagtaa tgtgtttagt    300
agagagagac tctaagctca agttctggtt tatttcatgg atggaatgtt aattttatta    360
tgatattaaa gaaatggcct tttattttac atctctcccc tttttccctt tcccccttta    420
ttttcctcct tttctttctg aaagtttcct tttatgtcca taaaatacaa atatattgtt    480
cataaaaaat tagtatccct tttgtttggt tgctgagtca cctgaacctt aattttaatt    540
ggtaattaca gcccctaaaa aaaacacatt tcaaataggc ttcccactaa actctatatt    600
ttagtgtaaa ccaggaattg gcacactttt tttagaatgg gccagatggt aaatatttat    660
gcttcacggt ccatacagtc tctgtcacaa ctattcagtt ctgctagtat agcgtgaaag    720
cagctataca caatacagaa atgaatgagt gtggttatgt tctaataaaa cttatttata    780
aaaacaaggg gaggctgggt ttagcctgtg ggccatagtt tgtcaaccac tggtgtaaaa    840
ccttagttat atatgatctg cattttcttg aactgatcat tgaaaactta taaacctaac    900
agaaaagcca cataatattt agtgtcatta tgcaataatc acattgcctt tgtgttaata    960
gtcaaatact tacctttgga gaatacttac ctttggagga atgtataaaa tttctcaggc   1020
agagtcctgg atataggaaa aagtaattta tgaagtaaac ttcagttgct taatcaaact   1080
aatgatagtc taacaactga gcaagatcct catctgagag tgcttaaaat gggatcccca   1140
gagaccatta accaatactg gaactggtat ctagctactg atgtcttact ttgagtttat   1200
ttatgcttca gaatacagtt gtttgccctg tgcatgaata tacccatatt tgtgtgtgga   1260
tatgtgaagc ttttccaaat agagctctca gaagaattaa gtttttactt ctaattattt   1320
tgcattactt tgagttaaat ttgaatagag tattaaatat aaagttgtag attcttatgt   1380
gtttttgtat tagcccagac atctgtaatg tttttgcact ggtgacagac aaaatctgtt   1440
ttaaaatcat atccagcaca aaaactattt ctggctgaat agcacagaaa agtattttaa   1500
cctacctgta gagatcctcg tcatggaaag gtgccaaact gttttgaatg gaaggacaag   1560
taagagtgag gccacagttc ccaccacacg agggcttttg tattgttcta ctttttcagc   1620
cctttacttt ctggctgaag catccccttg gagtgccatg tataagttgg gctattagag   1680
ttcatggaac atagaacaac catgaatgag tggcatgatc cgtgcttaat gatcaagtgt   1740
tacttatcta ataatcctct agaaagaacc ctgttagatc ttggtttgtg ataaaaatat   1800
aaagacagaa gacatgagga aaaacaaaag gtttgaggaa atcaggcata tgactttata   1860
cttaacatca gatcttttct ataatatcct actactttgg ttttcctagc tccataccac   1920
acacctaaac ctgtattatg aattacatat tacaaagtca taaatgtgcc atatggatat   1980
acagtacatt ctagttggaa tcgtttactc tgctagaatt taggtgtgag atttttttgtt  2040
tcccaggtat agcaggctta tgtttggtgg cattaaattg gtttctttaa aatgctttgg   2100
tggcactttt gtaaacagat tgcttctaga ttgttacaaa ccaagcctaa gacacatctg   2160
tgaatactta gatttgtagc ttaatcacat tctagacttg tgagttgaat gacaaagcag   2220
ttgaacaaaa attatggcat ttaagaattt aacatgtctt agctgtaaaa atgagaaagt   2280
gttggttggt tttaaaatct ggtaactcca tgatgaaaag aaatttattt tatacgtgtt   2340
```

-continued

```
atgtctctaa taaagtattc atttgataaa aaaaaaaaaa aa                  2382


<210> SEQ ID NO 181
<211> LENGTH: 2377
<212> TYPE: DNA
<213> ORGANISM: Homo sapiens

<400> SEQUENCE: 181

atctttatgc aagacaagag tcagccatca gacactgaaa tatattatga tagattatga     60

agaattttct ctgtagaatt atattcttcc tggaacctgg tagagtagat tagactcaaa    120

ggctttttct tccttttctt actcctgttt tttccactca ctcttcccaa gagatttcct    180

aaagcttcaa gcttaataag cctaatagtg aaaaataact gaatttaatg gtataatgaa    240

gttcttcatt tccagacatc tttaattgat cttaaagctc atttgagtct ttgcccctga    300

acaaagacag acccattaaa atctaagaat tctaaatttt cacaactgtt tgagcttctt    360

ttcattttga aggatttgga atatatatgt tttcataaaa gtatcaagtg aaatatagtt    420

acatgggagc tcaatcatgt gcagattgca ttctgttatg ttgactcaat atttaattta    480

caactatcct tatttatatt gacctcaaga actccatttt atgcaatgca gaccactgag    540

atatagctaa cattctttca aataattttc cttttctttt ataattcctc tatagcaaat    600

ttttatgtat aactgattat acatatccat atttatattt cattgattcc aagacatcac    660

tttttcaatt taacatctct gaaattgtga catttcttgc aactgttggc acttcagatg    720

cagtgtttaa aattatgctt gaataaatat tacactaatc caactttacc taaatgttta    780

tgcatctagg caaattttgt tttcttataa agatttgaga gcccatttat gacaaaatat    840

gaaggcgaaa tttaaggaca actgagtcac gcacaactca acatggagcc taactgatta    900

tcagctcaga tcccgcatat cttgagttta caaaagctct ttcaggtccc catttatact    960

ttacgtgagt gcgaatgatt tcagcaaacc ctaacttaac taacaagaat gggtaggtat   1020

gtctacgttt cattaacaaa tttttattat ttttattcta ttatatgaga tccttttata   1080

ttatcatctc acttttaaac aaaattaact ggaaaaatat tacatggaac tgtcatagtt   1140

aggttttgca gcatcttaca tgtcttgtat caatggcagg agaaaaatat gataaaaaca   1200

atcagtgctg tgaaaaacaa ctttcttcta gagtcctctt actttttatt cttctttatc   1260

atttgtgggt ttttcccccct tggctctcac tttaacttca agcttatgta acgactgtta   1320

taaaactgca tatttaaatt atttgaatta tatgaaataa ttgttcagct atctgggcag   1380

ctgttaatgt aaacctgaga gtaataacac tactctttta tctacctgga atacttttct   1440

gcataaaatt tatctttgta agctaactct attaatcagg tttcttctag cctctgcaac   1500

ctacttcagt tagaattgtc taatactgct ctattaatca ggtttctacc ctctacaacc   1560

tacttcagtt aaaattgtct aatacagcaa tatttaaaaa aaaaacactg caattgtcaa   1620

ggatggaaaa tgtgtgattt gtgtaaacaa tttttaccaa ctttacattt tcctacagat   1680

aaatgtgaaa ttttgataag aagtctacgc aatgacaagt acggtacata aattttatta   1740

agaatattga gtataaagta ctttaattct aaattataag aaaatataca tttgcacata   1800

ttaatataga aattcatttt gtgtatattt aacatagctt ttaaactatt ttacattagc   1860

tacttcatta tggtttcttg aacttctgaa aaaaattaga aatgtattaa acttatcagt   1920

aacataaaaa cttattttgt ttcacctaac gaatactgcg tttgtaaaaa taaatttaat   1980

atagaatata tttttaaatt aaatatttga atataaaata gctctaagaa agaagcaaat   2040

tatcactgaa catatttctt attatttctg gctttgaatt atacgtaact taaattgtct   2100
```

-continued

```
taaatgatac agaatattgg agaatatgat actttcacat aatatactat gaacctgttc   2160

atataactct gattgactac taacttctgt tttatgtatt tattaaagag ctgacactgt   2220

agtttgtggt gagatgttta tttttctaac agagcttata acagttagga caaggcattt   2280

aattaatgca tcattctgtt tagtagtagg tgttaatcaa tatgaaattc tctgttttaa   2340

aataaaaatg taaaaatcta aaaaaaaaaa aaaaaaa                            2377


<210> SEQ ID NO 182
<211> LENGTH: 1370
<212> TYPE: DNA
<213> ORGANISM: Homo sapiens

<400> SEQUENCE: 182

tgtgagcatg gtattttgtc tcggaagaaa aaaatatggg tcaggcgcaa agtaagccca     60

ccccactggg aactatgtta aaaaaaaatt tcaagattta agggagatta cggtgttact    120

atgacaccag aaaaacttag aactttgtgt gaaatagact ggctaacatt agaggtgggt    180

tggctatcag aagaaagcct ggagaggtcc cttgtttcaa aggtatggca caaggtaacc    240

tgtaagccaa agcacccgga ccagtttcta tacatagaca gttacagctg gtttagaccc    300

cttccccctc tccccacagt agttaagaga acagcagcat aagcagctgg cagaggcaag    360

gaaagaccag cagagagaaa aaaaggccat ctataccaat tttaagttaa tttagactga    420

acaagggctt attaatagca aaggataatt gaaatcacaa acttataagg gtttcaacaa    480

aagtgaagtt tgctaaaagt taacagtgta acatgtatta tggtaacttc taatcttgtg    540

gccttagaca gtctagtcaa aacacataaa gaaagtttgc tttaaaaaaa caatggttat    600

cttcaaaaat aaaggggaga ggcagaattt atataaaaag agttatatga taaattcttg    660

tcctgaaata aattaactgg ttgtttaaag aaaagaatgt ttgtaataag tcaaaaagtt    720

aaaacatgtt taaaaaattg tctgcaaaag tcataaaaga aaaaatttta ttaaaaaaat    780

tttaagcaaa aaatgttgta taatttaaaa gtaataaggc ctcctgtgta ctattaagac    840

agatgcaaat tcctggttga aatggatcaa atattccatc tgcacattaa acaaaagcaa    900

ttgttatgct tgtgcacatg gcaggccaga ggccctgatt gtccccccttc cactaaggtg    960

gtcctctagt cgaccaggcg tggactgcat ggtagctctt ttccaggatt ctacagcctg   1020

gagtaataag tcatgccaag ctctctctgc tatatcccaa agtctctgcg ggtcagcccc   1080

caagggccat gcagcttctg tctcccaaca ctaagttcac ttcgtgtctc tcacggcaga   1140

gaggaaactt agtattcctt ggagacctga agggatgcag tgagcttaag aattttcaag   1200

agcttatcaa tcagtcagcc cttgttcatc cccgagtgga tgtgtggtgg tattgtggtg   1260

gacctttact gggcactctg ccaaataact agtgtggcac ttgtgcttta gtccatttgg   1320

ctatcccttt caccctggca tttcatcaac caaaaaaaaa aaaaaaaaaa              1370


<210> SEQ ID NO 183
<211> LENGTH: 2060
<212> TYPE: DNA
<213> ORGANISM: Homo sapiens
<220> FEATURE:
<221> NAME/KEY: misc_feature
<222> LOCATION: (1)...(2060)
<223> OTHER INFORMATION: n=A,T,C or G

<400> SEQUENCE: 183

gtttcagggg aggagacaag gtttcttgtt tgccgtatat gctcctgcag agaagaggaa     60
```

-continued

```
gtgaccgtgg aggccatctg gccctgtgtt ttgatatggc aaaattaatg aatgcaatca    120

gaagaccttt gagcaagaaa gtaccctgga acaacccaat ttggactgca agtattagtt    180

gggtcttcca ggtgcctctc acagcagcag tcatggcagc agtgactcta gccatgtcca    240

tgaccaactg ctgcataaca aatagccccg agactcagca gcttacaaca gggtccccag    300

cccacagact ggcactggtc catggcttgt taggaacctg actgcgcagc agaaggtgag    360

tgagcattac tgcctgagct ctgcctcctg tcagatcatc aggggcatta gattctcata    420

ggagcgtgaa ccctattgca aaccgcgcat gcgaaggatg tacgttgcgt gctccttatg    480

agaatctaac taatgcctga tgatttgagg tggggcagtt tcatccccaa accatctctc    540

tcccttcatg tccatggaaa aattgtcttc tacaaaacca gtccgtggtg ccaaaaaggt    600

tggagactgc tggtttacaa ccgcaatgaa cattcatcat cccacacagt gtcagagggt    660

cgggaacacg ggtgccctgc ctgtgtgctt ccggttccag atttctcagt gggttgtgat    720

caaggtatca gcggaggccg tattcatctg caagcttgac caggaataga agagccactt    780

catgggtggc tcactcagat gccagcaggt cagtgctggt ggctggcagg cagcctcagc    840

tcctcacctc atggatctct cctgagcaca gttttcctgt ccttacaacc tggtagctgg    900

cttctccaga gcaggtgact caggagagga caaggtgaga gcccagcacc ttatggtcta    960

gtctcagaag tcacacgcca tcatttctgc aatgtcattt tggggttcca ggtcagctgt   1020

atcactgtgg gaggtgagta tatagatgtc ctagaccatt caggctgcta tgacagaaca   1080

ccatgaactg agtggctcat gaacaacaga aatttcccac agttctgtag gctgggaaat   1140

ccaagatcaa ggtggcagca ggttcagcgt ctgctaagct cctgcttttc atggattgca   1200

tcttctcact gtgtcctcac gtgatggaca gagcaaatga gctctcaggc actagtccca   1260

gccatgagga ctctgctttc atgactcatc actccgcaaa ggcccacctc catcagaaga   1320

cagctgctaa ctgcagctgc catcctccaa gacgggagac acagaattgg gggacatata   1380

cattgagatc tgaaaggcct ggacagcaac aggtggggat cgtgggggca tcttggaggg   1440

tggctgccgc agtaacattt ctgacccatg ctttctgctt gcactcatct cctgcctttg   1500

atcttcatta tctcargcag tccccacaac gactgtatct aggagttcat tttaccctca   1560

ttttacagat gaaacgtctc agagggtaat gtgcttgccc agtgtctcac aaatgcaaag   1620

tcactgaggt aggatttcaa cctaggtcca atcatctctg cagcattagg ggttcaccat   1680

tgccatagac ttaactgtgt cccccaaaat ttgtatgttg aagccctacc agcctccccc   1740

ccccaatgtg ctgatgtttg gagaaagggc ctttgggagg taattaggtt tagatgagat   1800

catgagggtg ggactctcat aatggcatta atgccatcag gtgaagagat accagagacc   1860

ttgtgtcctc tctctctgca atgtgaggac acagtgagaa ggcagctgtc tgcaagctgg   1920

gaagagagta ctgaccagga acttaatcag agggcatctt gatcttggac ttcccagcct   1980

ccagaactct gaaaagttaa tgnctattat ttaagccacg cagtctatgg aattttgtta   2040

gagccaaccc caagcttact                                               2060


<210> SEQ ID NO 184
<211> LENGTH: 3079
<212> TYPE: DNA
<213> ORGANISM: Homo sapiens

<400> SEQUENCE: 184

ggcacaaagt tgggggccgc gaagatgagg ctgtccccgg cgcccctgaa gctgagccgg     60

actccggcac tgctggccct ggcgctgccc ctggccgcgg cgctggcctt ctccgacgag    120
```

-continued

```
accctggaca aagtgcccaa gtcagagggc tactgtagcc gtatcctgcg cgcccagggc    180
acgcggcgcg agggctacac cgagttcagc ctccgcgtgg agggcgaccc cgacttctac    240
aagccgggaa ccagctaccg cgtaacactt tcagctgctc ctccctccta cttcagagga    300
ttcacattaa ttgccctcag agagaacaga gagggtgata aggaagaaga ccatgctggg    360
accttccaga tcatagacga agaagaaact cagtttatga gcaattgccc tgttgcagtc    420
actgaaagca ctccacggag gaggacccgg atccaggtgt tttggatagc accaccagcg    480
ggaacaggct gcgtgattct gaaggccagc atcgtacaaa aacgcattat ttattttcaa    540
gatgagggct ctctgaccaa gaaactttgt gaacaagatt ccacatttga tggggtgact    600
gacaaaccca tcttagactg ctgtgcctgc ggaactgcca agtacagact cacattttat    660
gggaattggt ccgagaagac acacccaaag gattaccctc gtcgggccaa ccactggtct    720
gcgatcatcg gaggatccca ctccaagaat tatgtactgt gggaatatgg aggatatgcc    780
agcgaaggcg tcaaacaagt tgcagaattg ggctcacccg tgaaaatgga ggaagaaatt    840
cgacaacaga gtgatgaggt cctcaccgtc atcaaagcca aagcccaatg gccagcctgg    900
cagcctctca acgtgagagc agcaccttca gctgaatttt ccgtggacag aacgcgccat    960
ttaatgtcct tcctgaccat gatgggccct agtcccgact ggaacgtagg cttatctgca   1020
gaagatctgt gcaccaagga atgtggctgg gtccagaagg tggtgcaaga cctgattccc   1080
tgggacgctg gcaccgacag cggggtgacc tatgagtcac ccaacaaacc caccattccc   1140
caggagaaaa tccggcccct gaccagcctg gaccatcctc agagtccttt ctatgaccca   1200
gagggtgggt ccatcactca agtagccaga gttgtcatcg agagaatcgc acggaagggt   1260
gaacaatgca atattgtacc tgacaatgtc gatgatattg tagctgacct ggctccagaa   1320
gagaaagatg aagatgacac ccctgaaacc tgcatctact ccaactggtc cccatggtcc   1380
gcctgcagct cctccacctg tgacaaaggc aagaggatgc gacagcgcat gctgaaagca   1440
cagctggacc tcagcgtccc ctgccctgac acccaggact tccagccctg catgggccct   1500
ggctgcagtg acgaagacgg ctccacctgc accatgtccg agtggatcac ctggtcgccc   1560
tgcagcatct cctgcggcat gggcatgagg tcccgggaga ggtatgtgaa gcagttcccg   1620
gaggacggct ccgtgtgcac gctgcccact gaggaaatgg agaagtgcac ggtcaacgag   1680
gagtgctctc ccagcagctg cctgatgacc gagtggggcg agtgggacga gtgcagcgcc   1740
acctgcggca tgggcatgaa gaagcggcac cgcatgatca agatgaaccc cgcagatggc   1800
tccatgtgca aagccgagac atcacaggca gagaagtgca tgatgccaga gtgccacacc   1860
atcccatgct tgctgtcccc atggtccgag tggagtgact gcagcgtgac ctgcgggaag   1920
ggcatgcgaa cccgacagcg gatgctcaag tctctggcag aacttggaga ctgcaatgag   1980
gatctggagc aggtggagaa gtgcatgctc cctgaatgcc ccattgactg tgagctcacc   2040
gagtggtccc agtggtcgga atgtaacaag tcatgtggga aaggccacgt gattcgaacc   2100
cggatgatcc aaatggagcc tcagtttgga ggtgcaccct gcccagagac tgtgcagcga   2160
aaaaagtgcc gcatccgaaa atgccttcga aatccatcca tccaaaagcc acgctggagg   2220
gaggcccgag agagccggcg gagtgagcag ctgaaggaag agtctgaagg ggagcagttc   2280
ccaggttgta ggatgcgccc atggacggcc tggtcagaat gcaccaaact gtgcggaggt   2340
ggaattcagg aacgttacat gactgtaaag aagagattca aaagctccca gtttaccagc   2400
tgcaaagaca agaaggagat cagagcatgc aatgttcatc cttgttagca agggtacgag   2460
```

-continued

```
ttccccaggg ctgcactcta gattccagag tcaccaatgg ctggattatt tgcttgttta   2520

agacaattta aattgtgtac gctagttttc atttttgcag tgtggttcgc ccagtagtct   2580

tgtggatgcc agagacatcc tttctgaata cttcttgatg ggtacaggct gagtggggcg   2640

ccctcacctc cagccagcct cttcctgcag aggagtagtg tcagccacct tgtactaagc   2700

tgaaacatgt ccctctggag cttccacctg gccagggagg acggagactt tgacctactc   2760

cacatggaga ggcaaccatg tctggaagtg actatgcctg agtcccaggg tgcggcaggt   2820

aggaaacatt cacagatgaa gacagcagat tccccacatt ctcatctttg gcctgttcaa   2880

tgaaaccatt gtttgcccat ctcttcttag tggaacttta ggtctctttt caagtctcct   2940

cagtcatcaa tagttcctgg ggaaaaacag agctggtaga cttgaagagg agcattgatg   3000

ttgggtggct tttgttcttt cactgagaaa ttcggaatac atttgtctca cccctgatat   3060

tggttcctga tgccccagc                                                3079
```

<210> SEQ ID NO 185
<211> LENGTH: 3000
<212> TYPE: DNA
<213> ORGANISM: Homo sapiens

<400> SEQUENCE: 185

```
gtttcagggg aggagacaag gtttcttgtt tgccgtatat gctcctgcag agaagaggaa     60

gtgaccgtgg aggccatctg gccctgtgtt ttgatatggc aaaattaatg aatgcaatca    120

gaagaccttt gagcaagaaa gtaccctgga acaacccaat ttggactgca agtattagtt    180

gggtcttcca ggtgcctctc acagcagcag tcatggcagc agtgactcta gccatgtcca    240

tgaccaactg ctgcataaca aatagccccg agactcagca gcttacaaca gggtccccag    300

cccacagact ggcactggtc catggcttgt taggaacctg actgcgcagc agaaggtgag    360

tgagcattac tgcctgagct ctgcctcctg tcagatcatc aggggcatta gattctcata    420

ggagcgtgaa ccctattgca aaccgcgcat gcgaaggatg tacgttgcgt gctccttatg    480

agaatctaac taatgcctga tgatttgagg tggggcagtt tcatccccaa accatctctc    540

tcccttcatg tccatggaaa aattgtcttc tacaaaacca gtccgtggtg ccaaaaaggt    600

tggagactgc tggtttacaa ccgcaatgaa cattcatcat cccacacagt gtcagagggt    660

cgggaacacg ggtgccctgc ctgtgtgctt ccggttccag atttctcagt gggttgtgat    720

caaggtatca gcggaggccg tattcatctg caagcttgac caggaataga agagccactt    780

catgggtggc tcactcagat gccagcaggt cagtgctggt ggctggcagg cagcctcagc    840

tcctcacctc atggatctct cctgagcaca gttttcctgt ccttacaacc tggtagctgg    900

cttctccaga gcaggtgact caggagagga caaggtgaga gccacagcac cttatggtct    960

agtctcagaa gtcacacgcc atcatttctg caatgtcatt ttggggttcc aggtcagctg   1020

tatcactgtg ggaggtgagt atatagatgt cctagaccat tcaggctgct atgacagaac   1080

accatgaact gagtggctca tgaacaacag aaatttccca cagttctgta ggctgggaaa   1140

tccaagatca aggtggcagc aggttcagcg tctgctaagc tcctgctttt catggattgc   1200

atcttctcac tgtgtcctca cgtgatggac agagcaaatg agctctcagg cactagtccc   1260

agccatgagg actctgcttt catgactcat cactccgcaa aggcccacct ccatcagaag   1320

acagctgcta actgcagctg ccatcctcca agacgggaga cacagaattg ggggacatat   1380

acattgagat ctgaaaggcc tggacagcaa caggtgggga tcgtgggggc atcttggagg   1440

gtggctgccg cagtaacatt tctgacccat gctttctgct tgcactcatc tcctgccttt   1500
```

-continued

```
gatcttcatt atctcaggca gtccccacaa cgactgtatc taggagttca ttttaccctc   1560

attttacaga tgaaacgtct cagagggtaa tgtgcttgcc cagtgtctca caaatgcaaa   1620

gtcactgagg taggatttca acctaggtcc aatcatctct gcagcattag gggttcacca   1680

ttgccataga cttaactgtg tcccccaaaa tttgtatgtt gaagccctac cagcctcccc   1740

cccccaatgt gctgatgttt ggagaaaggg cctttgggag gtaattaggt ttagatgaga   1800

tcatgagggt gggactctca taatggcatt aatgccatca ggtgaagaga taccagagac   1860

cttgtgtcct ctctctctgc aatgtgagga cacagtgaga aggcagctgt ctgcaagctg   1920

ggaagagagt actgaccagg aacttaatca gagggcatct tgatcttgga cttcccagcc   1980

tccagaactc tgaaaagtta atgtctatta tttaagccac gcagtctatg gaattttgtt   2040

agagccaacc caagcttact aagataatca gtatgctgca ctttctataa atgtaatttt   2100

tacatttata aaaacaaaac aagagatttg ctgctctata acaactgtac ctacattgta   2160

gatggaataa caaatctaca tacagattta gtaatctcta tgtagatata gaacatagtg   2220

tatctaatag agacatagtg tctgtggtct gatgttaatt ttaggaatta gccgtcactg   2280

attgggcctt gtccaggtat tcttctccct tgtcctggct ctgtaaccta gttatccttg   2340

tctttgctaa cccataacca actattgtat caggactatt atgccactac agatgatgca   2400

gtttgggttt actgtttctc accatttaga caatacttca tcaaatatat ttctgtatga   2460

ctttagtgat atcagttttt gattcattcc tgcatagatc tgggcaaatt gtagacctta   2520

ggaggtgtat tcaccatcca gttctctgga actgcttatg acatttttct ctgagctttc   2580

ttgtcccaaa aggagccttc ctaaaatagt ctttaagtgc ctttaaaaag agaaagagaa   2640

attaagagaa aaaaaacccc aaactcattc ctttactctg atgtgacagt cctcccagga   2700

cactgcagtg gcctgagttt tgctgttaat ttcattcact tatgtttggg ctatgtaaat   2760

tctgcctaga gctggaatgt cattatgtaa agaaatattt tttgtttata ttctttaata   2820

gtaccagtaa tgtatatctt attcagcttc gagaatataa ttgggttgtt tataaaaacc   2880

acacatcatc aaactcacat tgtaacgatt atttcacttt tcaaaaaaaa tggcattaga   2940

aaaacttgaa tgatgttagt tatcttaaag aagtgtgtac tatgtttaaa aaaaaaaaaa   3000
```

<210> SEQ ID NO 186
<211> LENGTH: 807
<212> TYPE: PRT
<213> ORGANISM: Homo sapiens

<400> SEQUENCE: 186

```
Met Arg Leu Ser Pro Ala Pro Leu Lys Leu Ser Arg Thr Pro Ala Leu
                  5                  10                  15

Leu Ala Leu Ala Leu Pro Leu Ala Ala Ala Leu Ala Phe Ser Asp Glu
             20                  25                  30

Thr Leu Asp Lys Val Pro Lys Ser Glu Gly Tyr Cys Ser Arg Ile Leu
         35                  40                  45

Arg Ala Gln Gly Thr Arg Arg Glu Gly Tyr Thr Glu Phe Ser Leu Arg
     50                  55                  60

Val Glu Gly Asp Pro Asp Phe Tyr Lys Pro Gly Thr Ser Tyr Arg Val
 65                  70                  75                  80

Thr Leu Ser Ala Ala Pro Pro Ser Tyr Phe Arg Gly Phe Thr Leu Ile
                 85                  90                  95

Ala Leu Arg Glu Asn Arg Glu Gly Asp Lys Glu Glu Asp His Ala Gly
            100                 105                 110
```

-continued

```
Thr Phe Gln Ile Ile Asp Glu Glu Glu Thr Gln Phe Met Ser Asn Cys
        115                 120                 125

Pro Val Ala Val Thr Glu Ser Thr Pro Arg Arg Arg Thr Arg Ile Gln
    130                 135                 140

Val Phe Trp Ile Ala Pro Pro Ala Gly Thr Gly Cys Val Ile Leu Lys
145                 150                 155                 160

Ala Ser Ile Val Gln Lys Arg Ile Ile Tyr Phe Gln Asp Glu Gly Ser
                165                 170                 175

Leu Thr Lys Lys Leu Cys Glu Gln Asp Ser Thr Phe Asp Gly Val Thr
            180                 185                 190

Asp Lys Pro Ile Leu Asp Cys Cys Ala Cys Gly Thr Ala Lys Tyr Arg
        195                 200                 205

Leu Thr Phe Tyr Gly Asn Trp Ser Glu Lys Thr His Pro Lys Asp Tyr
    210                 215                 220

Pro Arg Arg Ala Asn His Trp Ser Ala Ile Ile Gly Gly Ser His Ser
225                 230                 235                 240

Lys Asn Tyr Val Leu Trp Glu Tyr Gly Gly Tyr Ala Ser Glu Gly Val
                245                 250                 255

Lys Gln Val Ala Glu Leu Gly Ser Pro Val Lys Met Glu Glu Glu Ile
            260                 265                 270

Arg Gln Gln Ser Asp Glu Val Leu Thr Val Ile Lys Ala Lys Ala Gln
        275                 280                 285

Trp Pro Ala Trp Gln Pro Leu Asn Val Arg Ala Ala Pro Ser Ala Glu
    290                 295                 300

Phe Ser Val Asp Arg Thr Arg His Leu Met Ser Phe Leu Thr Met Met
305                 310                 315                 320

Gly Pro Ser Pro Asp Trp Asn Val Gly Leu Ser Ala Glu Asp Leu Cys
                325                 330                 335

Thr Lys Glu Cys Gly Trp Val Gln Lys Val Val Gln Asp Leu Ile Pro
            340                 345                 350

Trp Asp Ala Gly Thr Asp Ser Gly Val Thr Tyr Glu Ser Pro Asn Lys
        355                 360                 365

Pro Thr Ile Pro Gln Glu Lys Ile Arg Pro Leu Thr Ser Leu Asp His
    370                 375                 380

Pro Gln Ser Pro Phe Tyr Asp Pro Glu Gly Gly Ser Ile Thr Gln Val
385                 390                 395                 400

Ala Arg Val Val Ile Glu Arg Ile Ala Arg Lys Gly Glu Gln Cys Asn
                405                 410                 415

Ile Val Pro Asp Asn Val Asp Asp Ile Val Ala Asp Leu Ala Pro Glu
            420                 425                 430

Glu Lys Asp Glu Asp Asp Thr Pro Glu Thr Cys Ile Tyr Ser Asn Trp
        435                 440                 445

Ser Pro Trp Ser Ala Cys Ser Ser Ser Thr Cys Asp Lys Gly Lys Arg
    450                 455                 460

Met Arg Gln Arg Met Leu Lys Ala Gln Leu Asp Leu Ser Val Pro Cys
465                 470                 475                 480

Pro Asp Thr Gln Asp Phe Gln Pro Cys Met Gly Pro Gly Cys Ser Asp
                485                 490                 495

Glu Asp Gly Ser Thr Cys Thr Met Ser Glu Trp Ile Thr Trp Ser Pro
            500                 505                 510

Cys Ser Ile Ser Cys Gly Met Gly Met Arg Ser Arg Glu Arg Tyr Val
        515                 520                 525
```

-continued

```
Lys Gln Phe Pro Glu Asp Gly Ser Val Cys Thr Leu Pro Thr Glu Glu
    530                 535                 540

Met Glu Lys Cys Thr Val Asn Glu Glu Cys Ser Pro Ser Ser Cys Leu
545                 550                 555                 560

Met Thr Glu Trp Gly Glu Trp Asp Glu Cys Ser Ala Thr Cys Gly Met
                565                 570                 575

Gly Met Lys Lys Arg His Arg Met Ile Lys Met Asn Pro Ala Asp Gly
            580                 585                 590

Ser Met Cys Lys Ala Glu Thr Ser Gln Ala Glu Lys Cys Met Met Pro
        595                 600                 605

Glu Cys His Thr Ile Pro Cys Leu Leu Ser Pro Trp Ser Glu Trp Ser
    610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Asp Leu Glu Gln
                645                 650                 655

Val Glu Lys Cys Met Leu Pro Glu Cys Pro Ile Asp Cys Glu Leu Thr
            660                 665                 670

Glu Trp Ser Gln Trp Ser Glu Cys Asn Lys Ser Cys Gly Lys Gly His
        675                 680                 685

Val Ile Arg Thr Arg Met Ile Gln Met Glu Pro Gln Phe Gly Gly Ala
    690                 695                 700

Pro Cys Pro Glu Thr Val Gln Arg Lys Lys Cys Arg Ile Arg Lys Cys
705                 710                 715                 720

Leu Arg Asn Pro Ser Ile Gln Lys Pro Arg Trp Arg Glu Ala Arg Glu
                725                 730                 735

Ser Arg Arg Ser Glu Gln Leu Lys Glu Glu Ser Glu Gly Glu Gln Phe
            740                 745                 750

Pro Gly Cys Arg Met Arg Pro Trp Thr Ala Trp Ser Glu Cys Thr Lys
        755                 760                 765

Leu Cys Gly Gly Gly Ile Gln Glu Arg Tyr Met Thr Val Lys Lys Arg
    770                 775                 780

Phe Lys Ser Ser Gln Phe Thr Ser Cys Lys Asp Lys Lys Glu Ile Arg
785                 790                 795                 800

Ala Cys Asn Val His Pro Cys
                805
```

<210> SEQ ID NO 187
<211> LENGTH: 892
<212> TYPE: DNA
<213> ORGANISM: Homo sapiens

<400> SEQUENCE: 187

```
tttattgatg tttcaacagg cacttattca aataagttat atatttgaaa acagccatgg     60

taagcatcct tggcttctca cccattcctc atgtggcatg ctttctagac tttaaaatga    120

ggtaccctga atagcactaa gtgctctgta agctcaagga atctgtgcag tgctacaaag    180

cccacaggca gagaaagaac tcctcaagtg cttgtggtca gagactaggt tccatatgag    240

gcacacctat gatgaaggtc ttcacctcca gaaggtgaca ctgttcagag atcctcattt    300

cctggagagt gggagaaaat ccctcctttg ggaaatccct tttcccagca gcagagccca    360

cctcattgct tagtgatcat ttggaaggca ctgagagcct tcaggggctg acagcagaga    420

aatgaaaatg agtacagttc agatggtgga agaagcatgg cagtgacatc ttccatgctc    480

tttttctcag tgtctgcaac tccaaagatc aaggccataa cccaggagac catcaacgga    540
```

-continued agattagttc tttgtcaagt gaatgaaatc caaaagcacg catgagacca atgaaagttt 600
ccgcctgttg taaaatctat tttcccccaa ggaaagtcct tgcacagaca ccagtgagtg 660
agttctaaaa gatacccttg gaattatcag actcagaaac ttttattttt tttttctgta 720
acagtctcac cagacttctc ataatgctct taatatattg cacttttcta atcaaagtgc 780
gagtttatga gggtaaagct ctactttcct actgcagcct tcagattctc atcattttgc 840
atctattttg tagccaataa aactccgcac tagcaaaaaa aaaaaaaaaa aa 892

<210> SEQ ID NO 188
<211> LENGTH: 1448
<212> TYPE: DNA
<213> ORGANISM: Homo sapiens
<220> FEATURE:
<221> NAME/KEY: misc_feature
<222> LOCATION: (1)...(1448)
<223> OTHER INFORMATION: n = A,T,C or G

<400> SEQUENCE: 188
tgtgactcac atttctttta ctgtgacaca ataatgtgat cctaaaactg gcttatcctt 60
gagtgtttac aactcaaaca actttttgaa tgcagtagtt tttttttttt aaaaacaaac 120
ttttatgtca aatttttttt cttagaagta gtcttcatta ttataaattt gtacaccaaa 180
aggccatggg gaactttgtg caagtacctc atcgctgagc aaatggagct tgctatgttt 240
taatttcaga aaatttcctc atatacgtag tgtgtagaat caagtctttt aataattcat 300
tttttcttca taatatttac tcaaagttaa gcttaaaaat aagttttatc ttaaaatcat 360
atttgaagac agtaagacag taaactattt taggaagtca acccccattg cactctgtgg 420
cagttattct ggtaaaaata ggcaaaagtg acctgaatct acaatggtgt cccaaagtaa 480
ccaagtaaga gagattgtaa atgataaacc gagctttaaa ggataaagtg ttaataaaga 540
aaggaagctg ggcacatgtc aaaaagggag atcgaaatgt taggtaatca tttagaaagg 600
acagaaaata tttaaagtgg ctcataggta atgaatattt ctgacttaga tgtaaatcca 660
tctggaatct ttacatcctt tgccagctga aacaagaaag tgaagggaca atgatatttc 720
atggtcagtt tattttgtaa gagacagaag aaattatatc tatacattac cttgtagcag 780
cagtacctgg aagccccagc ccgtcacaga agtgtggagg ggggctcctg actagacaat 840
ttccctagcc cttgtgattt gaagcatgaa agttctggca ggttatgagc agcactaggg 900
ataaagtatg gttttatttt ggtgtaattt aggtttttca acaaagccct tgtctaaaat 960
aaaaggcatt attggaaata tttgaaaact agaaaatgat ggataaaagg gctgataaga 1020
aaatttctga ctgtcagtag aagtgagata agatcctcag aggaaacagt aagaagggat 1080
aatcattaag atagtaaaac aggcaaagca gaatcacatg tgcncacaca catacacatg 1140
taaacattgg aatgcataag ttttaatatt ttagcgctat cagtttctaa atgcattaat 1200
tactaactgc cctctcccaa gattcattta gttcaaacag tatccgtaaa ctaggaataa 1260
tgccacatgc attcaatggg atcttttaag tactcttcag tttgttccaa gaaatgtgcc 1320
tactgaaatc aaattaattt gtattcaatg tgtacttcaa gactgctaat tgtttcatct 1380
gaaagcctac aatgaatcat tgttcamcct tgaaaaataa aattttgtaa atcaaaaaaa 1440
aaaaaaaa 1448

<210> SEQ ID NO 189
<211> LENGTH: 460
<212> TYPE: DNA

-continued

<213> ORGANISM: Homo sapiens

<400> SEQUENCE: 189
ttttgggagc acggactgtc agttctctgg gaagtggtca gcgcatcctg cagggcttct 60
cctcctctgt cttttggaga accagggctc ttctcagggg ctctagggac tgccaggctg 120
tttcagccag gaaggccaaa atcaagagtg agatgtagaa agttgtaaaa tagaaaaagt 180
ggagttggtg aatcggttgt tctttcctca catttggatg attgtcataa ggtttttagc 240
atgttcctcc ttttcttcac cctccccttt tttcttctat taatcaagag aaacttcaaa 300
gttaatggga tggtcggatc tcacaggctg agaactcgtt cacctccaag catttcatga 360
aaaagctgct tcttattaat catacaaact ctcaccatga tgtgaagagt ttcacaaatc 420
cttcaaaata aaaagtaatg acttaaaaaa aaaaaaaaaa 460

<210> SEQ ID NO 190
<211> LENGTH: 481
<212> TYPE: DNA
<213> ORGANISM: Homo sapiens

<400> SEQUENCE: 190
aggtggtgga agaaactgtg gcacgaggtg actgaggtat ctgtgggagc taatcctgtc 60
caggtggaag taggagaatt tgatgatggt gcagaggaaa ccgaagagga ggtggtggcg 120
gaaaatccct gccagaacca ccactgcaaa cacggcaagg tgtgcgagct ggatgagaac 180 aacacccccca tgtgcgtgtg ccaggacccc accagctgcc cagcccccat tggcgagttt 240
gagaaggtgt gcagcaatga caacaagacc ttcgactctt cctgccactt ctttgccaca 300
aagtgcaccc tggagggcac caagaagggc cacaagctcc acctggacta catcgggcct 360
tgcaaataca tcccccccttg cctggactct gagctgaccg aattccccct gcgcatgcgg 420
gactggctca agaacgtcct ggtcaccctg tatgagaggg atgaggacaa caaccttctg 480
a 481

<210> SEQ ID NO 191
<211> LENGTH: 489
<212> TYPE: DNA
<213> ORGANISM: Homo sapiens
<220> FEATURE:
<221> NAME/KEY: misc_feature
<222> LOCATION: (1)...(489)
<223> OTHER INFORMATION: n = A,T,C or G

<400> SEQUENCE: 191
atataaatta gactaagtgt tttcaaataa atctaaatct tcagcatgat gtgttgtgta 60
taattggagt agatattaat taagtcccct gtataatgtt ttgtaatttt gcaaaacata 120
tcttgagttg tttaaacagt caaaatgttt gatattttat accagcttat gagctcaaag 180
tactacagca aagcctagcc tgcatatcat tcacccaaaa caaagtaata gcgcctcttt 240
tattattttg actgaatgtt ttatggaatt gaaagaaaca tacgttcttt tcaagacttc 300
ctcatgaatc tntcaattat aggaaaagtt attgtgataa aataggaaca gctgaaagat 360
tgattaatga actattgtta attcttccta ttttaatgaa tgacattgaa ctgaattttt 420
tgtctgttaa atgaacttga tagctaataa aaagncaact agccatcaaa aaaaaaaaaa 480
aaaaaaaaa 489

<210> SEQ ID NO 192
<211> LENGTH: 516

-continued

<212> TYPE: DNA
<213> ORGANISM: Homo sapiens

<400> SEQUENCE: 192 actttcaaagc cagctgaagg aaagaggaag tgctagagag agccccttc agtgtgcttc 60 tgacttttac ggacttggct tgttagaagg ctgaaagatg atggcaggaa tgaaaatcca 120
gcttgtatgc atgctactcc tggctttcag ctcctggagt ctgtgctcag attcagaaga 180
ggaaatgaaa gcattagaag cagatttctt gaccaatatg catacatcaa agattagtaa 240
agcacatgtt ccctcttgga agatgactct gctaaatgtt tgcagtcttg taaataattt 300
gaacagccca gctgaggaaa caggagaagt tcatgaagag gagcttgttg caagaaggaa 360
cttcttactg ctttagatgg ctttagcttg gaagcaatgt tgacaatata ccagctccac 420
aaaatctgtc acagcagggc ttttcaacac tgggagttaa tccaggaaga tattcttgat 480
actggaaatg acaaaaatgg aaaggaagaa gtcata 516

<210> SEQ ID NO 193
<211> LENGTH: 1409
<212> TYPE: DNA
<213> ORGANISM: Homo sapiens

<400> SEQUENCE: 193
tgattctttt ccaaaacttt tagccatagg gtcttttata gacagggata gtaaaatgaa 60
aattgagaaa tataagatga aaaggaatgg taaaaatatc ttttaggggg cttttaattg 120
gtgatctgaa atcttgggag aagctgttct tttcaggcct gaggtgctct tgactgtcgc 180
ctgcgcactg tgtaccccga gcaacattct aagggtgtgc tttcgccttg gctaactcct 240
ttgacctcat tcttcatata gtagtctagg aaaaagttgc aggtaattta aactgtctag 300
tggtacatag taactgaatt tctattccta tgagaaatga gaattattta tttgccatca 360
acacatttta tactttgcat ctccaaattt attgcggcga gacttgtcca ttgtgaaagt 420
tagagaacat tatgtttgta tcatttcttt cataaaacct caagagcatt tttaagccct 480
tttcatcaga cccagtgaaa actaaggata gatgtttttt aactggaggt ctcctgataa 540
ggagaacaca atccaccatt gtcatttaag taataagaca ggaaattgac cttgacgctt 600
tcttgttaaa tagatttaac aggaacatct gcacatcttt tttccttgtg cactatttgt 660
ttaattgcag tggattaata cagcaagagt gccacattat aactaggcaa ttatccattc 720
ttcaagactt agttattgtc acactaattg atcgtttaag gcataagatg gtctagcatt 780
aggaacatgt gaagctaatc tgctcaaaaa gatcaacaaa ttaatattgt tgctgatatt 840
tgcataattg gctgcaatta tttaatgttt aattgggttg atcaaatgag attcagcaat 900
tcacaagtgc attaatataa acagaactgg ggcacttaaa atgataatga ttaacttata 960
ttgcatgttc tcttcctttc acttttttca gtgtctacat ttcagaccga gtttgtcagc 1020
ttttttgaaa acacatcagt agaaaccaag attttaaaat gaagtgtcaa gacgaaggca 1080
aaacctgagc agttcctaaa aagatttgct gttagaaatt ttctttgtgg cagtcattta 1140
ttaaggattc aactcgtgat acaccaaaag aagagttgac ttcagagatg tgttccatgc 1200
tctctagcac aggaatgaat aaatttataa cacctgcttt agcctttgtt ttcaaaagca 1260
caaaggaaaa gtgaaaggga aagagaaaca agtgactgag aagtcttgtt aaggaatcag 1320
gttttttcta cctggtaaac attctctatt cttttctcaa aagattgttg taagaaaaaa 1380
tgtaagmcaa aaaaaaaaaa aaaaaaaaa 1409

-continued

<210> SEQ ID NO 194
<211> LENGTH: 441
<212> TYPE: DNA
<213> ORGANISM: Homo sapiens

<400> SEQUENCE: 194
cagatttcgg tagccatctc cctccaaata tgtctctttc tgctttctta gtgcccatta 60
tttccccttc tcctttcttc tgtcactgcc atctccttct tggtcttccc attgttcttt 120
aactggccgt aatgtggaat tgatatttac attttgatac ggttttttttc ttggcctgtg 180 tacgggattg cctcatttcc tgctctgaat tttaaaatta gatattaaag ctgtcatatg 240
gtttcctcac aaaagtcaac aaagtccaaa caaaaatagt ttgccgtttt actttcatcc 300
attgaaaaag gaaattgtgc ctcttgcagc ctaggcaaag gacatttagt actatcgatt 360
ctttccaccc tcacgatgac ttgcggttct ctctgtagaa aagggatggc ctaagaaata 420
caactaaaaa aaaaaaaaaa a 441

<210> SEQ ID NO 195
<211> LENGTH: 707
<212> TYPE: DNA
<213> ORGANISM: Homo sapiens

<400> SEQUENCE: 195
cagaaaaata tttggaaaaa atataccact tcatagctaa gtcttacaga gaagaggatt 60
tgctaataaa acttaagttt tgaaaattaa gatgcaggta gagcttctga actaatgccc 120
acagctccaa ggaagacatg tcctatttag ttattcaaat acaagttgag ggcattgtga 180
ttaagcaaac aatatatttg ttagaacttt gtttttaaat tactgttcct tgacattact 240
tataaagagt ctctaacttt cgatttctaa aactatgtaa tacaaaagta tagtttcccc 300
atttgataaa aggccaatga tactgagtag gatatatgcg tatcatgcta cttcattcag 360
tgtgtctgtt tttaatacta ataaggcagt ttgacagaaa ttatttcttt gggactaagg 420
tgattatcat ttttttcccc ttcaaaattg tgctttaagt gctgataacc acaggcagat 480
tgcaaagaac tgataaggca acaaaagtag agaattttag gatcaaaggc atgtaactga 540
aaggtaacaa cagtacataa gcgacaactg gggaaggcag cagtgaaaca tgtttgtggg 600
gttaagtgag tcattgtaaa taaggaattt gcacatttat tttctgtcga cgcggccgcc 660
actgtgctgg atatctgcag aattccacca cactggacta gtggatc 707

<210> SEQ ID NO 196
<211> LENGTH: 552
<212> TYPE: DNA
<213> ORGANISM: Homo sapiens
<220> FEATURE:
<221> NAME/KEY: misc_feature
<222> LOCATION: (1)...(552)
<223> OTHER INFORMATION: n = A,T,C or G

<400> SEQUENCE: 196
tggccagcca gcctgatgtg gatggcttcc ttggggtggt gcttccctca agcccgaatt 60
ngtggacatc atcaatgcca aacaatgagc cccatccatt ttccctaccc ttcctgccaa 120
gccagggant aagcagccca gaagcccagt aactgccctt tccctgcata tgcttttgat 180
ggtgtcatnt gctccttcct gtggcctcat ccaaactgta tnttccttta ctgtttatat 240
nttcaccctg taatggttgg gaccaggcca atcccttntc cacttactat aatggttgga 300
actaaacgtc accaaggtgg cttntccttg gctgagaant ggaaggcgtg gtgggatttg 360

-continued

```
ctnctgggtt ccctaggccc tagtgagggc agaagagaaa ccatcctntc ccttnttaca    420

ccgtgaggcc aagatcccct cagaaggcag gagtgctgcc ctntcccatg gtgcccgtgc    480

ctntgtgctg tgtatgtgaa ccacccatgt gagggaataa acctggcact aggaaaaaaa    540

aaaaaaaaaa aa                                                        552


<210> SEQ ID NO 197
<211> LENGTH: 449
<212> TYPE: DNA
<213> ORGANISM: Homo sapiens
<220> FEATURE:
<221> NAME/KEY: misc_feature
<222> LOCATION: (1)...(449)
<223> OTHER INFORMATION: n = A,T,C or G

<400> SEQUENCE: 197

ctccagagac aacttcgcgg tgtggtgaac tctctgagga aaaacacgtg cgtggnanca     60

agtgactgag acctanaaat ccaagcgttg gaggtcctga ggccagccta agtcgcttca    120

aaatggaacg aaggcgtttg cggggttcca ttcagagccg atacatcagc atgagtgtgt    180

ggacaagccc acggagactt gtggagctgg cagggcagag cctgctgaag gatgaggccc    240

tggccattgc ccgccctgga gttgctgccc agggagctct tcccgccact cttcatggca    300

gcctttgacg ggagacacag ccagaccctg aaggcaatgg tgcaggcctg gcccttcacc    360

tgcctccctc tgggagtgct gatgaaggga caacatcttc acctggagac cttcaaagct    420

gtgcttgatg gacttgatgt gctccttgc                                      449


<210> SEQ ID NO 198
<211> LENGTH: 606
<212> TYPE: DNA
<213> ORGANISM: Homo sapiens

<400> SEQUENCE: 198

tgagtttgcc cccttacccc catcccagtg aatatttgca attcctaaag acgtgttttg     60

attgtcacac ctgggtgggg aacatgctac tggcatctaa tgcatagagg gcagtaatgc    120

tgctaaacat ctttcaacgc acaggacaga gccccacaaa agagaattat ctagccccaa    180

atgtccataa cactgctgtt gagaaaacct accgcaggat cttactgggc ttcataggta    240

agcttgcctt tgttctggct tctgtagata tataaaataa agacactgcc cagtccctcc    300

ctcaacgtcc cgagccaggg ctcaaggcaa ttccaataac agtagaatga acactaaata    360

ttgatttcaa aatctcagca actagaagaa tgaccaacca tcctggttgg cctgggactg    420

tcctagtttt agcattgaaa gtttcaggtt ccaggaaagc cctcaggcct gggctgctgg    480

tcaccctagc agctgaggga ctcttcaata cagaattagt ctttgtgcac tggagatgaa    540

tatactttaa tttgtaacat gtgaaaacat ctataaacat ctactgaagc ctgttcttgt    600

ctgcac                                                               606


<210> SEQ ID NO 199
<211> LENGTH: 369
<212> TYPE: DNA
<213> ORGANISM: Homo sapiens
<220> FEATURE:
<221> NAME/KEY: misc_feature
<222> LOCATION: (1)...(369)
<223> OTHER INFORMATION: n = A,T,C or G

<400> SEQUENCE: 199
```

-continued

```
ggcaactttt tgcggattgt tcttgcttnc aggctttgcg ctgcaaatcc agtgctacca     60

gtgtgaagaa ttccagctga acaacgactg ctcctccccc gagttcattg tgaattgcac    120

ggtgaacgtt caagacatgt gtcagaaaga agtgatggag caaagtgccg ggatcatgta    180

ccgcaagtcc tgtgcatcat cagcggcctg tctcatcgcc tctgccgggt accagtcctt    240

ctgctcccca gggaaactga actcagtttg catcagctgc tgcaacaccc ctctttgtaa    300

cgggccaagg cccaagaaaa ggggaagttc tgcctcggcc ctcangccat ggctccgcac    360

caccatcct                                                            369
```

```
<210> SEQ ID NO 200
<211> LENGTH: 55
<212> TYPE: PRT
<213> ORGANISM: Homo sapiens

<400> SEQUENCE: 200

Met Tyr Arg Asn Trp Ser Gly Cys Phe Gly Leu Gln Val Thr Leu Cys
                  5                  10                  15

His Thr Phe Glu Thr Arg Asp Leu Ser Arg Leu Ser Ser Asp Ser Gln
             20                  25                  30

Pro Thr Ser Asn Val Ser Gln Ser Ile Ser His Lys Val Leu Ser Phe
         35                  40                  45

Ser Gly Val Ile Val Thr Pro
     50                  55


<210> SEQ ID NO 201
<211> LENGTH: 67
<212> TYPE: PRT
<213> ORGANISM: Homo sapiens

<400> SEQUENCE: 201

Met Gln Leu Leu Ser Pro Asn Thr Lys Phe Thr Ser Cys Leu Ser Arg
                  5                  10                  15

Gln Arg Gly Asn Leu Val Phe Leu Gly Asp Leu Lys Gly Cys Ser Glu
             20                  25                  30

Leu Lys Asn Phe Gln Glu Leu Ile Asn Gln Ser Ala Leu Val His Pro
         35                  40                  45

Arg Val Asp Val Trp Trp Tyr Cys Gly Gly Pro Leu Leu Gly Thr Leu
     50                  55                  60

Pro Asn Asn
 65


<210> SEQ ID NO 202
<211> LENGTH: 73
<212> TYPE: PRT
<213> ORGANISM: Homo sapiens

<400> SEQUENCE: 202

Met Thr Pro Glu Lys Leu Arg Thr Leu Cys Glu Ile Asp Trp Leu Thr
                  5                  10                  15

Leu Glu Val Gly Trp Leu Ser Glu Glu Ser Leu Glu Arg Ser Leu Val
             20                  25                  30

Ser Lys Val Trp His Lys Val Thr Cys Lys Pro Lys His Pro Asp Gln
         35                  40                  45

Phe Leu Tyr Ile Asp Ser Tyr Ser Trp Phe Arg Pro Leu Pro Pro Leu
     50                  55                  60

Pro Thr Val Val Lys Arg Thr Ala Ala
 65                  70
```

-continued

<210> SEQ ID NO 203
<211> LENGTH: 2008
<212> TYPE: DNA
<213> ORGANISM: Homo sapiens

<400> SEQUENCE: 203

```
ctccagagac aacttcgcgg tgtggtgaac tctctgagga aaaacacgtg cgtggtaaca     60

agtgactgag acctagaaat ccaagcgttg gaggtcctga ggccagccta agtcgcttca    120

aaatggaacg aaggcgtttg cggggttcca ttcagagccg atacatcagc atgagtgtgt    180

ggacaagccc acggagactt gtggagctgg cagggcagag cctgctgaag gatgaggccc    240

tggccattgc ccgccctgga gttgctgccc agggagctct tcccgccact cttcatggca    300

gcctttgacg ggagacacag ccagaccctg aaggcaatgg tgcaggcctg gcccttcacc    360

tgcctccctc tgggagtgct gatgaaggga caacatcttc acctggagac cttcaaagct    420

gtgcttgatg gacttgatgt gctccttgcc caggaggttc gccccaggag gtggaaactt    480

caagtgctgg atttacggaa gaactctcat caggacttct ggactgtatg gtctggaaac    540

agggccagtc tgtactcatt tccagagcca gaagcagctc agcccatgac aaagaagcga    600

aaagtagatg gtttgagcac agaggcagag cagcccttca ttccagtaga ggtgctcgta    660

gacctgttcc tcaaggaagg tgcctgtgat gaattgttct cctacctcat tgagaaagtg    720

aagcgaaaga aaaatgtact acgcctgtgc tgtaagaagc tgaagatttt tgcaatgccc    780

atgcaggata tcaagatgat cctgaaaatg gtgcagctgg actctattga agatttggaa    840

gtgacttgta cctggaagct acccaccttg gcgaaatttt ctccttacct gggccagatg    900

attaatctgc gtagactcct cctctcccac atccatgcat cttcctacat ttccccggag    960

aaggaagagc agtatatcgc ccagttcacc tctcagttcc tcagtctgca gtgcctgcag   1020

gctctctatg tggactcttt atttttcctt agaggccgcc tggatcagtt gctcaggcac   1080

gtgatgaacc ccttggaaac cctctcaata actaactgcc ggctttcgga aggggatgtg   1140

atgcatctgt cccagagtcc cagcgtcagt cagctaagtg tcctgagtct aagtggggtc   1200

atgctgaccg atgtaagtcc cgagcccctc caagctctgc tggagagagc ctctgccacc   1260

ctccaggacc tggtctttga tgagtgtggg atcacggatg atcagctcct tgccctcctg   1320

ccttccctga gccactgctc ccagcttaca accttaagct tctacgggaa ttccatctcc   1380

atatctgcct tgcagagtct cctgcagcac ctcatcgggc tgagcaatct gacccacgtg   1440

ctgtatcctg tcccccctgga gagttatgag gacatccatg gtaccctcca cctggagagg   1500

cttgcctatc tgcatgccag gctcagggag ttgctgtgtg agttggggcg gcccagcatg   1560

gtctggctta gtgccaaccc ctgtcctcac tgtggggaca gaaccttcta tgacccggag   1620

cccatcctgt gcccctgttt catgcctaac tagctgggtg cacatatcaa atgcttcatt   1680

ctgcatactt ggacactaaa gccaggatgt gcatgcatct tgaagcaaca aagcagccac   1740

agtttcagac aaatgttcag tgtgagtgag gaaaacatgt tcagtgagga aaaaacattc   1800

agacaaatgt tcagtgagga aaaaaagggg aagttgggga taggcagatg ttgacttgag   1860

gagttaatgt gatctttggg gagatacatc ttatagagtt agaaatagaa tctgaatttc   1920

taaagggaga ttctggcttg ggaagtacat gtaggagtta atccctgtgt agactgttgt   1980

aaagaaactg ttgaaaaaaa aaaaaaaa                                      2008
```

<210> SEQ ID NO 204

-continued

<211> LENGTH: 923
<212> TYPE: DNA
<213> ORGANISM: Homo sapiens

<400> SEQUENCE: 204
tgagtttgcc cccttacccc catcccagtg aatatttgca attcctaaag acgtgttttg 60
attgtcacac ctgggtgggg aacatgctac tggcatctaa tgcatagagg gcagtaatgc 120
tgctaaacat ctttcaacgc acaggacaga gccccacaaa agagaattat ctagccccaa 180
atgtccataa cactgctgtt gagaaaacct accgcaggat cttactgggc ttcataggta 240
agcttgcctt tgttctggct tctgtagata tataaaataa agacactgcc cagtccctcc 300
ctcaacgtcc cgagccaggg ctcaaggcaa ttccaataac agtagaatga acactaaata 360
ttgatttcaa aatctcagca actagaagaa tgaccaacca tcctggttgg cctgggactg 420
tcctagtttt agcattgaaa gtttcaggtt ccaggaaagc cctcaggcct gggctgctgg 480
tcaccctagc agctgaggga ctcttcaata cagaattagt ctttgtgcac tggagatgaa 540
tatactttaa tttgtaacat gtgaaaacat ctataaacat ctactgaagc ctgttctgtc 600
tgcaccgaca ttttcattga gtacggattc ttcctaccag atacagctgc tctacaactt 660
tcgagggctg gtataaaact agcttttacc tatttttaaa aattacatga atagtaaaaa 720
cttggattaa cccagtattc gggtattttc aatttccttg ggagcttaga ggacggacaa 780
ataaaaagat tatttcaaca tcaaatatat gctattgttt acatatgaag ataaccacat 840
atatgtataa attcaccgtt actttttagc aatactataa aatccaacag aaaaaaatag 900
catttactaa aaaaaaaaaa aaa 923

<210> SEQ ID NO 205
<211> LENGTH: 1619
<212> TYPE: DNA
<213> ORGANISM: Homo sapiens

<400> SEQUENCE: 205
ggcaactttt tgcggattgt tcttgcttcc aggctttgcg ctgcaaatcc agtgctacca 60
gtgtgaagaa ttccagctga acaacgactg ctcctccccc gagttcattg tgaattgcac 120
ggtgaacgtt caagacatgt gtcagaaaga agtgatggag caaagtgccg ggatcatgta 180
ccgcaagtcc tgtgcatcat cagcggcctg tctcatcgcc tctgccgggt accagtcctt 240
ctgctcccca gggaaactga actcagtttg catcagctgc tgcaacaccc ctctttgtaa 300
cgggccaagg cccaagaaaa ggggaagttc tgcctcggcc ctcaggccag ggctccgcac 360
caccatcctg ttcctcaaat tagccctctt ctcggcacac tgctgaagct gaaggagatg 420
ccaccccctc ctgcattgtt cttccagccc tcgcccccaa ccccccacct ccctgagtga 480
gtttcttctg ggtgtccttt tattctgggt agggagcggg agtccgtgtt ctcttttgtt 540
cctgtgcaaa taatgaaaga gctcggtaaa gcattctgaa taaattcagc ctgactgaat 600
tttcagtatg tacttgaagg aaggaggtgg agtgaaagtt cacccccatg tctgtgtaac 660
cggagtcaag gccaggctgg cagagtcagt ccttagaagt cactgaggtg ggcatctgcc 720
ttttgtaaag cctccagtgt ccattccatc cctgatgggg gcatagtttg agactgcaga 780
gtgagagtga cgttttctta gggctggagg gccagttccc actcaaggct ccctcgcttg 840
acattcaaac ttcatgctcc tgaaaaccat tctctgcagc agaattggct ggtttcgcgc 900
ctgagttggg ctctagtgac tcgagactca atgactggga cttagactgg ggctcggcct 960
cgctctgaaa agtgcttaag aaaatcttct cagttctcct tgcagaggac tggcgccggg 1020

-continued

```
acgcgaagag caacgggcgc tgcacaaagc gggcgctgtc ggtggtggag tgcgcatgta   1080

cgcgcaggcg cttctcgtgg ttggcgtgct gcagcgacag gcggcagcac agcaccttgc   1140

acgaacaccc gccgaaactg ctgcgaggac accgtgtaca ggagcgggtt gatgaccgag   1200

ctgaggtaga aaaacgtctc cgagaagggg aggaggatca tgtacgcccg gaagtaggac   1260

ctcgtccagt cgtgcttggg tttggccgca gccatgatcc tccgaatctg gttgggcatc   1320

cagcatacgg ccaatgtcac aacaatcagc cctgggcaga cacgagcagg agggagagac   1380

agagaaaaga aaaacacagc atgagaacac agtaaatgaa taaaaccata aaatatttag   1440

cccctctgtt ctgtgcttac tggccaggaa atggtaccaa tttttcagtg ttggacttga   1500

cagcttcttt tgccacaagc aagagagaat ttaacactgt ttcaaacccg ggggagttgg   1560

ctgtgttaaa gaaagaccat taaatgcttt agacagtgta aaaaaaaaaa aaaaaaaaa    1619
```

```
<210> SEQ ID NO 206
<211> LENGTH: 2364
<212> TYPE: DNA
<213> ORGANISM: Homo sapiens

<400> SEQUENCE: 206

atgcagcatc accaccatca ccacttctcc gacgagaccc tggacaaagt gcccaagtca     60

gagggctact gtagccgtat cctgcgcgcc cagggcacgc ggcgcgaggg ctacaccgag    120

ttcagcctcc gcgtggaggg cgaccccgac ttctacaagc cgggaaccag ctaccgcgta    180

acactttcag ctgctcctcc ctcctacttc agaggattca cattaattgc cctcagagag    240

aacagagagg gtgataagga agaagaccat gctgggacct tccagatcat agacgaagaa    300

gaaactcagt ttatgagcaa ttgccctgtt gcagtcactg aaagcactcc acggaggagg    360

acccggatcc aggtgttttg gatagcacca ccagcgggaa caggctgcgt gattctgaag    420

gccagcatcg tacaaaaacg cattatttat tttcaagatg agggctctct gaccaagaaa    480

ctttgtgaac aagattccac atttgatggg gtgactgaca aacccatctt agactgctgt    540

gcctgcggaa ctgccaagta cagactcaca ttttatggga attggtccga gaagacacac    600

ccaaaggatt accctcgtcg ggccaaccac tggtctgcga tcatcggagg atcccactcc    660

aagaattatg tactgtggga atatggagga tatgccagcg aaggcgtcaa acaagttgca    720

gaattgggct cacccgtgaa aatggaggaa gaaattcgac aacagagtga tgaggtcctc    780

accgtcatca aagccaaagc ccagtggcca gcctggcagc ctctcaacgt gagagcagca    840

ccttcagctg aattttccgt ggacagaacg cgccatttaa tgtccttcct gaccatgatg    900

ggccctagtc ccgactggaa cgtaggctta tctgcagaag atctgtgcac caaggaatgt    960

ggctgggtcc agaaggtggt gcaagacctg attccctggg acgctggcac cgacagcggg   1020

gtgacctatg agtcacccaa caaacccacc attccccagg agaaaatccg gcccctgacc   1080

agcctggacc atcctcagag tcctttctat gacccagagg gtgggtccat cactcaagta   1140

gccagagttg tcatcgagag aatcgcacgg aagggtgaac aatgcaatat tgtacctgac   1200

aatgtcgatg atattgtagc tgacctggct ccagaagaga aagatgaaga tgacacccct   1260

gaaacctgca tctactccaa ctggtcccca tggtccgcct gcagctcctc cacctgtgac   1320

aaaggcaaga ggatgcgaca gcgcatgctg aaagcacagc tggacctcag cgtcccctgc   1380

cctgacaccc aggacttcca gccctgcatg ggccctggct gcagtgacga agacggctcc   1440

acctgcacca tgtccgagtg gatcacctgg tcgccctgca gcatctcctg cggcatgggc   1500
```

-continued

```
atgaggtccc gggagaggta tgtgaagcag ttcccggagg acggctccgt gtgcacgctg   1560

cccactgagg aaacggagaa gtgcacggtc aacgaggagt gctctcccag cagctgcctg   1620

atgaccgagt ggggcgagtg ggacgagtgc agcgccacct gcggcatggg catgaagaag   1680

cggcaccgca tgatcaagat gaaccccgca gatggctcca tgtgcaaagc cgagacatca   1740

caggcagaga agtgcatgat gccagagtgc cacaccatcc catgcttgct gtccccatgg   1800

tccgagtgga gtgactgcag cgtgacctgc gggaagggca tgcgaacccg acagcggatg   1860

ctcaagtctc tggcagaact tggagactgc aatgaggatc tggagcaggt ggagaagtgc   1920

atgctccctg aatgccccat tgactgtgag ctcaccgagt ggtcccagtg gtcggaatgt   1980

aacaagtcat gtgggaaagg ccacgtgatt cgaacccgga tgatccaaat ggagcctcag   2040

tttggaggtg caccctgccc agagactgtg cagcgaaaaa agtgccgcat ccgaaaatgc   2100

cttcgaaatc catccatcca aaagctacgc tggagggagg cccgagagag ccggcggagt   2160

gagcagctga aggaagagtc tgaaggggag cagttcccag gttgtaggat gcgcccatgg   2220

acggcctggt cagaatgcac caaactgtgc ggaggtggaa ttcaggaacg ttacatgact   2280

gtaaagaaga gattcaaaag ctcccagttt accagctgca aagacaagaa ggagatcaga   2340

gcatgcaatg ttcatccttg ttag                                          2364
```

<210> SEQ ID NO 207
<211> LENGTH: 787
<212> TYPE: PRT
<213> ORGANISM: Homo sapiens

<400> SEQUENCE: 207

```
Met Gln His His His His His His Phe Ser Asp Glu Thr Leu Asp Lys
                5                   10                  15

Val Pro Lys Ser Glu Gly Tyr Cys Ser Arg Ile Leu Arg Ala Gln Gly
            20                  25                  30

Thr Arg Arg Glu Gly Tyr Thr Glu Phe Ser Leu Arg Val Glu Gly Asp
        35                  40                  45

Pro Asp Phe Tyr Lys Pro Gly Thr Ser Tyr Arg Val Thr Leu Ser Ala
    50                  55                  60

Ala Pro Pro Ser Tyr Phe Arg Gly Phe Thr Leu Ile Ala Leu Arg Glu
65                  70                  75                  80

Asn Arg Glu Gly Asp Lys Glu Glu Asp His Ala Gly Thr Phe Gln Ile
                85                  90                  95

Ile Asp Glu Glu Glu Thr Gln Phe Met Ser Asn Cys Pro Val Ala Val
            100                 105                 110

Thr Glu Ser Thr Pro Arg Arg Arg Thr Arg Ile Gln Val Phe Trp Ile
        115                 120                 125

Ala Pro Pro Ala Gly Thr Gly Cys Val Ile Leu Lys Ala Ser Ile Val
    130                 135                 140

Gln Lys Arg Ile Ile Tyr Phe Gln Asp Glu Gly Ser Leu Thr Lys Lys
145                 150                 155                 160

Leu Cys Glu Gln Asp Ser Thr Phe Asp Gly Val Thr Asp Lys Pro Ile
                165                 170                 175

Leu Asp Cys Cys Ala Cys Gly Thr Ala Lys Tyr Arg Leu Thr Phe Tyr
            180                 185                 190

Gly Asn Trp Ser Glu Lys Thr His Pro Lys Asp Tyr Pro Arg Arg Ala
        195                 200                 205

Asn His Trp Ser Ala Ile Ile Gly Gly Ser His Ser Lys Asn Tyr Val
    210                 215                 220
```

-continued

```
Leu Trp Glu Tyr Gly Gly Tyr Ala Ser Glu Gly Val Lys Gln Val Ala
225                 230                 235                 240

Glu Leu Gly Ser Pro Val Lys Met Glu Glu Ile Arg Gln Gln Ser
                245                 250                 255

Asp Glu Val Leu Thr Val Ile Lys Ala Lys Ala Gln Trp Pro Ala Trp
            260                 265                 270

Gln Pro Leu Asn Val Arg Ala Ala Pro Ser Ala Glu Phe Ser Val Asp
        275                 280                 285

Arg Thr Arg His Leu Met Ser Phe Leu Thr Met Met Gly Pro Ser Pro
    290                 295                 300

Asp Trp Asn Val Gly Leu Ser Ala Glu Asp Leu Cys Thr Lys Glu Cys
305                 310                 315                 320

Gly Trp Val Gln Lys Val Val Gln Asp Leu Ile Pro Trp Asp Ala Gly
                325                 330                 335

Thr Asp Ser Gly Val Thr Tyr Glu Ser Pro Asn Lys Pro Thr Ile Pro
            340                 345                 350

Gln Glu Lys Ile Arg Pro Leu Thr Ser Leu Asp His Pro Gln Ser Pro
        355                 360                 365

Phe Tyr Asp Pro Glu Gly Gly Ser Ile Thr Gln Val Ala Arg Val Val
    370                 375                 380

Ile Glu Arg Ile Ala Arg Lys Gly Glu Gln Cys Asn Ile Val Pro Asp
385                 390                 395                 400

Asn Val Asp Asp Ile Val Ala Asp Leu Ala Pro Glu Glu Lys Asp Glu
                405                 410                 415

Asp Asp Thr Pro Glu Thr Cys Ile Tyr Ser Asn Trp Ser Pro Trp Ser
            420                 425                 430

Ala Cys Ser Ser Ser Thr Cys Asp Lys Gly Lys Arg Met Arg Gln Arg
        435                 440                 445

Met Leu Lys Ala Gln Leu Asp Leu Ser Val Pro Cys Pro Asp Thr Gln
    450                 455                 460

Asp Phe Gln Pro Cys Met Gly Pro Gly Cys Ser Asp Glu Asp Gly Ser
465                 470                 475                 480

Thr Cys Thr Met Ser Glu Trp Ile Thr Trp Ser Pro Cys Ser Ile Ser
                485                 490                 495

Cys Gly Met Gly Met Arg Ser Arg Glu Arg Tyr Val Lys Gln Phe Pro
            500                 505                 510

Glu Asp Gly Ser Val Cys Thr Leu Pro Thr Glu Glu Thr Glu Lys Cys
        515                 520                 525

Thr Val Asn Glu Glu Cys Ser Pro Ser Ser Cys Leu Met Thr Glu Trp
    530                 535                 540

Gly Glu Trp Asp Glu Cys Ser Ala Thr Cys Gly Met Gly Met Lys Lys
545                 550                 555                 560

Arg His Arg Met Ile Lys Met Asn Pro Ala Asp Gly Ser Met Cys Lys
                565                 570                 575

Ala Glu Thr Ser Gln Ala Glu Lys Cys Met Met Pro Glu Cys His Thr
            580                 585                 590

Ile Pro Cys Leu Leu Ser Pro Trp Ser Glu Trp Ser Asp Cys Ser Val
        595                 600                 605

Thr Cys Gly Lys Gly Met Arg Thr Arg Gln Arg Met Leu Lys Ser Leu
    610                 615                 620

Ala Glu Leu Gly Asp Cys Asn Glu Asp Leu Glu Gln Val Glu Lys Cys
625                 630                 635                 640
```

-continued

```
Met Leu Pro Glu Cys Pro Ile Asp Cys Glu Leu Thr Glu Trp Ser Gln
                645                 650                 655

Trp Ser Glu Cys Asn Lys Ser Cys Gly Lys Gly His Val Ile Arg Thr
            660                 665                 670

Arg Met Ile Gln Met Glu Pro Gln Phe Gly Gly Ala Pro Cys Pro Glu
        675                 680                 685

Thr Val Gln Arg Lys Lys Cys Arg Ile Arg Lys Cys Leu Arg Asn Pro
    690                 695                 700

Ser Ile Gln Lys Leu Arg Trp Arg Glu Ala Arg Glu Ser Arg Arg Ser
705                 710                 715                 720

Glu Gln Leu Lys Glu Glu Ser Glu Gly Glu Gln Phe Pro Gly Cys Arg
                725                 730                 735

Met Arg Pro Trp Thr Ala Trp Ser Glu Cys Thr Lys Leu Cys Gly Gly
            740                 745                 750

Gly Ile Gln Glu Arg Tyr Met Thr Val Lys Lys Arg Phe Lys Ser Ser
        755                 760                 765

Gln Phe Thr Ser Cys Lys Asp Lys Lys Glu Ile Arg Ala Cys Asn Val
    770                 775                 780

His Pro Cys
785


<210> SEQ ID NO 208
<211> LENGTH: 1362
<212> TYPE: DNA
<213> ORGANISM: Homo sapiens

<400> SEQUENCE: 208

atggcttcac ccagcctccc gggcagtgac tgctcccaaa tcattgatca cagtcatgtc      60

cccgagtttg aggtggccac ctggatcaaa atcaccctta ttctggtgta cctgatcatc     120

ttcgtgatgg gccttctggg gaacagcgcc accattcggg tcacccaggt gctgcagaag     180

aaaggatact tgcagaagga ggtgacagac cacatggtga gtttggcttg ctcggacatc     240

ttggtgttcc tcatcggcat gcccatggag ttctacagca tcatctggaa tcccctgacc     300

acgtccagct acaccctgtc ctgcaagctg cacactttcc tcttcgaggc ctgcagctac     360

gctacgctgc tgcacgtgct gacactcagc tttgagcgct acatcgccat ctgtcacccc     420

ttcaggtaca aggctgtgtc gggaccttgc caggtgaagc tgctgattgg cttcgtctgg     480

gtcacctccg ccctggtggc actgcccttg ctgtttgcca tgggtactga gtacccccctg    540

gtgaacgtgc ccagccaccg gggtctcact tgcaaccgct ccagcacccg ccaccacgag     600

cagcccgaga cctccaatat gtccatctgt accaacctct ccagccgctg gaccgtgttc     660

cagtccagca tcttcggcgc cttcgtggtc tacctcgtgg tcctgctctc cgtagccttc     720

atgtgctgga acatgatgca ggtgctcatg aaaagccaga agggctcgct ggccgggggc     780

acgcggcctc cgcagctgag gaagtccgag agcgaagaga gcaggaccgc caggaggcag     840

accatcatct tcctgaggct gattgttgtg acattggccg tatgctggat gcccaaccag     900

attcggagga tcatggctgc ggccaaaccc aagcacgact ggacgaggtc ctacttccgg     960

gcgtacatga tcctcctccc cttctcggag acgtttttct acctcagctc ggtcatcaac    1020

ccgctcctgt acacggtgtc ctcgcagcag tttcggcggg tgttcgtgca ggtgctgtgc    1080

tgccgcctgt cgctgcagca cgccaaccac gagaagcgcc tgcgcgtaca tgcgcactcc    1140

accaccgaca gcgcccgctt tgtgcagcgc ccgttgctct tcgcgtcccg gcgccagtcc    1200

tctgcaagga gaactgagaa gattttctta agcacttttc agagcgaggc cgagccccag    1260
```

-continued

```
tctaagtccc agtcattgag tctcgagtca ctagagccca actcaggcgc gaaaccagcc   1320

aattctgctg cagagaatgg ttttcaggag catgaagttt ga                      1362


<210> SEQ ID NO 209
<211> LENGTH: 453
<212> TYPE: PRT
<213> ORGANISM: Homo sapiens

<400> SEQUENCE: 209

Met Ala Ser Pro Ser Leu Pro Gly Ser Asp Cys Ser Gln Ile Ile Asp
                5                   10                  15

His Ser His Val Pro Glu Phe Glu Val Ala Thr Trp Ile Lys Ile Thr
            20                  25                  30

Leu Ile Leu Val Tyr Leu Ile Ile Phe Val Met Gly Leu Leu Gly Asn
        35                  40                  45

Ser Ala Thr Ile Arg Val Thr Gln Val Leu Gln Lys Lys Gly Tyr Leu
    50                  55                  60

Gln Lys Glu Val Thr Asp His Met Val Ser Leu Ala Cys Ser Asp Ile
65                  70                  75                  80

Leu Val Phe Leu Ile Gly Met Pro Met Glu Phe Tyr Ser Ile Ile Trp
                85                  90                  95

Asn Pro Leu Thr Thr Ser Ser Tyr Thr Leu Ser Cys Lys Leu His Thr
            100                 105                 110

Phe Leu Phe Glu Ala Cys Ser Tyr Ala Thr Leu Leu His Val Leu Thr
        115                 120                 125

Leu Ser Phe Glu Arg Tyr Ile Ala Ile Cys His Pro Phe Arg Tyr Lys
    130                 135                 140

Ala Val Ser Gly Pro Cys Gln Val Lys Leu Leu Ile Gly Phe Val Trp
145                 150                 155                 160

Val Thr Ser Ala Leu Val Ala Leu Pro Leu Leu Phe Ala Met Gly Thr
                165                 170                 175

Glu Tyr Pro Leu Val Asn Val Pro Ser His Arg Gly Leu Thr Cys Asn
            180                 185                 190

Arg Ser Ser Thr Arg His His Glu Gln Pro Glu Thr Ser Asn Met Ser
        195                 200                 205

Ile Cys Thr Asn Leu Ser Ser Arg Trp Thr Val Phe Gln Ser Ser Ile
    210                 215                 220

Phe Gly Ala Phe Val Val Tyr Leu Val Val Leu Leu Ser Val Ala Phe
225                 230                 235                 240

Met Cys Trp Asn Met Met Gln Val Leu Met Lys Ser Gln Lys Gly Ser
                245                 250                 255

Leu Ala Gly Gly Thr Arg Pro Pro Gln Leu Arg Lys Ser Glu Ser Glu
            260                 265                 270

Glu Ser Arg Thr Ala Arg Arg Gln Thr Ile Ile Phe Leu Arg Leu Ile
        275                 280                 285

Val Val Thr Leu Ala Val Cys Trp Met Pro Asn Gln Ile Arg Arg Ile
    290                 295                 300

Met Ala Ala Ala Lys Pro Lys His Asp Trp Thr Arg Ser Tyr Phe Arg
305                 310                 315                 320

Ala Tyr Met Ile Leu Leu Pro Phe Ser Glu Thr Phe Phe Tyr Leu Ser
                325                 330                 335

Ser Val Ile Asn Pro Leu Leu Tyr Thr Val Ser Ser Gln Gln Phe Arg
            340                 345                 350
```

-continued

```
Arg Val Phe Val Gln Val Leu Cys Cys Arg Leu Ser Leu Gln His Ala
        355                 360                 365

Asn His Glu Lys Arg Leu Arg Val His Ala His Ser Thr Thr Asp Ser
    370                 375                 380

Ala Arg Phe Val Gln Arg Pro Leu Leu Phe Ala Ser Arg Arg Gln Ser
385                 390                 395                 400

Ser Ala Arg Arg Thr Glu Lys Ile Phe Leu Ser Thr Phe Gln Ser Glu
                405                 410                 415

Ala Glu Pro Gln Ser Lys Ser Gln Ser Leu Ser Leu Glu Ser Leu Glu
            420                 425                 430

Pro Asn Ser Gly Ala Lys Pro Ala Asn Ser Ala Ala Glu Asn Gly Phe
        435                 440                 445

Gln Glu His Glu Val
    450


<210> SEQ ID NO 210
<211> LENGTH: 625
<212> TYPE: DNA
<213> ORGANISM: Homo sapiens
<220> FEATURE:
<221> NAME/KEY: misc_feature
<222> LOCATION: (1)...(625)
<223> OTHER INFORMATION: n = A,T,C or G

<400> SEQUENCE: 210

agttctcctt gcagaggact ggcgccggga cgcgaagagc aacgggcgct gcacaaagcg     60

ggcgctgtcg gtggtggagt gcgcatgtac gcgcaggcgc ttctcgtggt tggcgtgctg    120

cagcgacagg cggcagcaca gcacctgcac gaacacccgc cgaaactgct gcgaggacac    180

cgtgtacagg agcgggttga tgaccgagct gaggtagaaa aacgtctccg agaaggggag    240

gaggatcatg tacgcccgga agtaggacct cgtccagtcg tgcttgggtt tggccgcagc    300

catgatcctc cgaatctggt tgggcatcca gcatacggcc aatgtcacaa caatcagccc    360

tgggcagaca cgagcaggag ggagagacag agaaaagaaa aacacagcat gagaacacag    420

taaatgaata aaaccataaa atatttagcc cctctgttct gtgcttactg gccaggaaat    480

ggtaccaatt tttcagtgtt ggacttgaca gcttcttttg ccacaagcaa gagagaattt    540

aacactgttt caaacccggg ggagttggct gtgttaaaga aagaccatta aatgctttag    600

acagtgnaaa aaaaaaaaaa aaaaa                                          625


<210> SEQ ID NO 211
<211> LENGTH: 1619
<212> TYPE: DNA
<213> ORGANISM: Homo sapiens

<400> SEQUENCE: 211

ggcaactttt tgcggattgt tcttgcttcc aggctttgcg ctgcaaatcc agtgctacca     60

gtgtgaagaa ttccagctga acaacgactg ctcctccccc gagttcattg tgaattgcac    120

ggtgaacgtt caagacatgt gtcagaaaga agtgatggag caaagtgccg ggatcatgta    180

ccgcaagtcc tgtgcatcat cagcggcctg tctcatcgcc tctgccgggt accagtcctt    240

ctgctcccca gggaaactga actcagtttg catcagctgc tgcaacaccc ctctttgtaa    300

cgggccaagg cccaagaaaa ggggaagttc tgcctcggcc ctcaggccag ggctccgcac    360

caccatcctg ttcctcaaat tagccctctt ctcggcacac tgctgaagct gaaggagatg    420

ccacccccctc ctgcattgtt cttccagccc tcgcccccaa ccccccacct ccctgagtga    480
```

-continued

```
gtttcttctg ggtgtccttt tattctgggt agggagcggg agtccgtgtt ctcttttgtt    540
cctgtgcaaa taatgaaaga gctcggtaaa gcattctgaa taaattcagc ctgactgaat    600
tttcagtatg tacttgaagg aaggaggtgg agtgaaagtt cacccccatg tctgtgtaac    660
cggagtcaag gccaggctgg cagagtcagt ccttagaagt cactgaggtg ggcatctgcc    720
ttttgtaaag cctccagtgt ccattccatc cctgatgggg gcatagtttg agactgcaga    780
gtgagagtga cgttttctta gggctggagg gccagttccc actcaaggct ccctcgcttg    840
acattcaaac ttcatgctcc tgaaaaccat tctctgcagc agaattggct ggtttcgcgc    900
ctgagttggg ctctagtgac tcgagactca atgactggga cttagactgg ggctcggcct    960
cgctctgaaa agtgcttaag aaaatcttct cagttctcct tgcagaggac tggcgccggg   1020
acgcgaagag caacgggcgc tgcacaaagc gggcgctgtc ggtggtggag tgcgcatgta   1080
cgcgcaggcg cttctcgtgg ttggcgtgct gcagcgacag gcggcagcac agcaccttgc   1140
acgaacaccc gccgaaactg ctgcgaggac accgtgtaca ggagcgggtt gatgaccgag   1200
ctgaggtaga aaaacgtctc cgagaagggg aggaggatca tgtacgcccg gaagtaggac   1260
ctcgtccagt cgtgcttggg tttggccgca gccatgatcc tccgaatctg gttgggcatc   1320
cagcatacgg ccaatgtcac aacaatcagc cctgggcaga cacgagcagg agggagagac   1380
agagaaaaga aaaacacagc atgagaacac agtaaatgaa taaaaccata aaatatttag   1440
cccctctgtt ctgtgcttac tggccaggaa atggtaccaa tttttcagtg ttggacttga   1500
cagcttcttt tgccacaagc aagagagaat ttaacactgt ttcaaacccg ggggagttgg   1560
ctgtgttaaa gaaagaccat taaatgcttt agacagtgta aaaaaaaaaa aaaaaaaaa    1619
```

<210> SEQ ID NO 212
<211> LENGTH: 1010
<212> TYPE: DNA
<213> ORGANISM: Homo sapiens

<400> SEQUENCE: 212

```
ccgcagccgg gagcccgagc gcgggcgatg caggctccgc gagcggcacc tgcggctcct     60
ctaagctacg accgtcgtct ccgctggcag cagctgcggg ccccagcagc ctcggcagcc    120
acagccgctg cagcctgggg cagcctccgc tgctgtcgcc tcctctgatg cgcttgccct    180
ctccctggcc ccgggactcc gggagaatgt gggtcctagg catcgcggca actttttgcg    240
gattgttctt gcttccaagg ctttgcgctg caaatccagt gctaccagtg tgaagaattc    300
cagctgaaca acgactgctc ctcccccgag ttcattgtga attgcacggt gaacgttcaa    360
gacatgtgtc agaaagaagt gatggagcaa agtgccggga tcatgtaccg caagtcctgt    420
gcatcatcag cggcctgtct catcgcctct gccgggtacc agtccttctg ctccccaggg    480
aaactgaact cagtttgcat cagctgctgc aacacccctc tttgtaaccg ggccaaggcc    540
caagaaaagg ggaagttctg cctcggccct caggccaggg ctccgaacca ccatcctgtc    600
cctcaaatta agccctactt ctcggcacac tgctggaagc ttgaagggag aaggcaccca    660
ctcctgcata gtccatccag gcctcgcccc acacaccca ctccctgaga gagcacgccc    720
agggagacca aaaaccggga taggcaacgg acccccagac accacaaggg acccgaggac    780
aaagacgcag acaactcgcg aaagccaccc acgaatacaa cggcccgaac acagatataa    840
cgcacgagcc ccgaccgaca agagaagaag cagaagaaac acccacagac agaaacagac    900
accagcaaca agcgaaaaca gcaaaacgac actagcgaga caccacctgc acacaacacc    960
acagcccaac acagaggaca cgacaacaaa gagacagcac caacgacgaa              1010
```

-continued

<210> SEQ ID NO 213
<211> LENGTH: 480
<212> TYPE: DNA
<213> ORGANISM: Homo sapiens

<400> SEQUENCE: 213
gccaactccg gaggctctgg tgctcggccc gggagcgcga gcgggaggag cagagacccg 60
cagccgggag cccgagcgcg ggcgatgcag gctccgcgag cggcacctgc ggctcctcta 120
agctacgacc gtcgtctccg cggcagcagc gcgggcccca gcagcctcgg cagccacagc 180
cgctgcagcc ggggcagcct ccgctgctgt cgcctcctct gatgcgcttg ccctctcccg 240
gccccgggac tccgggagaa tgtgggtcct aggcatcgcg gcaacttttt gcggattgtt 300
cttgcttcca ggctttgcgc tgcaaatcca gtgctaccag tgtgaagaat tccagctgaa 360
caacgactgc tcctccccg agttcattgt gaattgcacg gtgaacgttc aagacatgtg 420
tgagaaagaa gtgatggagc aaagtgccgg gatcatgtac cgcaagtcct gtgcatgatc 480

<210> SEQ ID NO 214
<211> LENGTH: 1897
<212> TYPE: DNA
<213> ORGANISM: Homo sapiens
<220> FEATURE:
<221> NAME/KEY: misc_feature
<222> LOCATION: (1)...(1897)
<223> OTHER INFORMATION: n = A,T,C or G

<400> SEQUENCE: 214
gccaactccg gaggctctgg tgctcggccc gggagcgcga gcgggaggag cagagacccg 60
cagccgggag cccgagcgcg ggcgatgcag gctccgcgag cggcacctgc ggctcctcta 120
agctacgacc gtcgtctccg cggcagcagc gcgggcccca gcagcctcgg cagccacagc 180
cgctgcagcc ggggcagcct ccgctgctgt cgcctcctct gatgcgcttg ccctctcccg 240
gccccgggac tccgggagaa tgtgggtcct aggcatcgcg gcaacttttt gcggattgtt 300
cttgcttcca ggctttgcgc tgcaaatcca gtgctaccag tgtgaagaat tccagctgaa 360
caacgactgc tcctccccg agttcattgt gaattgcacg gtgaacgttc aagacatgtg 420
tcagaaagaa gtgatggagc aaagtgccgg gatcatgtac cgcaagtcct gtgcatcatc 480
agcggcctgt ctcatcgcct ctgccgggta ccagtccttc tgctccccag ggaaactgaa 540
ctcagtttgc atcagctgct gcaacacccc tctttgtaac gggccaaggc ccaagaaaag 600
gggaagttct gcctcggccc tcaggccagg gctccgcacc accatcctgt tcctcaaatt 660
agccctcttc tcggcacact gctgaagctg aaggagatgc cacccctcc tgcattgttc 720 ttccagccct cgcccccaac cccccacctc cctgagtgag tttcttctgg gtgtcctttt 780
attctgggta gggagcggga gtccgtgttc tcttttgttc ctgtgcaaat aatgaaagag 840
ctcggtaaag cattctgaat aaattcagcy tgactgaatt ttcagtatgt acttgaagga 900
aggaggtgga gtgaaagttc acccccatgt ctgtgtaacc ggagtcaagg ccaggctggc 960
agagtcwgtc cttagaagtc actgaggtgg gcatctgcct tttgtaaagc ctccagtgtc 1020
cattccatcc ctgatggggg catagtttga gactgcagag tgagagtgac gttttcttag 1080
ggctggaggg ccagttccca ctcaaggctc cctcgcttga cattcaaact tcatgctcct 1140
gaaaaccatt ctctgcagca gaattggctg gtttcgcgcc tgagttgggc tctagtgact 1200
cgagactcaa tgactgggac ttagactggg gctcggcctc gctctgaaaa gtgcttaaga 1260

-continued

```
aaatcttctc agttctcctt gcagaggact ggcgccggga cgcgaagagc aacgggcgct   1320

gcacaaagcg ggcgctgtcg gtggtggagt gcgcatgtac gcgcaggcgc ttctcgtggt   1380

tggcgtgctg cagcgacagg cggcagcaca gcacctgcac gaacacccgc cgaaactgct   1440

gcgaggacac cgtgtacagg agcgggttga tgaccgagct gaggtagaaa aacgtctccg   1500

agaaggggag gaggatcatg tacgcccgga agtaggacct cgtccagtcg tgcttgggtt   1560

tggccgcagc catgatcctc cgaatctggt tgggcatcca gcatacggcc aatgtcacaa   1620

caatcagccc tgggcagaca cgagcaggag ggagagacag agaaaagaaa aacacagcat   1680

gagaacacag taaatgaata aaaccataaa atatttagcc cctctgttct gtgcttactg   1740

gccaggaaat ggtaccaatt tttcagtgtt ggacttgaca gcttcttttg ccacaagcaa   1800

gagagaattt aacactgttt caaacccggg ggagttggct gtgttaaaga aagaccatta   1860

aatgctttag acagtgtaaa aaaaaaaaaa aaaaaaa                            1897


<210> SEQ ID NO 215
<211> LENGTH: 141
<212> TYPE: PRT
<213> ORGANISM: Homo sapiens

<400> SEQUENCE: 215

Met Trp Val Leu Gly Ile Ala Ala Thr Phe Cys Gly Leu Phe Leu Leu
                5                   10                  15

Pro Gly Phe Ala Leu Gln Ile Gln Cys Tyr Gln Cys Glu Glu Phe Gln
            20                  25                  30

Leu Asn Asn Asp Cys Ser Ser Pro Glu Phe Ile Val Asn Cys Thr Val
        35                  40                  45

Asn Val Gln Asp Met Cys Gln Lys Glu Val Met Glu Gln Ser Ala Gly
    50                  55                  60

Ile Met Tyr Arg Lys Ser Cys Ala Ser Ser Ala Ala Cys Leu Ile Ala
65                  70                  75                  80

Ser Ala Gly Tyr Gln Ser Phe Cys Ser Pro Gly Lys Leu Asn Ser Val
                85                  90                  95

Cys Ile Ser Cys Cys Asn Thr Pro Leu Cys Asn Gly Pro Arg Pro Lys
            100                 105                 110

Lys Arg Gly Ser Ser Ala Ser Ala Leu Arg Pro Gly Leu Arg Thr Thr
        115                 120                 125

Ile Leu Phe Leu Lys Leu Ala Leu Phe Ser Ala His Cys
    130                 135                 140
```

COMPOSITIONS AND METHODS FOR THE THERAPY AND DIAGNOSIS OF OVARIAN CANCER

CROSS REFERENCE TO RELATED APPLICATIONS

This application is a continuation-in-part of U.S. patent application Ser. No. 09/713,550, filed Nov. 14, 2000, which is a CIP of Ser. No. 09/656,668, filed Sep. 7, 2000, which is a CIP of U.S. application Ser. No. 09/640,173, filed Aug. 15, 2000, which is a is a CIP of U.S. application Ser. No. 09/561,778, filed May 1, 2000, which is a CIP of U.S. application Ser. No. 09/394,374, filed Sep. 10, 1999, now abandoned all pending and incorporated by reference in their entirety herein.

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer, such as ovarian cancer.

In one aspect, the present invention provides polynucleotide compositions comprising a sequence selected from the group consisting of:

(a) sequences provided in SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, and 208;

(b) complements of the sequences provided in SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, and 208;

(c) sequences consisting of at least 20 contiguous residues of a sequence provided in SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, and 208;

(d) sequences that hybridize to a sequence provided in SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, and 208 under moderately stringent conditions;

(e) sequences having at least 75% identity to a sequence provided in SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, 208, and 210–214;

(f) sequences having at least 90% identity to a sequence provided in SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, 208 and 210–214; and (g) degenerate variants of a sequence provided in SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, 208 and 210–214.

In one preferred embodiment, the polynucleotide compositions of the invention are expressed in at least about 20%, more preferably in at least about 30%, and most preferably in at least about 50% of ovarian tumors samples tested, at a level that is at least about 2-fold, preferably at least about 5-fold, and most preferably at least about 10-fold higher than that for normal tissues.

In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the ovarian carcinoma protein comprises a sequence that is encoded by a polynucleotide sequence selected from the group consisting of SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–205, 208 and 210–214, and complements of such polynucleotides.

The present invention further provides polynucleotides that encode a polypeptide as described above or a portion thereof, expression vectors comprising such polynucleotides and host cells transformed or transfected with such expression vectors.

The present invention further provides polypeptide compositions comprising an amino acid sequence selected from the group consisting of sequences recited in SEQ ID NO:200–202, 207, 209 and 215.

In certain preferred embodiments, the polypeptides of the present invention are immunogenic, i.e., they are capable of eliciting an immune response, particularly a humoral and/or cellular immune response, as further described herein.

The present invention further provides fragments, variants and/or derivatives of the disclosed polypeptide sequences, wherein the fragments, variants and/or derivatives preferably have a level of immunogenic activity of at least about 50%, preferably at least about 70% and more preferably at least about 90% of the level of immunogenic activity of a the ovarian carcinoma protein comprises an amino acid sequence encoded by a polynucleotide that comprises a sequence recited in any one of SEQ ID NO:1–185, 187–199, 203–206, 208 and 210–214.

Within other aspects, the present invention provides pharmaceutical compositions comprising a polypeptide and/or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof, and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with ovarian cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with ovarian cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) an ovarian carcinoma polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably an ovarian cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description. All references disclosed herein are hereby incorporated by reference in their entirety as if each was incorporated individually.

BRIEF DESCRIPTION OF THE SEQUENCE IDENTIFIERS

SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, and 193–199 are described in Tables III–VII below.

SEQ ID NO:200 is the amino acid sequence of a polypeptide encoded by the polynucleotide recited in SEQ ID NO:182;

SEQ ID NO:201 is the amino acid sequence of a polypeptide encoded by the polynucleotide recited in SEQ ID NO:182;

SEQ ID NO:202 is the amino acid sequence of a polypeptide encoded by the polynucleotide recited in SEQ ID NO:182.

SEQ ID NO:203 is the determined extended cDNA sequence for SEQ ID NO:197.

SEQ ID NO:204 is the determined extended cDNA sequence for SEQ ID NO:198.

SEQ ID NO:205 is the determined extended cDNA sequence for SEQ ID NO:199.

SEQ ID NO:206 is the determined cDNA sequence for the coding region of O568S fused to an N-terminal His tag.

SEQ ID NO:207 is the amino acid sequence of the polypeptide encoded by the polynucleotide recited in SEQ ID NO:206.

SEQ ID NO:208 is the determined cDNA sequence for the coding region of GPR39 as downloaded from the High Throughput Genomics Database.

SEQ ID NO:209 is the amino acid sequence encoded by the cDNA sequence recited in SEQ ID NO:208.

SEQ ID NO:210 is the nucleotide sequence od O1034C an ovary specific EST clone discovered using electronic subtraction.

SEQ ID NO:211 is the full length nucleotide sequence of O591S.

SEQ ID NO:212 is the sequence BF345141 which shows sequence homology with O1034C/O591S allowing for the extension of O591S.

SEQ ID NO:213 is the sequence BE336607 which shows sequence homology with O1034C/O591S allowing for the extension of O591S.

SEQ ID NO:214 is the consensus nucleotide sequence of O1034C/O591S containing 1897 base pairs.

SEQ ID NO:215 is the predicted translation of the open reading frame identified within SEQ ID NO:214 (nucleotides 260–682).

DETAILED DESCRIPTION OF THE INVENTION

The present invention is directed generally to compositions and their use in the therapy and diagnosis of cancer, particularly ovarian cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" "is used in its conventional meaning, i.e., as a sequence of amino acids.

The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, 208, and 210–214 or a sequence that hybridizes under moderately stringent conditions, or, alternatively, under highly stringent conditions, to a polynucleotide sequence identified above. Certain other illustrative polypeptides of the invention comprise amino acid sequences as set forth in any one of SEQ ID NO:200–202, 207, 209 and 215.

The polypeptides of the present invention are sometimes herein referred to as ovarian tumor proteins or ovarian tumor polypeptides, as an indication that their identification has been based at least in part upon their increased levels of expression in ovarian tumor samples. Thus, a "ovarian tumor polypeptide" or "ovarian tumor protein," refers generally to a polypeptide sequence of the present invention, or a polynucleotide sequence encoding such a polypeptide, that is expressed in a substantial proportion of ovarian tumor samples, for example preferably greater than about 20%, more preferably greater than about 30%, and most preferably greater than about 50% or more of ovarian tumor samples tested, at a level that is at least two fold, and preferably at least five fold, greater than the level of expression in normal tissues, as determined using a representative assay provided herein. An ovarian tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with ovarian cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the fill-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1–30 amino acids, preferably 5–15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NO:200–202, 207, 209, and 215 or those encoded by a polynucleotide sequence set forth in any one of SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, 208, and 210–214.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1–30 amino acids, preferably 5–15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAG | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86–91, 1997).

In one preferred embodiment, the immunological fusion partner is derived from a Mycobacterium sp., such as a Mycobacterium tuberculosis-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158,585; see also, Skeiky et al., *Infection and Immun.* (1999) 67:3998–4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, 208 and 210–214, complements of a polynucleotide sequence set forth as described above, and degenerate variants of a polynucleotide sequence set forth as described above. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NO:1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, 203–206, 208 and 210–214, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60–65° C. or 65–70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (ie., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. Jun. 10, 1988;240(4858):1544–6; Vasanthakumar and Ahmed, Cancer Commun. 1989;1(4):225–32; Peris et al., Brain Res Mol Brain Res. Jun. 15, 1998;57(2):310–20; U.S. Pat. No. 5,801,154; U.S. Pat. No. 5,789,573; U.S. Pat. No. 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, Tm, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389–402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. Jul. 15, 1997;25(14):2730–6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December;84(24):8788–92; Forster and Symons, Cell. Apr. 24, 1987;49(2):211–20). For example, a large number of ribozymes accelerate phosphoester transfer reactions with a high degree of specificity, often cleaving only one of several phosphoesters in an oligonucleotide substrate (Cech et al., Cell. 1981 December;27(3 Pt 2):487–96; Michel and Westhof, J Mol Biol. Dec. 5, 1990;216(3):585–610; Reinhold-Hurek and Shub, Nature. May 14, 1992;357(6374):173–6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al, Proc Natl Acad Sci USA. Aug. 15, 1992;89(16):7305–9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. Sep. 11, 1992;20(17):4559–65. Examples of hairpin motifs are described by Hampel et al. (Eur. Pat. Appl. Publ. No. EP 0360257), Hampel and Tritz, Biochemistry Jun. 13, 1989;28(12):4929–33; Hampel et al., Nucleic Acids Res. Jan. 25, 1990;18(2):299–304 and U.S. Pat. No. 5,631,359. An example of the hepatitis δ virus motif is described by Perrotta and Been, Biochemistry. Dec. 1, 1992;31(47):11843–52; an example of the RNaseP motif is described by Guerrier-Takada et al., Cell. 1983 December;35(3 Pt 2):849–57; Neurospora VS RNA ribozyme motif is described by Collins (Saville and Collins, Cell. May 18, 1992;61(4):685–96; Saville and Collins, Proc Natl Acad Sci USA. Oct. 1, 1991;88(19):8826–30; Collins and Olive, Biochemistry. Mar. 23, 1991;32(11):2795–9); and an example of the Group I intron is described in (U.S. Pat. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g, Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431–37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June;15(6):224–9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science Dec.* 6, 1991;254(5037):1497–500; Hanvey et al., Science. Nov. 27, 1992;258(5087):1481–5; Hyrup and Nielsen, Bioorg Med Chem. 1996 January;4(1):5–23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April;3(4):437–45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April;3(4):437–45; Petersen et al., J Pept Sci. 1995 May–June;1(3):175–83; Orum et al, Biotechniques. 1995 September;19(3):472–80; Footer et al., Biochemistry. Aug. 20, 1996;35(33):10673–9; Griffith et al., Nucleic Acids Res. Aug. 11, 1995;23(15):3003–8; Pardridge et al., Proc Natl Acad Sci USA. Jun. 6, 1995;92(12):5592–6; Boffa et al., Proc Natl Acad Sci USA. Mar. 14, 1995;92(6):1901–5; Gambacorti-Passerini et al., Blood. Aug. 15, 1996;88(4):1411–7; Armitage et al., Proc Natl Acad Sci USA. Nov. 11, 1997;94(23):12320–5; Seeger et al., Biotechniques. 1997 September;23(3):512–7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. Dec. 15, 1993;65(24):3545–9) and Jensen et al. (Biochemistry. Apr. 22, 1997;36(16):5072–7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturers instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., PCR *Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 43 1A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, ie., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, Autographa califomica nuclear polyhedrosis virus (AcNPV) is used as a vector to express foreign genes in *Spodoptera frugiperda* cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or Trichoplusia larvae in which the polypeptide of interest may be expressed (Engelhard, E. K. et al. (1994) *Proc. Natl. Acad. Sci.* 91 :3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439–473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as ovarian cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "$F(ab')_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659–2662; Hochman et al. (1976) Biochem 15:2706–2710; and Ehrlich et al. (1980) Biochem 19:4091–4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293–299; Lobuglio et al. (1989) Proc. Nat. Acad. Sci. USA 86:4220–4224; Shaw et al. (1987) J Immunol. 138:4534–4538; and Brown et al. (1987) Cancer Res. 47:3577–3583), rodent CDRs grafted into a human supporting FR prior to fusion with an appropriate human antibody constant domain (Riechmann et al. (1988) Nature 332:323–327; Verhoeyen et al. (1988) Science 239:1534–1536; and Jones et al. (1986) Nature 321:522–525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml–100 $\mu$g/ml, preferably 200 ng/ml–25 $\mu$g/ml) for 3–7 days will typically result in at least a two fold increase in proliferation of the T cells. Contact as described above for 2–3 hours should result in activation of the T cells, as measured using standard cytokine assays in which a two fold increase in the level of cytokine release (e.g., TNF or IFN-$\gamma$) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143–198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as Bacillus-Calmette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980–990; Miller, A. D. (1990) Human Gene Therapy 1:5–14; Scarpa et al. (1991) Virology 180:849–852; Burns et al. (1993) Proc. Natl. Acad. Sci. USA 90:8033–8037; and Boris-Lawrie and Temin (1993) Cur. Opin. Genet. Develop. 3:102–109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267–274; Bett et al. (1993) J. Virol. 67:5911–5921; Mittereder et al. (1994) Human Gene Therapy 5:717–729; Seth et al. (1994) J. Virol. 68:933–940; Barr et al. (1994) Gene Therapy 1:51–58; Berkner, K. L. (1988) BioTechniques 6:616–629; and Rich et al. (1993) Human Gene Therapy 4:461–476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; Kotin, R. M. (1994) Human Gene Therapy 5:793–801; Shelling and Smith (1994) Gene Therapy 1:165–169; and Zhou et al. (1994) J. Exp. Med. 179:1867–1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743–6747; Fuerst et al. Proc. Natl. Acad. Sci. USA (1986) 83:8122–8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866–6869 and Wagner et al. Proc. Natl. Acad. Sci. USA (1992) 89:6099–6103, can also be used for gene delivery under the invention.

Additional illustrative information on these and other known viral-based delivery systems can be found, for example, in Fisher-Hoch et al., *Proc. Natl. Acad. Sci. USA* 86:317–321, 1989; Flexner et al., *Ann. N.Y Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Pat. No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less, injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins . Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n—A—R, \qquad (I)$$

wherein, n is 1–50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g, CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature Mar. 27, 1997;386(6623):410–4; Hwang et al., Crit Rev Ther Drug Carrier Syst 1998;15(3):243–84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation.

Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release Mar. 2, 1998;52(1–2):81–7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July;16(7):307–21; Takakura, Nippon Rinsho 1998 March;56(3):691–5; Chandran et al., Indian J Exp Biol. 1997 August;35(8):801–9; Margalit, Crit Rev Ther Drug Carrier Syst. 1995;12(2–3):233–61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. Sep. 25, 1990;265(27):16337–42; Muller et al., DNA Cell Biol. 1990 April;9(3):221–9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December;24(12):1113–28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988;5(1):1–20; zur Muhlen et al., Eur J Pharm Biopharm. 1998 March;45(2):149–55; Zambaux et al. J Controlled Release. Jan. 2, 1998;50(1–3):31–40; and U.S. Pat. No. 5,145,684.

Cancer Therapeutic Methods

In further aspects of the present invention, the pharmaceutical compositions described herein may be used for the treatment of cancer, particularly for the immunotherapy of ovarian cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more ovarian tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding an ovarian tumor protein, which is also indicative of the presence or absence of a cancer. In general, a ovarian tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand comer (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 $\mu$g/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLES

Example 1

Identification of Representative Ovarian Carcinoma cDNA Sequences

Primary ovarian tumor and metastatic ovarian tumor cDNA libraries were each constructed in kanamycin resistant pZErO™-2 vector (Invitrogen) from pools of three different ovarian tumor RNA samples. For the primary ovarian tumor library, the following RNA samples were used: (1) a moderately differentiated papillary serous carcinoma of a 41 year old, (2) a stage IIIC ovarian tumor and (3) a papillary serous adenocarcinoma for a 50 year old caucasian. For the metastatic ovarian tumor library, the RNA samples used were omentum tissue from: (1) a metastatic poorly differentiated papillary adenocarcinoma with psammoma bodies in a 73 year old, (2) a metastatic poorly differentiated adenocarcinoma in a 74 year old and (3) a metastatic poorly differentiated papillary adenocarcinoma in a 68 year old.

The number of clones in each library was estimated by plating serial dilutions of unamplified libraries. Insert data were determined from 32 primary ovarian tumor clones and 32 metastatic ovarian tumor clones. The library characterization results are shown in Table I.

TABLE I

Characterization of cDNA Libraries

| Library | # Clones in Library | Clones with Insert (%) | Insert Size Range (bp) | Ave. Insert Size (bp) |
|---|---|---|---|---|
| Primary Ovarian Tumor | 1,258,000 | 97 | 175–8000 | 2356 |
| Metastatic Ovarian Tumor | 1,788,000 | 100 | 150–4300 | 1755 |

Four subtraction libraries were constructed in ampicillin resistant pcDNA3.1 vector (Invitrogen). Two of the libraries were from primary ovarian tumors and two were from metastatic ovarian tumors. In each case, the number of restriction enzyme cuts within inserts was minimized to generate full length subtraction libraries. The subtractions were each done with slightly different protocols, as described in more detail below.

A. POTS 2 Library: Primary Ovarian Tumor Subtraction Library

| | |
|---|---|
| Tracer | 10 μg primary ovarian tumor library, digested with Not I |
| Driver | 35 μg normal pancreas in pcDNA3.1 (+) |
| | 20 μg normal PBMC in pcDNA3.1 (+) |
| | 10 μg normal skin in pcDNA3.1 (+) |
| | 35 μg normal bone marrow in pZErO ™-2 |
| | Digested with Bam HI/Xho I/Sca I |

Two hybridizations were performed, and Not I-cut pcDNA3.1(+) was the cloning vector for the subtracted library. Sequence results for previously unidentified clones that were randomly picked from the subtracted library are presented in Table II.

TABLE II

Ovarian Carcinoma Sequences

| Sequence | SEQ ID NO |
|---|---|
| 21907 | 1 |
| 21909 | 2 |
| 21911 | 5 |
| 21920 | 9 |
| 21921 | 10 |
| 25099 | 143 |
| 25101 | 144 |
| 25103 | 145 |
| 25107 | 146 |
| 25111 | 148 |
| 25113 | 149 |
| 25115 | 150 |
| 25116 | 151 |
| 25752 | 156 |
| 25757 | 158 |
| 25763 | 160 |
| 25769 | 161 |
| 25770 | 162 |

B. POTS 7 Library: Primary Ovarian Tumor Subtraction Library

| | |
|---|---|
| Tracer | 10 μg primary ovarian tumor library, digested with Not I |
| Driver | 35 μg normal pancreas in pcDNA3.1 (+) |
| | 20 μg normal PBMC in pcDNA3.1 (+) |
| | 10 μg normal skin in pcDNA3.1 (+) |
| | 35 μg normal bone marrow in pZErO ™-2 |
| | Digested with Bam HI/Xho I/Sca I |
| | ~25 μg pZErO ™-2, digested with BAM HI and Xho I |

Two hybridizations were performed, and Not I-cut pcDNA3.1(+) was the cloning vector for the subtracted library. Sequence results for previously unidentified clones that were randomly picked from the subtracted library are presented in Table III.

TABLE III

Ovarian Carcinoma Sequences

| Sequence | SEQ ID NO |
|---|---|
| 24937 | 125 |
| 24940 | 128 |
| 24946 | 132 |
| 24950 | 133 |
| 24951 | 134 |
| 24955 | 136 |
| 24956 | 137 |
| 25791 | 166 |
| 25796 | 167 |
| 25797 | 168 |
| 25804 | 171 |

C. OS1D Library: Metastatic Ovarian Tumor Subtraction Library

| | |
|---|---|
| Tracer | 10 μg metastatic ovarian library in pZErO ™-2, digested with Not I |
| Driver | 24.5 μg normal pancreas in pcDNA3.1 |
| | 14 μg normal PBMC in pcDNA3.1 |
| | 14 μg normal skin in pcDNA3.1 |
| | 24.5 μg normal bone marrow in pZErO ™-2 |
| | 50 μg pZErO ™-2, digested with BAM HI/Xho I/Sfu I |

Three hybridizations were performed, and the last two hybridizations were done with an additional 15 μg of biotinylated pZErO™-2 to remove contaminating pZErO™-2 vectors. The cloning vector for the subtracted library was pcDNA3.1/Not I cut. Sequence results for previously unidentified clones that were randomly picked from the subtracted library are presented in Table IV.

TABLE IV

Ovarian Carcinoma Sequences

| Sequence | SEQ ID NO |
|---|---|
| 23645.1 | 13 |
| 23660.1 | 16 |
| 23666.1 | 19 |
| 23679.1 | 23 |
| 24635 | 57 |
| 24647 | 63 |
| 24651 | 65 |
| 24661 | 69 |
| 24663 | 70 |
| 24664 | 71 |
| 24670 | 72 |
| 24675 | 75 |
| 24683 | 78 |

D. OS1F Library: Metastatic Ovarian Tumor Subtraction Library

| | |
|---|---|
| Tracer | 10 μg metastatic ovarian tumor library, digested with Not I |
| Driver | 12.8 μg normal pancreas in pcDNA3.1 |
| | 7.3 μg normal PBMC in pcDNA3.1 |
| | 7.3 μg normal skin in pcDNA3.1 |
| | 12.8 μg normal bone marrow in pZErO ™-2 |
| | 25 μg pZErO ™-2, digested with BAM HI/Xho I/Sfu I |

One hybridization was performed. The cloning vector for the subtracted library was pcDNA3.1/Not I cut. Sequence results for previously unidentified clones that were randomly picked from the subtracted library are presented in Table V.

TABLE V

Ovarian Carcinoma Sequences

| Sequence | SEQ ID NO |
|---|---|
| 24336 (79% with *H. sapiens* mitochondrial genome (consensus sequence)) | 27 |
| 24337 | 28 |

TABLE V-continued

Ovarian Carcinoma Sequences

| Sequence | SEQ ID NO |
|---|---|
| 24341 (91% *Homo sapiens* chromosome 5, BAC clone 249h5 (LBNL H149) | 32 |
| 24344 | 33 |
| 24348 | 35 |
| 24351 | 38 |
| 24355 (91% *Homo sapiens* chromosome 17, clone hCIT.91_J_4) | 41 |
| 24356 | 42 |
| 24357 (87% *S. scrofa* mRNA for UDP glucose pyrophosphorylase) | 43 |
| 24358 | 44 |
| 24359 (78% Human mRNA for KIAA0111 gene, complete cds) | 45 |
| 24360 | 46 |
| 24361 | 47 |
| 24362 (88% *Homo sapiens* Chromosome 16 BAC clone CIT987SK-A-233A7) | 48 |
| 24363 (87% *Homo sapiens* eukaryotic translation elongation factor 1 alpha 1 (EEF1A1) | 49 |
| 24364 (89% Human DNA sequence from PAC 27K14 on chromosome Xp11.3—Xp11.4) | 50 |
| 24367 (89% *Homo sapiens* 12p13.3 BAC RCPI11-935C2) | 52 |
| 24368 | 53 |
| 24690 | 81 |
| 24692 | 82 |
| 24694 | 84 |
| 24696 | 86 |
| 24699 | 89 |
| 24701 | 90 |
| 24703 | 91 |
| 24704 (88% *Homo sapiens* chromosome 9, clone hRPK.401_G_18) | 92 |
| 24705 | 93 |
| 24707 | 95 |
| 24709 | 97 |
| 24711 | 98 |
| 24713 | 99 |
| 24714 (91% Human DNA sequence from clone 125N5 on chromosome 6q26-27) | 100 |
| 24717 (89% *Homo sapiens* proliferation-associated gene A (natural killer-enhancing factor A) (PAGA) | 103 |
| 24727 | 107 |
| 24732 | 111 |
| 24737 (84% Human ADP/ATP translocase mRNA) | 114 |
| 24741 | 117 |
| 24745 | 120 |
| 24746 | 121 |

The sequences in Table VI, which correspond to known sequences, were also identified in the above libraries.

TABLE VI

Ovarian Carcinoma Sequences

| Identity | SEQ ID NO | Sequence | Library |
|---|---|---|---|
| *H. sapiens* DNA for muscle nicotinic acetylcholine receptor gene promotor, clone ICRFc105F02104 | 3 | 21910 | POTS2 |
| *Homo sapiens* complement component 3 (C3) gene, exons 1–30. | 4 | 21913 | POTS2 |
| *Homo sapiens* SWI/SNF related, matrix associated, actin dependent regulator of chromatin, subfamily a, member 4 (SMARCA4) | 6 | 21914 | POTS2 |
| Human ferritin Heavy subunit mRNA, complete cds. | 7 | 21915 | POTS2 |
| *Homo sapiens* CGI-151 protein mRNA, complete cds | 8 | 21916 | POTS2 |
| Human BAC clone GS055K18 from 7p15–p21 | 11 | 23636.1 | OS1D |

TABLE VI-continued

Ovarian Carcinoma Sequences

| Identity | SEQ ID NO | Sequence | Library |
|---|---|---|---|
| HUMGFIBPA Human growth hormone-dependent insulin-like growth factor-binding protein | 12 | 23637.1 | OS1D |
| *Homo sapiens* ribosomal protein, large, P0 (RPLP0) mRNA | 14 | 23647.1 | OS1D |
| HUMTRPM2A Human TRPM-2 mRNA | 15 | 23657.1 | OS1D |
| HUMMTA *Homo sapiens* mitochondrial DNA | 17 | 23661.1 | OS1D |
| HSU78095 *Homo sapiens* placental bikunin mRNA | 18 | 23662.1 | OS1D |
| HUMT1227HC Human mRNA for TI-227H | 20 | 23669.1 | OS1D |
| HUMMTCG Human mitochondrion | 21 | 23673.1 | OS1D |
| *Homo sapiens* FK506-binding protein 1A (12kD) (FKBP1A) mRNA | 22 | 23677.1 | OS1D |
| *Homo sapiens* mRNA for zinc-finger DNA-binding protein, complete cds | 24 | 24333 | OS1F |
| *Homo sapiens* mRNA; cDNA DKFZp564E1962 (from clone DKFZp564E1962) | 25 | 24334 | OS1F |
| *Homo sapiens* tumor protein, translationally-controlled 1 (TPT1) mRNA. | 26 | 24335 | OS1F |
| *Homo sapiens* interleukin 1 receptor accessory protein (IL1RAP) mRNA. | 29 | 24338 | OS1F |
| Human mRNA for K1AA0026 gene | 30 | 24339 | OS1F |
| *Homo sapiens* K-Cl cotransporter KCC4 mRNA, complete cds | 31 | 24340 | OS1F |
| *Homo sapiens* nuclear chloride ion channel protein (NCC27) mRNA | 34 | 24345 | OS1F |
| *Homo sapiens* mRNA for DEPP (decidual protein induced by progesterone) | 36 | 24349 | OS1F |
| *Homo sapiens* atrophin-1 interacting protein 4 (AIP4) mRNA | 37 | 24350 | OS1F |
| Human collagenase type IV mRNA, 3' end. | 39 | 24352 | OS1F |
| Human mRNA for T-cell cyclophilin | 40 | 24354 | OS1F |
| *Homo sapiens* tumor suppressing subtransferable candidate 1 (TSSC1) | 51 | 24366 | OS1F |
| *Homo sapiens* clone 24452 mRNA sequence | 54 | 24374 | OS1F |
| *Homo sapiens* eukaryotic translation elongation factor 1 alpha 1 (EEF1A1) | 55 | 24627 | OS1D |
| Genomic sequence from Human 9q34 | 56 | 24634 | OS1D |
| Human insulin-like growth factor-binding protein-3 gene | 58 | 24636 | OS1D |
| Human ribosomal protein L3 mRNA, 3' end | 59 | 24638 | OS1D |
| *Homo sapiens* annexin II (lipocortin II) (ANX2) mRNA | 60 | 24640 | OS1D |
| *Homo sapiens* tubulin, alpha, ubiquitous (K-ALPHA-1) | 61 | 24642 | OS1D |
| Human non-histone chromosomal protein HMG-14 mRNA | 62 | 24645 | OS1D |
| *Homo sapiens* ferritin, heavy polypeptide 1 (FTH1) | 64 | 24648 | OS1D |
| *Homo sapiens* 12p13.3 PAC RPCI1-96H9 (Roswell Park Cancer Institute Human PACLibrary) | 66 | 24653 | OS1D |
| *Homo sapiens* T cell-specific tyrosine kinase mRNA | 67 | 24655 | OS1D |
| *Homo sapiens* keratin 18 (KRT18) mRNA | 68 | 24657 | OS1D |
| *Homo sapiens* growth arrest specific transcript 5 gene | 73 | 24671 | OS1D |
| *Homo sapiens* ribosomal protein S7 (RPS7) | 74 | 24673 | OS1D |
| *Homo sapiens* mRNA; cDNA DKFZp564H182 | 76 | 24677 | OS1D |
| Human TSC-22 protein mRNA | 77 | 24679 | OS1D |
| Human mRNA for ribosomal protein | 79 | 24687 | OS1D |
| Genomic sequence from Human 13 | 80 | 24689 | OS1F |
| *Homo sapiens* clone IMAGE 286356 | 83 | 24693 | OS1F |
| *Homo sapiens* v-fos FBJ murine osteosarcoma viral oncogene homolog(FOS) mRNA | 85 | 24695 | OS1F |
| *Homo sapiens* hypothetical 43.2 Kd protein mRNA | 87 | 24697 | OS1F |
| Human heat shock protein 27 (HSPB1) gene exons 1–3 | 88 | 24698 | OS1F |
| *Homo sapiens* senescence-associated epithelial membrane protein (SEMP1) | 94 | 24706 | OS1F |
| Human ferritin H chain mRNA | 96 | 24708 | OS1F |
| *Homo sapiens* mRNA for KIAA0287 gene | 101 | 24715 | OS1F |
| *Homo sapiens* CGI-08 protein mRNA | 102 | 24716 | OS1F |
| *H. sapiens* CpG island DNA genomic Msel fragment, clone 84a5 | 104 | 24719 | OS1F |
| Human clone 23722 mRNA | 105 | 24721 | OS1F |
| *Homo sapiens* zinc finger protein slug (SLUG) gene | 106 | 24722 | OS1F |
| *Homo sapiens* (clone L6) E-cadherin (CDH1) gene | 108 | 24728 | OS1F |
| *Homo sapiens* ribosomal protein L13 (RPL13) | 109 | 24729 | OS1F |
| *H. sapiens* RNA for snRNP protein B | 110 | 24730 | OS1F |

TABLE VI-continued

| Ovarian Carcinoma Sequences | | | |
|---|---|---|---|
| Identity | SEQ ID NO | Sequence | Library |
| *Homo sapiens* mRNA; cDNA DKFZp434K114 | 112 | 24734 | OS1F |
| *Homo sapiens* cornichon protein mRNA | 113 | 24735 | OS1F |
| *Homo sapiens* keratin 8 (KRT8) mRNA | 115 | 24739 | OS1F |
| Human DNA sequence from PAC 29K1 on chromosome 6p21.3–22.2. | 116 | 24740 | OS1F |
| *Homo sapiens* mRNA for KIAA0762 protein | 118 | 24742 | OS1F |
| Human clones 23667 and 23775 zinc finger protein mRNA | 119 | 24744 | OS1F |
| Human H19 RNA gene, complete cds. | 122 | 24933 | POTS7 |
| Human triosephosphate isomerase mRNA, complete cds. | 123 | 24934 | POTS7 |
| Human cyclooxygenase-1 (PTSG1) mLRNA, partial cds | 124 | 24935 | POTS7 |
| *Homo sapiens* megakaryocyte potentiating factor (MPF) mRNA. | 126 | 24938 | POTS7 |
| Human mRNA for Apo1_Human (MER5(Aop1-Mouse)-like protein), complete cds | 127 | 24939 | POTS7 |
| *Homo sapiens* arylacetamide deacetylase (esterase) (AADAC) mRNA. | 129 | 24942 | POTS7 |
| *Homo sapiens* echinoderm microtubule-associated protein-like EMAP2 mRNA, complete cds | 130 | 24943 | POTS7 |
| *Homo sapiens* podocalyxin-like (PODXL) mRNA. | 131 | 24944 | POTS7 |
| *Homo sapiens* synaptogyrin 2 (SYNGR2) mRNA. | 135 | 24952 | POTS7 |
| *Homo sapiens* amyloid beta precursor protein-binding protein 1, 59kD (APPBP1) mRNA. | 138 | 24959 | POTS7 |
| Human aldose reductase mRNA, complete cds. | 139 | 24969 | POTS7 |
| Genomic sequence from Human 9q34, complete sequence [*Homo sapiens*] | 140 | 25092 | POTS2 |
| Human glyceraldehyde-3-phosphate dehydrogenase (GAPDH) mRNA, complete cds. | 141 | 25093 | POTS2 |
| *Homo sapiens* breast cancer suppressor candidate 1 (bcsc-1) mRNA, complete cds | 142 | 25098 | POTS2 |
| *Homo sapiens* SKB1 (*S. cerevisiae*) homolog (SKB1) mRNA. | 147 | 25110 | POTS2 |
| *Homo sapiens* prepro dipeptidyl peptidase I (DPP-I) gene, complete cds | 152 | 25117 | POTS2 |
| *Homo sapiens* preferentially expressed antigen of melanoma (PRAME) mRNA | 153 | 25745 | POTS2 |
| Human translocated t(8;14) c-myc (MYC) oncogene, exon 3 and complete cds | 154 | 25746 | POTS2 |
| Human 12S RNA induced by poly(rI), poly(rC) and Newcastle disease virus | 155 | 25749 | POTS2 |
| Human mRNA for fibronectin (FN precursor) | 157 | 25755 | POTS2 |
| *Homo sapiens* mRNA for hepatocyte growth factor activator inhibitor type 2, complete cds | 159 | 25758 | POTS2 |
| *Homo sapiens* mRNA for KIAA0552 protein, complete cds | 163 | 25771 | POTS7 |
| *Homo sapiens* IMP (inosine monophosphate) dehydrogenase 2 (IMPDH2) mRNA | 164 | 25775 | POTS7 |
| *Homo sapiens* clone 23942 alpha enolase mRNA, partial cds | 165 | 25787 | POTS7 |
| *H. sapiens* vegf gene, 3'UTR | 169 | 25799 | POTS7 |
| *Homo sapiens* 30S ribosomal protein S7 homolog mRNA, complete cds | 170 | 25802 | POTS7 |
| *Homo sapiens* acetyl-Coenzyme A acetyltransferase 2 (acetoacetyl Coenzyme A thiolase) (ACAT2) mRNA | 172 | 25808 | POTS7 |
| *Homo sapiens* Norrie disease protein (NDP) mRNA | 173 | 25809 | POTS7 |

Still further ovarian carcinoma polynucleotide and/or polypeptide sequences identified from the above libaries are provided below in Table VII. Sequences O574S (SEQ ID NO:183 & 185), O584S (SEQ ID NO:193) and O585S (SEQ ID NO:194) represent novel sequences. The remaining sequences exhibited at least some homology with known genomic and/or EST sequences.

TABLE VII

| SEQ ID: | Sequence | Library |
|---|---|---|
| 174: | O565S_CRABP | OS1D |
| 175: | O566S_Ceruloplasmin | POTS2 |
| 176: | O567S_41191.SEQ(1>487) | POTS2 |
| 177: | O568S_KIAA0762.seq(1>3999) | POTS7 |
| 178: | O569S_41220.seq(1>1069) | POTS7 |
| 179: | O570S_41215.seq(1>1817) | POTS2 |
| 180: | O571S_41213.seq(1>2382) | POTS2 |
| 181: | O572S_41208.seq(1>2377) | POTS2 |
| 182: | O573S_41177.seq(1>1370) | OS1F |
| 183: | O574S_47807.seq(1>2060) | n/a |
| 184: | O568S/VSGF DNA seq | n/a |
| 185: | O574S_47807.seq(1>3000) | n/a |
| 186: | O568S/VSGF protein seq | n/a |
| 187: | 449H1(57581) | OS1D |
| 188: | 451E12(57582) | OS1D |
| 189: | 453C7_3'(57583.1)Osteonectin | OS1D |
| 190: | 453C7_5'(57583.2) | OS1D |
| 191: | 456G1_3'(57584.1)Neurotensin | OS1F |
| 192: | 456G1_5'(57584.2) | OS1F |
| 193: | O584S_465G5(57585) | OS1F |
| 194: | O585S_469B12(57586) | POTS2 |
| 195: | O569S_474C3(57587) | POTS7 |
| 196: | 483B1_3'(24934.1)Triosephosphate | POTS7 |
| 197: | 57885 Human preferentially expressed antigen of melanoma | POTS2 |
| 198: | 57886 Chromosome 22q12.1 clone CTA-723E4 | POTS2 |
| 199: | 57887 Homologous to mouse brain cDNA clone MNCb-0671 | POTS2 |

Further studies on the clone of SEQ ID NO:182 (also referred to as O573S) led to the identification of multiple open reading frames that encode the amino acid sequences of SEQ ID NO:200–202.

Example 2

Analysis of cDNA Expression Using Microarray Technology

In additional studies, sequences disclosed herein were found to be overexpressed in specific tumor tissues as determined by microarray analysis. Using this approach, cDNA sequences are PCR amplified and their mRNA expression profiles in tumor and normal tissues are examined using cDNA microarray technology essentially as described (Shena et al., 1995). In brief, the clones are arrayed onto glass slides as multiple replicas, with each location corresponding to a unique cDNA clone (as many as 5500 clones can be arrayed on a single slide or chip). Each chip is hybridized with a pair of cDNA probes that are fluorescence-labeled with Cy3 and Cy5 respectively. Typically, 1 $\mu$g of polyA$^+$ RNA is used to generate each cDNA probe. After hybridization, the chips are scanned and the fluorescence intensity recorded for both Cy3 and Cy5 channels. There are multiple built-in quality control steps. First, the probe quality is monitored using a panel of ubiquitously expressed genes. Secondly, the control plate also can include yeast DNA fragments of which complementary RNA may be spiked into the probe synthesis for measuring the quality of the probe and the sensitivity of the analysis. Currently, the technology offers a sensitivity of 1 in 100,000 copies of mRNA. Finally, the reproducitility of this technology can be ensured by including duplicated control cDNA elements at different locations.

The microarray results for clones 57885 (SEQ ID NO:197), 57886 (SEQ ID NO:198) and 57887 (SEQ ID NO:199) are as follows.

Clone 57885: 16/38 (42%) of ovarian tumors showed an expression signal value of >0.4. The mean value for all ovary tumors was 0.662 with a mean value of 0.187 for all normal tissues, which yields a 3.64 fold overexpression level in ovary tumor relative to essential normal tissues. Normal tissue expression was elevated (>0.4) in peritoneum, skin and thymus.

Clone 57886: 16/38 (42%) of ovarian tumors showed an expression signal value of >0.4. The mean value for all ovary tumors was 0.574 with a mean value of 0.166 for all normal tissues which yields a 3.46 fold overexpression level in ovary tumor relative to essential normal tissues. Normal tissue expression was elevated (>0.4) in heart, pancreas and small intestive.

Clone 57887: 17/38 (44%) of ovarian tumors showed an expression signal value of >0.4. The mean value for all ovary tumors is 0.744 with a mean value of 0.184 for all normal tissues which yields a 4.04 fold overexpression level in ovary tumor relative to essential normal tissues. Normal tissue expression was elevated (>0.4) in esophagus.

Example 3

Expression of Recombinant Antigen O568S in *E. coli*

This example describes the expression of recombinant antigen O568S (SEQ ID NO:177) in *E. coli*. This sequence was identified in Example 1 from the POTS 7 subtraction library using primary ovarian tumor EDNA as the tracer. PCR primers specific for the open reading frame of O568S were designed and used in the specific amplification of O568S. The PCR product was enzymatically digested with EcoRI and ligated into pPDM, a modified pET28 vector which had been cut with the restriction enzymes EcoRI and Eco72I. The construct sequence and orientation was confirmed through sequence analysis, the sequence of which is shown in SEQ ID NO:206. The vector was then transformed into the expression hosts, BLR (DE3) and HMS 174 (DE3) pLys S. Protein expression was confirmed, the sequence of which is provided in SEQ ID NO:207.

Example 4

Additional Sequence Obtained for Clone O591S

The sequence of O591S (clone identifier 57887) was used to search public sequence databases. It was found that the reverse strand showed some degree of identity to the C-terminal end of GPR39. The cDNA for the coding region of GPR39 is disclosed in SEQ ID NO:208 and the corresponding amino acid sequence in SEQ ID NO:209. The GPR39 coding region contains two exons. Both O591S and GPR39, encoded by the complementary strand of O591S, are located on chromosome 2.

Example 5

Further Characterization of O591S and Identificaton of Extended Sequence

O1034C is an ovary specific gene identified by electronic subtraction. Briefly, electronic subtraction involves an analysis of EST database sequences to identify ovarian-specific genes. In the electronic subtraction method used to indentify O1034C, sequences of EST clones derived from ovary libraries (normal and tumor) were obtained from the GenBank public human EST database. Each ovary sequence was used as a "seed" query in a BLASTN search of the total human EST database to identify other EST clones that share sequence with the seed sequence (clones that potentially originated from the same mRNA). EST clones with shared sequence were grouped into clusters, and clusters that shared sequence with other clusters were grouped into superclusters. The tissue source of each EST within each supercluster was noted, and superclusters were ranked based on the distribution of the tissues from which the ESTs originated. Superclusters that comprise primarily, or solely, EST clones from ovary libraries were considered to represent genes that were differentially expressed in ovary tissue, relative to all other normal adult tissue.

This clone was identified from the public EST databases as Integrated Molecular Analysis of Genomics and their Expression (IMAGE) clone number 595449 (the IMAGE consortium is a repository of EST clones and cDNA clones) and is disclosed as SEQ ID NO:210. Accession numbers AA173739 and AA173383 represents the sequence of the identified EST in Genebank. This clone is part of Unigene cluster HS.85339 (Unigene is an experimental system for automatically partitioning Genbank sequences into a non-redundant set of gene-orientated clusters) and was annotated as encoding a neurotensin-like G protein coupled receptor (GRP39). However, the inventors have discovered that IMAGE#595449 encodes a novel protein derived from the complementary strand to that which encodes the potential GPR39.

Microarray analysis of the clone using a series of ovary tumor specific probes indicated that this clone was over expressed 4.95-fold in a group of ovary tumor and normal ovary samples as compared to a group of essential normal tissue samples.

IMAGE#59449 was subjected to a Blast A search of the EST database and Genbank and an electronic full length clone contig (O1034C) was generated by extending IMAGE#595449 and its resulting contigs to completeion. This process was repeated to completion when no further EST sequences were identified to extend the consensus sequence. This electronically derived clone was identified as coding a previously described clone, O591S, the sequence of which is disclosed in SEQ ID NO:211. The discovery of this ovary specific candidate is described in more detail in Example 4.

The consensus sequence for O1034C extended further 5' than O591S due to the additional sequences derived from two EST clones, accession numbers BF345141 and BE336607, the sequences for which are disclosed in SEQ ID NO:212 and 213 respectively. Although BF345141 diverges from the O1034C/O591S consensus at its 3'-end (possibly representing a different splice form), and from BE336607 at several bases at its 5'-end, the two ESTs were compared to the available matching chromosome sequence. They were found on human chromosome 2, clone RP11-159N20:htgs database accession number AC010974. These sequences were used to extend O01034C/O591S to form a final consensus sequence for O1034C/O591S of 1897 base pairs, disclosed in SEQ ID NO:214.

An open reading frame (ORF) was identified within the O1034C/O591S consensus sequence (nucleotides 260–682), the predicted translation of which is disclosed in SEQ ID NO:215. A BLASTx database search against the Genbank database indicated that this ORF had no identity (E value<1e-25) with any known human protein. The only match was with the G protein-coupled receptors, including GPR39, which the inventors have shown to be encoded at the 3'-end of O1034C/O591S on the complementary strand. However, the ORF did encode a protein that had 93% similarity (131/141 amino acids) and 91% identity (129/141 amino acids) with an un-named murine product (Accession #BAA95101), suggesting that this is a real translation product that represents a novel human ovary-specific antigen.

The novelty of O1034C/O591S was confirmed by Northern Blot analysis using single stranded probes that complement either GRP39 or O1034C/O591S. The strand-specific O1034C/O591S probe specifically hybridized to the ovary tumor samples probed on the Northen blot, whilst all samples were negative when probed with GPR39. In addition real-time PCR was performed using primers specific for either GPR39 or O1034C/O591S. These results further demonstrated the differential expression profiles of the two sequences. This protein is a putative membrane protein as determined from Corixa's Tmpred protein prediction algorithm.

Example 6

Expression Analysis and Further Characterization of Ovarian Sequence O568S

The ovarian sequence O568S was originally identified as cDNA clone 24742 (SEQ ID NO:118). Using clone 24742 as a query sequence to search public sequence databases, the sequence was found to have a high degree of homology with KIAA0762 (SEQ ID NO:177) and with VSGF. The DNA sequence for VSGF is provided in SEQ ID 184 and the VSGF protein sequence is provided in SEQ ID NO:186.

Real-time PCR (see Gibson et al., *Genome Research* 6:995–1001, 1996; Heid et al., *Genome Research* 6:986–994, 1996) is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR is performed, for example, using a Perkin Elmer/Applied Biosystems (Foster City, Calif.) 7700 Prism instrument. Matching primers and fluorescent probes are designed for genes of interest using, for example, the primer express program provided by Perkin Elmer/Applied Biosystems (Foster City, Calif.). Optimal concentrations of primers and probes are initially determined by those of ordinary skill in the art, and control (e.g., β-actin) primers and probes are obtained commercially from, for example, Perkin Elmer/Applied Biosystems (Foster City, Calif.). To quantitate the amount of specific RNA in a sample, a standard curve is generated using a plasmid containing the gene of interest. Standard curves are generated using the Ct values determined in the real-time PCR, which are related to the initial cDNA concentration used in the assay. Standard dilutions ranging from $10–10^6$ copies of the gene of interest are generally sufficient. In addition, a standard curve is generated for the control sequence. This permits standardization of initial RNA content of a tissue sample to the amount of control for comparison purposes.

By RealTime PCR analysis, O568 was highly overexpressed in the majority of ovary tumors and ovary tumor metastases tested relative to normal ovary tissue and relative to an extensive normal tissue panel. Little or no expression was observed in normal esophagus, spinal cord, bladder, colon, liver, PBMC (activated or resting), lung, skin, small intestine, stomach, skeletal muscle, pancreas, dendritic cells, heart, spleen bone marrow, thyroid, trachea, thymus, bronchia, cerebellum, ureter, uterus and peritoneum epithelium. Some low level expression was observed in normal breast, brain, bone, kidney, adrenal gland and salivary gland, but the expression levels in these normal tissues were generally at least several fold less than the levels observed in ovary tumors overexpressing O568S.

Moreover, a series of Northern blots was performed which also demonstrated that the ORF region of O568S is specifically overexpressed in ovary tumors. The initial blot contained RNA from a series of normal tissues as well as from ovary tumors. This blot was probed using, as a labeled probe, DNA from O568s that corresponded to the 3'UTR of the VSGF sequence disclosed in SEQ ID NO:184. This blot revealed an ovary tumor-specific 5.0 Kb message as well as a potential 3.5 Kb brain specific message and a ubiquitously expressed 1.35 Kb message.

Another Northern blot was performed with RNAs from a number of different brain tissues and probed with the 3'UTR region as above. Five of eleven brain samples showed overexpression of the 3.5 Kb message. In order to determine whether the ORF region of O568S was specifically overexpressed in ovary tumors, a series of three blots was carried out using three separate probes designed from within the VSGF ORF of O568S. Results from these experiments clearly indicated that only the 5.0 Kb message is expressed in ovary tumor.

Example 7

Synthesis of Polypeptides

Polypeptides are synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence is attached to the amino terminus of the peptide to provide a method of conjugation, binding to an immobilized surface, or labeling of the peptide. Cleavage of the peptides from the solid support is carried out using the following cleavage mixture: trifluoroacetic acid:ethanedithiol:thioanisole:water:phenol (40:1:2:2:3). After cleaving for 2 hours, the peptides are precipitated in cold methyl-t-butyl-ether. The peptide pellets are then dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) is used to elute the peptides. Following lyophilization of the pure fractions, the peptides are characterized using electrospray or other types of mass spectrometry and by amino acid analysis.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. An isolated polynucleotide comprising a sequence selected from the group consisting of:

(a) SEQ ID NO: 214; and (b) the full complement of SEQ ID NO: 214.

2. An expression vector comprising a polynucleotide of claim 1 operably linked to an expression control sequence.

3. A host cell transformed or transfected with an expression vector according to claim 2.

4. A composition comprising a first component selected from the group consisting of physiologically acceptable carriers and immunostimulants, and a second component selected from the group consisting of the polynucleotides of claim 1.

5. A diagnostic kit comprising at least one oligonucleotide according to claim 1.

* * * * *